(12) United States Patent
Szeto

(10) Patent No.: US 11,617,739 B2
(45) Date of Patent: Apr. 4, 2023

(54) METHODS AND COMPOSITIONS FOR DELIVERY OF BIOTIN TO MITOCHONDRIA

(71) Applicant: Social Profit Network, Menlo Park, CA (US)

(72) Inventor: Hazel Szeto, New York, NY (US)

(73) Assignee: Social Profit Network, Menlo Park, CA (US)

( * ) Notice: Subject to any disclaimer, the term of this patent is extended or adjusted under 35 U.S.C. 154(b) by 0 days.

(21) Appl. No.: 17/946,394

(22) Filed: Sep. 16, 2022

(65) Prior Publication Data

US 2023/0043530 A1    Feb. 9, 2023

Related U.S. Application Data

(63) Continuation of application No. 17/844,816, filed on Jun. 21, 2022, which is a continuation of application No. 17/466,661, filed on Sep. 3, 2021, now Pat. No. 11,389,431.

(60) Provisional application No. 63/076,022, filed on Sep. 9, 2020, provisional application No. 63/075,996, filed on Sep. 9, 2020.

(51) Int. Cl.
| | |
|---|---|
| *A61K 47/64* | (2017.01) |
| *C12N 5/078* | (2010.01) |
| *C12N 5/0789* | (2010.01) |
| *A61K 31/4188* | (2006.01) |
| *A61K 38/08* | (2019.01) |
| *A61K 38/07* | (2006.01) |
| *C12N 5/074* | (2010.01) |
| *C12N 5/00* | (2006.01) |

(52) U.S. Cl.
CPC .......... *A61K 31/4188* (2013.01); *A61K 38/07* (2013.01); *A61K 38/08* (2013.01); *A61K 47/64* (2017.08); *A61K 47/6455* (2017.08); *C12N 5/0031* (2013.01); *C12N 5/0607* (2013.01); *C12N 5/0634* (2013.01); *C12N 5/0647* (2013.01); *C12N 2500/38* (2013.01)

(58) Field of Classification Search
CPC .... A61K 38/08; A61K 47/64; A61K 47/6455; C07K 5/1016; C07K 5/1019; C07K 5/1024; C07K 7/06; C12N 5/0031; C12N 5/0607; C12N 5/0634; C12N 5/0647; C12N 2500/38
See application file for complete search history.

(56) References Cited

U.S. PATENT DOCUMENTS 11,389,431 B2 *   7/2022   Szeto ................. A61K 31/4188

OTHER PUBLICATIONS

Chavez et al. Mitochondrial protein interaction landscape of SS-31. Proceedings of the National Academy of Sciences. Jun. 17, 2020, vol. 17, No. 26, pp. 15363-15373, plus Supplementary Information. (Year: 2020).*

* cited by examiner

*Primary Examiner* — Jeffrey E. Russel
(74) *Attorney, Agent, or Firm* — Michael Haynes PLC; Michael N. Haynes

(57) ABSTRACT

Certain exemplary embodiments are directed to a biologically active composition of matter (and uses thereof) configured for targeted delivery of biotin to mitochondria, the composition comprising a first D-biotin conjugated to a water-soluble, cell-permeable, peptide sequence, wherein the peptide sequence is selected from a polypeptide group with an alternating aromatic-cationic motif.

31 Claims, 27 Drawing Sheets
(10 of 27 Drawing Sheet(s) Filed in Color)
Specification includes a Sequence Listing.

METHODS AND COMPOSITIONS FOR DELIVERY OF BIOTIN TO MITOCHONDRIA

CROSS-REFERENCE TO RELATED APPLICATIONS

This application claims priority to, and incorporates by reference herein in its entirety, U.S. Provisional Patent Application 63/075,996, which was filed 9 Sep. 2020, and U.S. Provisional Patent Application 63/076,022, which was filed on 9 Sep. 2020.

SEQUENCE LISTING

This application contains a Sequence Listing which has been submitted electronically in XML format. The Sequence Listing XML is incorporated herein by reference. Said XML file, created on Oct. 3, 2022, is named 1255-008_SL.xml and is 3,925 bytes in size.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A wide variety of potential, feasible, and/or useful embodiments will be more readily understood through the herein-provided, non-limiting, non-exhaustive description of certain exemplary embodiments, with reference to the accompanying exemplary drawings in which.

DETAILED DESCRIPTION

Figure 1A:
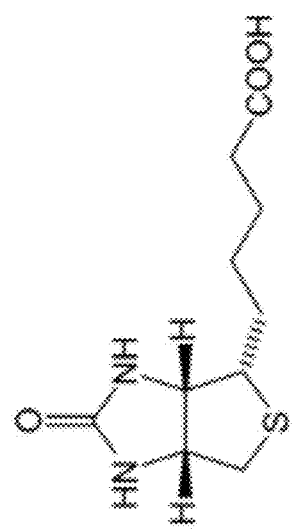
FIGS. 1A, 1B, and 1C are chemical structure diagrams showing how biotin can be conjugated to mitochondria-targeted peptide sequences.

Certain exemplary embodiments described herein can relate to methods and compositions for enhancing cellular and/or mitochondrial uptake of biotin. Targeted delivery of biotin to mitochondria can improve efficacy and avoid the use of high doses of biotin.

Certain exemplary embodiments described herein can provide a method for using water-soluble, cell-permeable, mitochondria-targeting peptide sequences to deliver biotin to mitochondria.

Certain exemplary embodiments described herein relate to short water-soluble peptide sequences selected from a polypeptide group with a general aromatic-cationic motif, meaning that the amino acids of the polypeptide group can be arranged as, e.g., [aromatic-cationic-aromatic-cationic] or [cationic-aromatic-cationic-aromatic].

Certain exemplary embodiments described herein can include polypeptides composed of naturally occurring amino acids.

Certain exemplary embodiments described herein can include D amino acids, which can help make the peptide more resistant to hydrolysis by peptidase enzymes. Certain exemplary embodiments described herein can include polypeptides composed of one or more non-naturally occurring amino acids. Non-naturally occurring amino acids are those amino acids that typically are not synthesized in normal metabolic processes in living organisms, and do not naturally occur in proteins. Non-naturally occurring amino acids can include derivatives of naturally occurring amino acids.

The peptides useful in the present invention can contain one or more non-naturally occurring amino acids. The non-naturally occurring amino acids may be L-, dextrorotatory (D), or mixtures thereof. Optimally, the peptide has no amino acids that are naturally occurring.

Non-naturally occurring amino acids are those amino acids that do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group. Certain exemplary embodiments described herein include amidation of the C-terminus of the peptide sequence, which can help make the peptide more resistant to hydrolysis by carboxypeptidases.

Carboxyl groups, especially the terminal carboxyl group of a C-terminal amino acid, can be amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

Certain exemplary embodiments described herein can include polypeptides composed of a minimum of four amino acids.

Certain exemplary embodiments described herein can include polypeptides composed of no more than six amino acids.

Certain exemplary embodiments described herein are directed to water-soluble peptide sequences selected from polypeptides composed of 4-6 amino acids (in either D or L configuration) with an alternating aromatic-cationic motif.

Certain exemplary embodiments described herein are directed to water-soluble peptide sequences including, but not limited to:

(SS-31)
D-Arg-L-(2'6'-dimethylTyr)-L-Lys-L-Phe-NH$_2$ (SPN02)
D-Arg-L-Tyr-D-Arg-L-Phe-L-Lys-NH$_2$;

(SPN07)
D-Trp-D-Arg-D-Trp-D-Lys-OH;

(SPN10) (SEQ ID NO: 1)
L-Trp-L-Arg-L-Trp-L-Lys-NH$_2$;

(SPN13)
D-Trp-D-Arg-D-Trp-D-Lys-NH$_2$;
and (SPN14) (SEQ ID NO: 2)
L-Trp-L-Arg-L-Trp-L-Lys-OH.

Certain exemplary embodiments described herein can provide methods for conjugating D-biotin to short (i.e., 4 to 6 amino acids), water-soluble, cell-permeable, mitochondria-targeting peptide sequences for targeted delivery of biotin to mitochondria.

Certain exemplary peptide sequences described herein are defined by an N-terminus and a C-terminus, and can comprise an α-amine at the N-terminus. Certain exemplary embodiments described herein can provide methods for conjugating D-biotin to the N-terminus α-amine of mitochondria-targeting peptide sequences.

Certain exemplary peptide sequences described herein can comprise a lysine residue, having an ε-amine, at their C-terminus. Certain exemplary embodiments described herein can provide methods for conjugating D-biotin to the ε-amine of lysine residues (ε-N-[d-biotinyl]-L-lysine) at the C-terminus of the mitochondria-targeting peptide sequences.

Certain exemplary embodiments described herein can provide methods for conjugating D-biotin to both the N-terminus α-amine and to the ε-amine on lysine residues at the C-terminus of the mitochondria-targeting peptide sequences.

Certain exemplary embodiments described herein are directed to at least one therapeutically effective composition of matter and/or methods for making and/or using such a composition and/or one or more of its components, the composition comprising:

one or more compounds selected from a polypeptide group consisting of:

| | |
|---|---|
| D-Biotin-D-Arg-L-(2'6'-dimethylTyr)-L-Lys-L-Phe-NH2 | (SPN05); |
| D-Biotin-D-Trp-D-Arg-D-Trp-D-Lys-OH | (SPN08); |
| D-Trp-D-Arg-D-Trp-D-Lys(biotinyl)-OH | (SPN09); |
| L-Trp-L-Arg-L-Trp-L-Lys(biotinyl)-NH$_2$ | (SPN11); |
| D-Biotin-L-Trp-L-Arg-L-Trp-L-Lys(biotinyl)-NH$_2$ | (SPN12); |
| D-Arg-L-Tyr-D-Arg-L-Phe-L-Lys(biotinyl)-NH$_2$ | (SPN15); and |
| D-Biotin-D-Arg-L-Tyr-D-Arg-L-Phe-L-Lys(biotinyl)-NH$_2$ | (SPN16). |

One or more exemplary compositions described herein can comprise one or more peptide-conjugated biotin molecules adapted to stimulate cellular ATP production. An exemplary composition can include vitamins and/or amino acids and/or metabolic supplements in effective concentrations that promote ATP synthesis.

One or more exemplary compositions described herein can comprise one or more peptide-conjugated biotin molecules adapted to preserve mitochondrial potential.

Certain exemplary embodiments described herein relate to novel compositions and/or methods adapted for promoting cell survival when cells are cultured ex vivo in the absence of serum. One or more exemplary compositions described herein can comprise one or more peptide-conjugated biotin molecules adapted to stimulate mitochondrial function, such as to promote cell proliferation. One or more exemplary compositions described herein can include vitamins and/or amino acids and/or metabolic supplements in effective concentrations that exhibit additive or synergistic activity in maintaining cell growth.

To perform cell therapy, because of the small number of stem cells, extensive ex vivo expansion is required to obtain sufficient cell numbers for treatment of a clinical indication. Media containing fetal bovine serum (FBS) provides a supportive environment for isolation and expansion of mesenchymal stem cells. FBS provides attachment factors, growth factors and a host of other nutrients. Yet, in addition to the inherent variability in FBS and a limited global supply, serum products also can be a source of pathogens and/or contain serum proteins that have the potential to elicit immune response in human recipients.

Serum depletion causes cell cycle arrest and apoptosis which severely limits the yield of stem cells or primary cells for clinical use. A variety of growth factors must be added to serum-free media to permit stem cell expansion, and this often involves the use of human-sourced supplements that might be contaminated with human pathogens. Certain exemplary media described herein comprise chemically defined yet serum-free and xeno-free constituents that support the growth and attachment of human primary cells and passaged cultures to allow large scale production of primary mammalian cells for clinical use.

Large-scale production of primary mammalian cells can be crucial for laboratory production of meat as an alternative to traditional livestock-derived meats. The culturing of animal myoblasts with FBS is not sustainable. Certain exemplary media described herein comprise chemically defined, serum-free constituents that support the proliferation of animal myoblasts for large scale production of lab-grown meats.

Certain exemplary embodiments described herein relate to novel compositions and/or methods adapted for promoting cell or tissue survival for transplantation in humans. One or more exemplary compositions described herein can comprise one or more peptide-conjugated biotin molecules adapted to stimulate mitochondrial cellular ATP production to promote cell survival. One or more exemplary compositions described herein can include vitamins and/or amino acids and/or metabolic supplements in effective concentrations that exhibit additive or synergistic activity in maintaining organ survival.

Pancreatic islet transplantation is an approach to β-cell replacement therapy for type 1 diabetics. The addition of one or more peptide-conjugated biotin molecules that can improve cell viability throughout the harvesting and purification procedure, can greatly improve islet yield, and/or increase the success of glycemic control in the recipient.

Ischemia and hypoxia are inevitable events during preservation of organs prior to transplantation. Once the organ has been deprived of normal blood supply, depletion of mitochondrial ATP synthesis leads to cell death. The duration of storage varies from 4-6 hours for heart and lungs and up to 36 hours for kidneys. The addition of one or more peptide-conjugated biotin molecules that can improve cell viability in organ preservation solutions can prolong survival time of an organ to permit broader distribution to matching recipients. Improved quality of transplant organs can also reduce delayed graft function and graft failure.

Certain exemplary embodiments described herein relate to novel compositions and/or methods adapted for promoting tissue health and/or preventing tissue injuries. Certain exemplary methods described herein provide for systemic administration of an exemplary composition to the mammal. The composition can comprise one or more peptide-conjugated biotin molecules adapted to stimulate mitochondrial cellular ATP production to promote cellular function. The composition can include vitamins and/or amino acids and/or metabolic supplements in effective concentrations that exhibit additive or synergistic activity in maintaining tissue health.

Aging is associated with decreased proliferative ability of many cell types, including skin and epithelial membranes. The intestinal epithelium completely self-renews within 5 days, while the lung epithelium can take as long as 6 months to renew. Aging diminishes the capacity of epithelial regeneration and leads to progressive epithelial injury.

Most tissues exhibit a progressive decline in regeneration capability with age that results in tissue degeneration, malfunction, and pathology. Certain methods described herein can promote tissue health during aging can prevent and/or reduce many of these age-related functional disabilities.

Exemplary methods described herein relate to novel compositions and/or methods adapted for promoting tissue health that can promote proliferation of resident stem/progenitor cells in vivo in aged and/or damaged tissues.

Certain exemplary embodiments described herein relate to novel compositions and/or methods adapted for promoting tissue repair and regeneration. Certain exemplary methods described herein provide for systemic administration of an exemplary composition to the mammal after tissue injury. The composition can comprise one or more peptide-conjugated biotin molecules adapted to stimulate mitochondrial cellular ATP production to promote cell proliferation and/or tissue regeneration. The composition can include vitamins and/or amino acids and/or metabolic supplements in effective concentrations that exhibit additive or synergistic activity in maintaining tissue health.

Tissue injury can include injury to skin, and/or soft tissues (e.g., muscles, tendons, ligaments, nerves, blood vessels), and/or hard tissues (e.g., bones, teeth), and/or solid organs (e.g., heart, kidneys, lungs, liver, spleen, intestines, etc.). The cause of tissue injury can include, e.g., trauma, hypoxia (i.e., low oxygen supply), ischemia (i.e., low blood flow), infectious agents, drugs, chemicals, and/or toxins, etc.

Certain exemplary embodiments described herein relate to novel compositions and/or methods adapted for the treatment of wounds and/or tissue injury, and/or for the promotion of tissue regeneration and more rapid wound repair. Certain exemplary methods described herein provide for application of a composition directly to a wound, such as to stimulate (i.e., promote) adjacent cells in the periphery of the wound to proliferate (i.e., increase in number of cells), to facilitate and/or achieve wound closure. The composition can comprise one or more peptide-conjugated biotin molecules adapted to stimulate mitochondrial cellular ATP production to promote cell proliferation and/or migration (i.e., cell movement). The composition can include vitamins and/or supplements and/or metabolic supplements in effective concentrations that exhibit additive or synergistic activity in stimulating wound healing, such as for post-surgical wounds and/or non-healing chronic wounds, e.g., pressure ulcers and/or diabetic ulcers and/or venous ulcers in patients.

Exemplary methods described herein relate to novel compositions and/or methods adapted for the treatment of tissue injury that can promote proliferation of resident stem/progenitor cells in vivo in damaged tissues.

Certain exemplary embodiments can provide a pharmaceutical composition that can be useful in the promotion of tissue repair and/or regeneration, that composition comprising:
(a) one or more compounds that promote ATP production and cell proliferation;
(b) at least one vitamin; and/or
(c) at least one amino acid; and/or
(d) at least one metabolic supplement Certain exemplary embodiments described herein can provide a method of enhancing mitochondrial ATP production in a mammal, the method comprising administering to the mammal a therapeutically effective amount of a compound having the formula:

| | |
|---|---|
| D-Biotin-D-Arg-L-(2'6'-dimethylTyr)-L-Lys-L-Phe-NH$_2$ | (SPN05); |
| D-Biotin-D-Trp-D-Arg-D-Trp-D-Lys-OH | (SPN08); |
| D-Trp-D-Arg-D-Trp-D-Lys(biotinyl)-OH | (SPN09); |
| L-Trp-L-Arg-L-Trp-L-Lys(biotinyl)-NH$_2$ | (SPN11); |
| D-Biotin-L-Trp-L-Arg-L-Trp-L-Lys(biotinyl)-NH$_2$ | (SPN12); |
| D-Arg-L-Tyr-D-Arg-L-Phe-L-Lys(biotinyl)-NH$_2$ and/or | (SPN15); |
| D-Biotin-D-Arg-L-Tyr-D-Arg-L-Phe-L-Lys(biotinyl)-NH$_2$ | (SPN16) | wherein the compound is administered to the mammal as a composition comprising a pharmaceutically acceptable carrier.

Certain exemplary embodiments described herein can provide a composition configured for increasing cell proliferation for primary cells cultured ex vivo without serum, the composition comprising of an active ingredient that comprises one or more peptide-conjugated biotin molecules that stimulate mitochondrial ATP production and cell proliferation, and a second ingredient that compromises at least one vitamin and/or amino acid and/or metabolic supplement that potentiates ATP production and cell proliferation.

Certain exemplary embodiments described herein can provide a composition configured for increasing cell and organ survival ex vivo, the composition comprising of an active ingredient that comprises one or more peptide-conjugated biotin molecules that stimulate mitochondrial ATP production and cell proliferation, and a second ingredient that compromises at least one vitamin and/or amino acid and/or metabolic supplement that potentiates ATP production and cell proliferation.

Certain exemplary embodiments described herein can provide a composition configured for increasing cell proliferation, such as in a wound area, the composition comprising an active ingredient that comprises one or more peptide-conjugated biotin molecules and/or a second ingredient that compromises an admixture of at least one vitamin and/or one amino acid and/or one metabolic supplement that potentiates cell proliferation and migration.

Examples of amino acids that can be used with certain exemplary embodiments described herein include L-isomers of all natural amino acids including essential and nonessential amino acids (isoleucine, leucine, alanine, asparagine, lysine, aspartic acid, methionine, cysteine, phenylalanine, glutamic acid, threonine, glutamine, tryptophan, glycine, valine, proline, serine, tyrosine, arginine, histidine), as well as taurine that is naturally derived from cysteine.

Examples of metabolic supplements that can be used with certain exemplary embodiments described herein include pyruvate, carnitine, acetylcarnitine, creatine, α-ketoglutarate, α-lipoic acid, coenzyme $Q_{10}$, nicotinamide riboside, nicotinamide mononucleotide.

Certain exemplary embodiments described herein can provide a method of enhancing survival and proliferation of primary mammalian cells in serum-free, chemically-defined media by adding a formulation comprising an effective amount of one of more peptide-conjugated biotin molecules and a mixture of at least one vitamin and/or one amino acid and/or one metabolic supplement to the culture media.

In certain exemplary embodiments of one or more methods described herein, the primary cells can include bone marrow stem cells or mesenchymal stem cells for autologous, allogeneic, or xenogenic regenerative medicine applications.

In certain exemplary embodiments of one or more methods described herein, the primary cells can be stem cells obtained from placenta or umbilical cord blood for allogeneic transplant.

In certain exemplary embodiments of one or more methods described herein, the primary cells can be hematopoietic cells such as T cells for chimeric antigen receptor (CAR) T-cell therapy.

In certain exemplary embodiments of one or more methods described herein, the primary cells can be mammalian cells cultured for the production of therapeutic proteins such as monoclonal antibodies and/or biopharmaceuticals and/or in the development and/or production of viral vaccines.

In certain exemplary embodiments of one more methods described herein, the primary cells can be animal cells such as myoblasts cultured for in vitro production of laboratory-grown, slaughter-free meat.

In certain exemplary embodiments of one or more methods described herein, the primary cells can be pancreatic islet cells harvested from a donor pancreas and purified in a laboratory before transplantation.

Certain exemplary embodiments described herein can provide a method for optimizing and/or improving stem cell transplantation and/or mitochondrial transfer for tissue regeneration by treating the stem cells and/or mitochondria with a solution comprising a therapeutically effective amount of one or more peptide-conjugated biotin molecules and a mixture of at least one vitamin and/or one amino acid and/or one metabolic supplement prior to transplantation.

In certain exemplary embodiments of one or more methods described herein, the cells can be resident stem/progenitor cells in injured tissues and one or more peptide-conjugated biotin molecules and a mixture of at least one vitamin and/or one amino acid and/or one metabolic supplement can be administered systemically to the subject.

In certain exemplary embodiments of one or more methods described herein, one or more peptide-conjugated biotin molecules and at least one vitamin and/or one amino acid and/or one metabolic supplement can be administered systemically to the subject after mitochondrial transplantation to optimize survival and function of the mitochondria.

In certain exemplary embodiments of one or more methods described herein, one or more peptide-conjugated biotin molecules and at least one vitamin and/or one amino acid and/or one metabolic supplement can be added to serum-free medium for cultivation of lab-grown meat to replace livestock-derived meat.

Certain exemplary embodiments described herein can provide a method of enhancing organ preservation solutions by adding to the preservation solution a formulation comprising an effective amount of one or more peptide-conjugated biotin molecules and at least one vitamin and/or one amino acid and/or one metabolic supplement.

In certain exemplary embodiments of one or more methods described herein, the organ can include kidney, liver, heart, lungs, pancreas, skin, intestines, cornea, trachea, and/or blood vessels.

In certain exemplary embodiments of one or more methods described herein, an effective amount of one or more peptide-conjugated biotin molecules and at least one vitamin and/or one amino acid and/or one metabolic supplement can be administered systemically to the transplant recipient to improve early graft function and improve graft survival.

Certain exemplary embodiments described herein can provide a method of enhancing tissue health in a subject by administering a micronutrient formulation comprising an effective amount of one or more peptide-conjugated biotin molecules and a mixture of at least one vitamin and/or one amino acid and/or one metabolic supplement.

Certain exemplary embodiments described herein can provide a method of enhancing tissue health in a subject by administering a micronutrient formulation comprising an effective amount of one or more peptide-conjugated biotin molecules and a mixture of acetylcarnitine and/or α-ketoglutarate.

Certain exemplary embodiments described herein can provide a method of enhancing tissue health in a subject by giving a micronutrient formulation comprising an effective amount of one or more peptide-conjugated biotin molecules and a mixture of acetylcarnitine, α-ketoglutarate, and/or taurine.

In certain exemplary embodiments of one or more methods described herein, tissue health can include health of keratinous tissues (e.g. skin, hair, and/or nails), and/or muscle, and/or joints, and/or bone, and/or heart, and/or lung, and/or kidney, and/or brain, and/or vision, and/or hearing.

In certain exemplary embodiments of one or more methods described herein, the tissue injury can be caused by aging. All cells can experience changes with aging. Many cells can lose their ability to function, waste products can accumulate in cells, connective tissues can become stiff, and many tissues can lose mass.

Certain exemplary embodiments described herein can provide a method of reducing, mitigating, and/or reversing age-related injury in a subject by administering a composition comprising an effective amount of one or more peptide-conjugated biotin molecules and at least one vitamin and/or one amino acid and/or one metabolic supplement, that administration occurring orally, sublingually, and/or subcutaneously, etc. A pharmaceutical preparation for oral administration can be a solution, suspension, or solid forms, such as tablets, capsules, and powders, etc. A pharmaceutical preparation for sublingual administration or for subcutaneous injection can be prepared by mixing such a composition with non-toxic, therapeutically-inert, and/or liquid carriers customarily used in sublingual and/or subcutaneous preparations.

Certain exemplary embodiments described herein can provide a method of enhancing skin wound healing in a subject by administering a topical solution comprising a therapeutically effective amount of one or more peptide-conjugated biotin molecules and at least one vitamin and/or one amino acid and/or one metabolic supplement directly to the wound area.

Certain exemplary embodiments described herein can provide a method of enhancing skin wound healing in a subject by giving a topical solution compromising a therapeutically effective amount of one of more peptide-conjugated biotin molecules and taurine directly to the wound area.

In certain exemplary embodiments of one or more methods described herein, the wound can be pressure wound, surgical wound, burn wound, trauma, and/or wounds that have been exposed to one or more chemicals and/or therapeutic radiation, etc.

For topical administration to the skin, certain exemplary compositions described herein can be prepared as a spray, ointment, cream, and/or gel. A pharmaceutical preparation for topical administration to the skin can be prepared by mixing such a composition with non-toxic, therapeutically-inert, solid, and/or liquid carriers customarily used in topically-administered pharmaceutical preparations.

Certain exemplary embodiments described herein can provide a method of enhancing gingival and/or periodontal healing in a subject by administering a topical solution comprising a therapeutically effective amount of one or more peptide-conjugated biotin molecules and at least one vitamin and/or one amino acid and/or one metabolic supplement directly to the wound area.

Certain exemplary embodiments described herein can provide a method of enhancing gingival and/or periodontal healing in a subject by administering a topical solution comprising a therapeutically effective amount of one or more peptide-conjugated biotin molecules and taurine.

For topical administration to the oral mucosal membrane, certain exemplary compositions described herein can be prepared as a spray, ointment, gel, mouth wash, and/or toothpaste, etc. A pharmaceutical preparation for topical administration to the mucosal membrane can be prepared by mixing such a composition with non-toxic, therapeutically-inert, and/or liquid carriers customarily used in topically-administered pharmaceutical preparations.

Certain exemplary embodiments described herein can provide a method of enhancing repair to injuries of the eye in a subject by administering, directly to the eye, a topical solution comprising a therapeutically effective amount of one or more peptide-conjugated biotin molecules and at least one vitamin and/or one amino acid and/or one metabolic supplement.

Certain exemplary embodiments described herein can provide a method of enhancing repair to injuries of the eye in a subject by administering a topical solution comprising a therapeutically effective amount of one or more peptide-conjugated biotin molecules and taurine.

In certain exemplary embodiments of one or more methods described herein, the injury to the eye can be one or more of, e.g., acute corneal abrasion, subconjunctival hemorrhages, and/or retinal detachment, etc., and/or chronic eye diseases including, e.g., age-related macular degeneration, diabetic retinopathy, glaucoma, and/or dry eye disease, etc.

Certain exemplary embodiments can provide a method of enhancing bone and soft tissue healing in a subject by administering a solution comprising a therapeutically effective amount of one or more peptide-conjugated biotin molecules and at least one vitamin and/or one amino acid and/or one metabolic supplement directly to the wound area.

In certain exemplary embodiments of one or more methods described herein, the injury can be acute and/or chronic, such as trauma, arthritis, tendinitis, one or more ligament tears, and/or nerve compression, etc.

For direct application to soft tissues, certain exemplary compositions described herein can be prepared as a sterile solution for injection into one or more joints, tendons, muscles, and/or nerves, etc. A pharmaceutical preparation for injection can be prepared by mixing such a composition with non-toxic, therapeutically-inert, and/or liquid carriers customarily used in such preparations, such as polyethyleneglycol and hyaluronic acid.

Certain exemplary embodiments described herein can provide a method of enhancing organ repair in a subject by administering a solution comprising a therapeutically effective amount of one or more peptide-conjugated biotin molecules and at least one vitamin and/or one amino acid and/or one metabolic supplement, such as intravenously, intramuscularly, subcutaneously, and/or orally, etc. A pharmaceutical preparation for injection can be prepared by mixing such a composition with non-toxic, therapeutically-inert, and/or liquid carriers customarily used in injectable pharmaceutical preparations. A pharmaceutical preparation for oral administration can be administered as, e.g., a solution, suspension, and/or solid form, such as one or more tablets, capsules, and/or powders, etc.

In certain exemplary embodiments of one or more methods described herein, the tissue injury can be caused by acute diseases, e.g., trauma, reduced blood flow, reduced oxygen supply, infectious agents, drugs, and/or toxins to one or more organs, structures, and/or systems, such as the heart, brain, kidney, liver, intestines, and/or limbs, etc.

In certain exemplary embodiments of one or more methods described herein, the tissue injury can be caused by chronic diseases, e.g., heart failure, chronic kidney disease, inflammatory bowel disease, diabetic complications, stroke, macular degeneration, and/or neurodegenerative diseases including Parkinson's Disease, Amyotropic Lateral Sclerosis, Huntington's Disease, Chronic Traumatic Encephalopathy, and/or Alzheimer's Disease, etc.

In certain exemplary embodiments of one or more methods described herein, a mixture of one or more peptide-conjugated biotin molecules can be administered to a subject with progressive multiple sclerosis, frontotemporal dementia, Parkinson's disease, and/or Alzheimer's disease.

In certain exemplary embodiments of one or more methods described herein, a mixture of one or more peptide-conjugated biotin molecules and thiamine can be administered to a subject with biotin-thiamine-responsive basal ganglia disease.

In certain exemplary embodiments of one or more methods described herein, a mixture of one or more peptide-conjugated biotin molecules can be administered to a subject with inflammatory bowel disease.

Example 1—Short Aromatic-Cationic Peptide Sequences Increase Cellular Uptake of Biotin Certain peptide sequences described herein can be water-soluble polypeptides composed of 4 to 6 amino acids that can have a general aromatic-cationic motif, meaning that the peptide sequence can be, e.g., [aromatic-cationic-aromatic-cationic] or [cationic-aromatic-cationic-aromatic].

Certain "short" peptide sequences described herein can be polypeptides composed of a minimum of four amino acids and a maximum of six amino acids.

The amino acids can be naturally occurring. Naturally occurring amino acids include the twenty most common amino acids normally found in proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Aromatic amino acids can include Phe, Tyr, and Trp. Cationic amino acids can include Lys, Arg, and His. The amino acids can include the natural amino acids in the D-configuration. In certain peptides, the carboxyl terminus can be amidated.

The amino acids can be non-naturally occurring. Non-naturally occurring amino acids are those amino acids that typically are not synthesized in normal metabolic processes in living organisms, and do not naturally occur in proteins. Non-naturally occurring amino acids can include derivatives of naturally occurring amino acids, in either L- or D-configuration.

Certain exemplary embodiments can provide for administering to the subject a composition for therapeutic purposes. In certain exemplary therapeutic applications, compositions and/or medicaments can be administered to a subject suspected of, or already suffering from, such a disease and/or condition in an amount sufficient to cure, or at least partially arrest, the symptoms of the disease and/or condition, including its complications and intermediate pathological phenotypes in development of the disease and/or condition.

In certain exemplary embodiments, therapeutic methods comprise administration of the composition in conjunction with one or more active agents. In certain exemplary embodiments, peptide administration is chronic.

In certain exemplary embodiments the peptide can be administered in conjunction with one or more thrombolytic agents. In certain exemplary embodiments, the one or more thrombolytic agents can be selected from the group consisting of: tissue plasminogen activator, urokinase, prourokinase, streptokinase, acylated form of plasminogen, acylated form of plasmin, and acylated streptokinase-plasminogen complex.

In certain exemplary embodiments, therapeutic methods can comprise administration of the composition in conjunction with one or more antihypertensive agents. In certain exemplary embodiments, the one or more antihypertensive agents can comprise diuretics, adrenergic receptor antagonists, calcium channel blockers, renin inhibitors, angiotensin converting enzyme (ACE) inhibitors, angiotensin II receptor antagonists, aldosterone antagonists, vasodilators, and/or alpha-2 agonists.

In certain exemplary embodiments, the diuretics can comprise loop diuretics, thiazide diuretics, thiazide-like diuretics, and/or potassium-sparing diuretics. In certain exemplary embodiments, the diuretics can comprise bumetanide, ethacrynic acid, furosemide, torsemide, epitizide, hydrochlorothiazide, chlorothiazide, bendroflumethiazide, indapamide, chlorthalidone, metolazone, amiloride, triamterene, and/or spironolactone.

In certain exemplary embodiments, the adrenergic receptor antagonists can comprise beta blockers, alpha blockers, or mixed alpha and beta blockers. In certain exemplary embodiments, the adrenergic receptor antagonists can comprise atenolol, metoprolol, nadolol, oxprenolol, pindolol, propranolol, timolol, doxazosin, phentolamine, indoramin, phenoxybenzamine, prazosin, terazosin, tolazoline, bucindolol, carvedilol, and/or labetalol.

In certain exemplary embodiments, the calcium channel blockers can comprise dihydropyridines and/or non-dihydropyridines. In certain exemplary embodiments, the calcium channel blockers can comprise amlodipine, felodipine, isradipine, lercanidipine, nicardipine, nifedipine, nimodipine, nitrendipine, diltiazem, and/or verapamil.

In certain exemplary embodiments, the renin inhibitors can comprise Aliskiren®.

In certain exemplary embodiments, the angiotensin converting enzyme (ACE) inhibitors can comprise captopril, enalapril, fosinopril, lisinopril, perindopril, quinapril, ramipril, trandolapril, and/or benazepril.

In certain exemplary embodiments, the angiotensin II receptor antagonists can comprise Irbesartan®.

In certain exemplary embodiments, the aldosterone antagonists can comprise eplerenone and/or spironolactone.

In certain exemplary embodiments, the vasodilators antagonists can comprise sodium nitroprusside and/or hydralazine.

In certain exemplary embodiments, the alpha-2 agonists antagonists can comprise clonidine, guanabenz, methyldopa, moxonidine, guanethidine, and/or reserpine.

In certain exemplary embodiments, any method known to those in the art for contacting a cell, organ, and/or tissue with a peptide can be employed. Suitable methods can include in vitro, ex vivo, and/or in vivo methods. When used in vivo for therapy, the compositions can be administered to the subject in effective amounts (i.e., amounts that have desired therapeutic effect). The dose and dosage regimen can depend upon the degree of the injury in the subject, the characteristics of the particular composition used, e.g., its therapeutic index, the subject, and/or the subject's history.

The effective amount can be determined during pre-clinical trials and/or clinical trials by methods familiar to physicians and/or clinicians. An effective amount of a peptide useful in the methods can be administered to a mammal in need thereof by any of a number of well-known methods for administering pharmaceutical compounds. The peptide can be administered systemically and/or locally.

The peptide may be formulated as a pharmaceutically acceptable salt. Pharmaceutically acceptable salts can be derived from pharmaceutically acceptable inorganic or organic bases and from pharmaceutically acceptable inorganic or organic acids. When a peptide contains both a basic moiety, such as an amine, pyridine or imidazole, and an acidic moiety such as a carboxylic acid or tetrazole, zwitterions can be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic, and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt or a trifluoroacetate salt.

The compositions described herein, or pharmaceutically acceptable salts thereof, such as acetate salt or trifluoroacetate salt, can be incorporated into pharmaceutical compositions for administration, singly or in combination, to a subject for the treatment and/or prevention of a disorder described herein. Such compositions can include the active agent and a pharmaceutically acceptable carrier, which can include one or more of saline, solvents, dispersion media, coatings, antibacterial and antifungal agents, isotonic and absorption delaying agents, and the like, compatible with pharmaceutical administration. Supplementary active compounds also can be incorporated into certain exemplary compositions.

Pharmaceutical compositions can be formulated to be compatible with its intended route of administration. Exemplary routes of administration include parenteral (e.g., intravenous, intradermal, intraperitoneal or subcutaneous), oral, sublingual, nasal, inhalation, transdermal (topical), intraocular, iontophoretic, and transmucosal administration. Solutions or suspensions used for parenteral, intradermal, or subcutaneous application can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates; and agents for the adjustment of tonicity such as sodium chloride or dextrose. In certain exemplary embodiments, pH can be adjusted with acids or bases, such as hydrochloric acid or sodium hydroxide. The parenteral preparation can be enclosed in ampoules, disposable syringes, and/or multiple dose vials made of glass and/or plastic. For convenience of the patient and/or treating physician, the dosing formulation can be provided in a kit containing any or all necessary equipment (e.g., vials of drug, vials of diluent, syringes, and/or needles, etc.) for a treatment course (e.g., 7 days of treatment).

Pharmaceutical compositions suitable for injectable use can include sterile aqueous solutions (where water soluble) and/or dispersions and/or sterile powders for the extemporaneous preparation of sterile injectable solutions and/or dispersion. For intravenous administration, suitable carriers can include physiological saline, bacteriostatic water, Cremophor EL™ (BASF, Parsippany, N.J.), and/or phosphate buffered saline (PBS). A composition for parenteral administration can be sterile and/or can be fluid for easy syringability. Certain exemplary compositions can be stable under the conditions of manufacture and/or storage and/or can be preserved against the contaminating action of microorganisms such as bacteria and/or fungi.

The composition compositions can include a carrier, which can be a solvent or dispersion medium containing, for example, water, ethanol, polyol (for example, glycerol, propylene glycol, and/or liquid polyethylene glycol, and the like), and suitable mixtures thereof. The proper fluidity can be maintained, for example, by the use of a coating such as lecithin, by the maintenance of the required particle size in the case of dispersion, and/or by the use of surfactants. Prevention of the action of microorganisms can be achieved by various antibacterial and/or antifungal agents, for example, parabens, chlorobutanol, phenol, ascorbic acid, and the like. Glutathione and/or other antioxidants can be included to prevent oxidation. Certain exemplary compositions can include isotonic agents, for example, sugars and/or polyalcohols such as mannitol, sorbitol, and/or sodium chloride. Prolonged absorption of the injectable compositions can be brought about by including in the composition an agent that delays absorption, such as aluminum monostearate and/or gelatin.

Sterile injectable solutions can be prepared by incorporating the active compound in the required amount in an appropriate solvent with one or a combination of ingredients enumerated above, as required, followed by filtered sterilization. Dispersions can be prepared by incorporating the active compound into a sterile vehicle that contains a basic dispersion medium and other desired ingredients, such as one or more of those enumerated above. In the case of sterile powders for the preparation of sterile injectable solutions, exemplary methods of preparation include vacuum drying and/or freeze drying, which can yield a powder of the active ingredient plus any additional desired ingredient from a previously sterile-filtered solution thereof.

Oral compositions can include an inert diluent and/or an edible carrier. For the purpose of oral therapeutic administration, the active compound can be incorporated with excipients and/or used in the form of tablets, troches, or capsules, e.g., gelatin capsules and/or powder dissolvable in a diluent such as water. Oral compositions can be prepared using a fluid carrier for use as a mouthwash. Pharmaceutically compatible binding agents and/or adjuvant materials can be included as part of the composition. Exemplary tablets, pills, capsules, troches and the like can contain any of the following ingredients, or compounds of a similar nature: a binder such as microcrystalline cellulose, gum tragacanth, and/or gelatin; an excipient such as starch and/or lactose, a disintegrating agent such as alginic acid, Primogel, and/or corn starch; a lubricant such as magnesium stearate and/or Sterotes; a glidant such as colloidal silicon dioxide; a sweetening agent such as sucrose and/or saccharin; or a flavoring agent such as peppermint, methyl salicylate, and/or orange flavoring; etc.

For administration by inhalation, the compounds can be delivered in the form of an aerosol spray from a pressurized container and/or dispenser that contains a suitable propellant, e.g., a gas such as carbon dioxide, and/or a nebulizer.

Systemic administration of a therapeutic compound as described herein can be by transmucosal and/or transdermal means. For transmucosal or transdermal administration, penetrants appropriate to the barrier to be permeated can used in the formulation. Such penetrants can include, for example, for transmucosal administration, detergents, bile salts, and/or fusidic acid derivatives. Transmucosal administration can be accomplished through the use of nasal sprays. For transdermal administration, the active compounds can be formulated into ointments, salves, gels, and/or creams. In certain exemplary embodiments, transdermal administration can be performed by iontophoresis, microneedles, and/or electroporation.

A therapeutic protein and/or peptide can be formulated in a carrier system. The carrier can be a colloidal system. The colloidal system can be a liposome and/or a phospholipid bilayer vehicle. In certain exemplary embodiments, the therapeutic peptide can be encapsulated in a liposome while maintaining peptide integrity. An active agent can be loaded into a particle prepared from pharmaceutically acceptable ingredients including, but not limited to, soluble, insoluble, permeable, impermeable, biodegradable, and/or gastroretentive polymers and/or liposomes. Such particles can include nanoparticles, biodegradable nanoparticles, microparticles, biodegradable microparticles, nanospheres, biodegradable nanospheres, microspheres, biodegradable microspheres, capsules, emulsions, liposomes, micelles, and/or viral vector systems.

The carrier can be a polymer, e.g., a biodegradable and/or biocompatible polymer matrix. In certain exemplary embodiments, the therapeutic peptide can be embedded in the polymer matrix, while maintaining protein integrity. The polymer can be natural, such as polypeptides, proteins, or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In certain exemplary embodiments, the polymer can be poly-lactic acid (PLA) and/or copoly lactic/glycolic acid (PGLA). The polymeric matrices can be prepared and/or isolated in a variety of forms and/or sizes, including microspheres and nanospheres. Polymer formulations can lead to prolonged duration of therapeutic effect.

In certain exemplary embodiments, the therapeutic compounds can be prepared with carriers that will protect the therapeutic compounds against rapid elimination from the body, such as a controlled release formulation, including implants and microencapsulated delivery systems. Biodegradable and/or biocompatible polymers can be used, such as ethylene vinyl acetate, polyanhydrides, polyglycolic acid, collagen, polyorthoesters, and/or polylacetic acid, etc. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can be used as pharmaceutically acceptable carriers.

The therapeutic compounds can be formulated to enhance intracellular delivery. For example, liposomal delivery systems and/or fusogenic liposomes can be used to deliver a protein to cells in vivo and/or in vitro.

Dosage, toxicity, and therapeutic efficacy of the therapeutic agents can be determined by standard pharmaceutical procedures in cell cultures and/or experimental animals, e.g., for determining the LD50 (the dose lethal to 50% of the population) and/or the ED50 (the dose therapeutically effective in 50% of the population). The dose ratio between toxic and therapeutic effects, which is called the "therapeutic index", can be expressed as the ratio LD50/ED50. Compounds that exhibit high therapeutic indices can be preferred. While compounds that exhibit toxic side effects can be used, care can be taken to design a delivery system that targets such compounds to the site of affected tissue in order to minimize potential damage to uninfected cells and, thereby, reduce side effects.

The data obtained from the cell culture assays and/or animal studies can be used in formulating a range of dosage for use in humans. The dosage of such compounds can be within a range of circulating concentrations that includes the ED50 with little or no toxicity. The dosage can vary within this range depending upon the dosage form employed and/or the route of administration utilized. For certain exemplary compounds, the therapeutically effective dose can be estimated initially from cell culture assays. A dose can be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

An effective amount of the compositions, sufficient for achieving a therapeutic or prophylactic effect, can range from about 0.000001 mg per kilogram body weight per day to about 10,000 mg per kilogram body weight per day. The dosage ranges can be from about 0.0001 mg per kilogram body weight per day to about 100 mg per kilogram body weight per day. As examples, dosages can be about 1 mg/kg body weight or about 10 mg/kg body weight every day, every two days, or every three days or within the range of about 1 to about 10 mg/kg every week, every two weeks, or every three weeks. In certain exemplary embodiments, a single dosage of peptide can range from about 0.1 to about 10,000 micrograms per kg body weight. In certain exemplary embodiments, composition concentrations in a carrier range from about 0.2 to about 2000 micrograms per delivered milliliter can be administered. An exemplary treatment regime can entail administration once per day or once a week. In certain therapeutic applications, a relatively high dosage at relatively short intervals can be required until progression of the disease is reduced and/or terminated, and/or until the subject shows partial or complete amelioration of symptoms of disease. Thereafter, the patient can be administered a prophylactic regime.

In certain exemplary embodiments, a therapeutically effective amount of a composition can be defined as a concentration of peptide at the target tissue of about $10^{-12}$ to $10^{-6}$ about molar, e.g., approximately $10^{-7}$ molar. This concentration can be delivered by systemic doses of about 0.01 to about 100 mg/kg or equivalent dose by body surface area. The schedule of doses can be optimized to maintain the therapeutic concentration at the target tissue, such as by single daily or weekly administration, but also including continuous administration (e.g., parenteral infusion and/or transdermal application).

In certain exemplary embodiments, the dosage of the composition can be provided at a "low," "mid," or "high" dose level. In certain exemplary embodiments, the low dose can be provided from about 0.01 to about 0.5 mg/kg/h, such as from about 0.0001 to about 0.1 mg/kg/h. In certain exemplary embodiment, the mid-dose can provided from about 0.001 to about 1.0 mg/kg/h, such as from about 0.01 to about 0.5 mg/kg/h. In certain exemplary embodiments, the high dose can be provided from about 0.005 to about 10 mg/kg/h, such as from about 0.01 to about 2 mg/kg/h.

In certain exemplary embodiments, certain factors can influence the dosage and/or timing required to effectively treat a subject, including but not limited to, the severity of the disease or disorder, previous treatments, the general health and/or age of the subject, and/or other diseases present. Moreover, treatment of a subject with a therapeutically effective amount of the therapeutic compositions described herein can include a single treatment or a series of treatments.

The mammal treated in accordance with certain exemplary methods can be any mammal, including, for example, farm animals, such as sheep, pigs, cows, and horses; pet animals, such as dogs and cats; and/or laboratory animals, such as rats, mice, and rabbits. In certain exemplary embodiments, the mammal can be a human.

Certain exemplary embodiments provide for a biologically active composition of matter comprising a first D-biotin conjugated to a lysine located at the C-terminus of a water-soluble, cell-permeable, mitochondria-targeted peptide sequence, wherein:

the mitochondria-targeted peptide sequence comprises a minimum of four amino acids and a maximum of six amino acids;

the mitochondria-targeted peptide sequence has a general alternating aromatic-cationic motif;

the mitochondria-targeted peptide sequence is selected from:

D-Arg-L-(2'6'-dimethylTyr)-L-Lys-L-Phe-NH₂;

D-Arg-L-Tyr-D-Arg-L-Phe-L-Lys-NH₂;

D-Trp-D-Arg-D-Trp-D-Lys-OH;

(SEQ ID NO: 2)
L-Trp-L-Arg-L-Trp-L-Lys-NH₂;

D-Trp-D-Arg-D-Trp-D-Lys-NH₂;
and/or (SEQ ID NO: 1)
L-Trp-L-Arg-L-Trp-L-Lys-OH;

a second D-biotin is conjugated to an N-terminus α-amine of the mitochondria-targeted peptide sequence;

the composition comprises one or more of:
D-Biotin-D-Arg-L-(2'6'-dimethylTyr)-L-Lys-L-Phe-NH₂; and
D-Biotin-D-Trp-D-Arg-D-Trp-D-Lys-OH;

the first D-biotin is conjugated to an ε-amine of the lysine at a C-terminus of the mitochondria-targeted peptide sequence;

the composition comprises one or more of:
D-Trp-D-Arg-D-Trp-D-Lys(biotinyl)-OH;
L-Trp-L-Arg-L-Trp-L-Lys(biotinyl)-NH₂; and
D-Arg-L-Tyr-D-Arg-L-Phe-L-Lys(biotinyl)-NH₂;

the first D-biotin is conjugated to an ε-amine of the lysine at the C-terminus of the mitochondria-targeted peptide sequence and a second D-biotin is conjugated to an N-terminus α-amine; and/or the composition comprises one or more of:
D-Biotin-L-Trp-L-Arg-L-Trp-L-Lys(biotinyl)-NH₂; and
D-Biotin-D-Arg-L-Tyr-D-Arg-L-Phe-L-Lys(biotinyl)-NH₂.

Certain exemplary embodiments provide for a biologically active composition of matter comprising a first D-biotin conjugated to a lysine located at the N-terminus of a water-soluble, cell-permeable, mitochondria-targeted peptide sequence, wherein the mitochondria-targeted peptide sequence:

comprises a minimum of four amino acids and a maximum of six amino acids; and has a general alternating aromatic-cationic motif.

Certain exemplary embodiments provide for a composition of matter, comprising:

a therapeutically effective formulation comprising:
one or more biologically active, water-soluble, cell-permeable, mitochondria-targeted compounds selected from a biotinylated polypeptide group;
a pharmaceutically acceptable carrier for each of the one or more biologically active, water-soluble, cell-permeable, mitochondria-targeted compounds;
one or more vitamins selected from:
vitamin B1 (thiamine);
vitamin B2 (riboflavin);

vitamin B3 (niacin, niacinamide);
vitamin B5 (pantothenic acid);
vitamin B6 (pyridoxine);
vitamin B7 (biotin);
vitamin B9 (folate);
vitamin B12 (cyanocobalamine); and
vitamin C (ascorbic acid);
one or more metabolic supplements selected from:
pyruvate;
carnitine;
acetylcarnitine;
creatine;
a-ketoglutarate;
a-lipoic acid;
coenzyme Q;
nicotinamide riboside; and
nicotinamide mononucleotide; and/or
one or more amino acids selected from:
leucine;
isoleucine;
valine;
glutamine;
serine;
arginine;
methionine;
tryptophan;
glycine;
trimethylglycine;
b-hydroxy-b-methylbutyrate; and
Taurine;
wherein:
each biologically active, water-soluble, cell-permeable, mitochondria-targeted compound in the biotinylated polypeptide group is defined by:
a plurality of amino acids arranged with a general alternating aromatic-cationic motif;
a minimum of four amino acids and a maximum of six amino acids;
a first D-biotin conjugated to a lysine located at the C-terminus or the N-terminus of that biotinylated polypeptide;
the biotinylated polypeptide group consists of:
D-Biotin-D-Arg-L-(2'6'-dimethylTyr)-L-Lys-L-Phe-NH$_2$;
D-Biotin-D-Trp-D-Arg-D-Trp-D-Lys-OH;
D-Trp-D-Arg-D-Trp-D-Lys(biotinyl)-OH;
L-Trp-L-Arg-L-Trp-L-Lys(biotinyl)-NH$_2$;
D-Arg-L-Tyr-D-Arg-L-Phe-L-Lys(biotinyl)-NH$_2$;
D-Biotin-L-Trp-L-Arg-L-Trp-L-Lys(biotinyl)-NH$_2$; and
D-Biotin-D-Arg-L-Tyr-D-Arg-L-Phe-L-Lys(biotinyl)-NH$_2$.

TABLE 1 identifies certain exemplary short, water-soluble, alternating aromatic-cationic peptide sequences.

The alternating aromatic-cationic peptide sequences useful in certain exemplary methods described herein can be chemically synthesized by any of the methods described in the following US patent documents, each of which is incorporated by reference herein in its entirety and/or for its portion that describes or is relevant to synthesizing peptides and/or using synthesized peptides:

U.S. Pat. No. 4,749,742;
U.S. Pat. No. 5,026,773;
U.S. Pat. No. 7,576,061;
U.S. Pat. No. 9,388,212;
U.S. Pat. No. 9,695,214;
U.S. patent Ser. No. 10/125,163;
US Patent Application Publication 2019/0202861;
US Patent Application Publication 2019/0015521; and
US Patent Application Publication 2012/0149868.

Certain exemplary alternating aromatic-cationic peptide sequences listed in Table 1 are water-soluble.

Certain exemplary alternating aromatic-cationic peptide sequences listed in Table 1 are water-soluble but can penetrate cell membranes.

Certain exemplary alternating aromatic-cationic peptide sequences listed in Table 1 are water-soluble but can penetrate mitochondrial outer membranes.

Figure 1B:
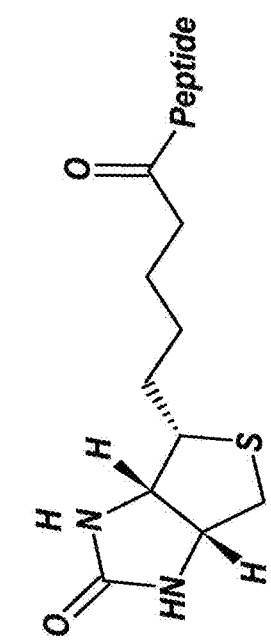
Figure 1C:
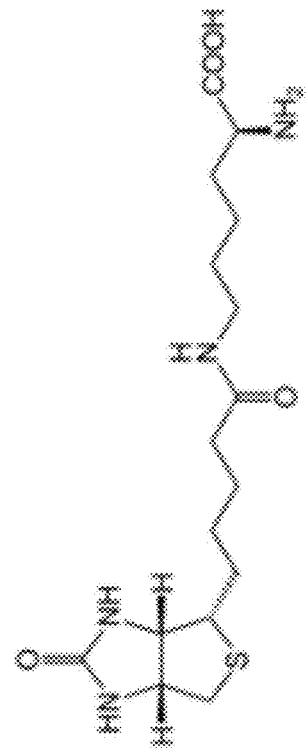

Biotin (FIG. 1A) can be conjugated to the alternating aromatic-cationic peptide sequences at the N-terminus α-amine (FIG. 1B) or the ε-amino group of lysine at the C-terminus (FIG. 1C).

For certain exemplary embodiments, via chemically synthesis, biotin can be conjugated to the polypeptide using one or more methods described in any of the following U.S. patent publications, each of which is incorporated by reference herein in its entirety and for its teachings of such methods:

U.S. Pat. No. 5,391,711;
U.S. Pat. No. 5,416,016; and
U.S. Patent Application Publication: 2006/0149035.

Certain exemplary embodiments can preferentially label the α-amino N-terminus in peptides with biotin. In certain exemplary embodiments, biotinylation can be readily accomplished by activating the carboxyl group of biotin such that it reacts with free amino groups of the peptide. Certain exemplary embodiments can a biotinylating reagent such as D-biotin-N-hydroxy-succinimide ester or biotinyl-p-nitrophenyl ester can be used. The activated ester can react under mild conditions with amino groups to incorporate a biotin residue into the desired molecule. Certain exemplary embodiments can biotinylate macromolecules using D-biotin-N-hydroxy-succinimide ester and/or can biotinylate an exogenous molecule using biotinyl-ε-nitrophenyl ester as a biotinylating reagent. Other reagents such as D-biotinyl-ε-aminocaproic acid N-hydroxy-succinimide ester in which

TABLE 1

| | | | | | | | |
|---|---|---|---|---|---|---|---|
| SS-31 | D-Arg | L-2'6'dimethylTyr | L-Lys | L-Phe | | NH$_2$ | |
| SPN02 | D-Arg | L-Tyr | D-Arg | L-Phe | L-Lys | NH$_2$ | |
| SPN07 | D-Trp | D-Arg | D-Trp | D-Lys | | OH | |
| SPN10 | L-Trp | L-Arg | L-Trp | L-Lys | | NH$_2$ | (SEQ ID NO: 1) |
| SPN13 | D-Trp | D-Arg | D-Trp | D-Lys | | NH$_2$ | |
| SPN14 | L-Trp | L-Arg | L-Trp | L-Lys | | OH | (SEQ ID NO: 2) |

ε-aminocaproic acid serves as a spacer link to reduce steric hindrance can also be used by certain exemplary embodiments.

For certain exemplary embodiments, biotinylation can be performed at the ε-amino group lysine to form biocytin. In certain exemplary embodiments, biocytin-containing peptides can be achieved via solid phase synthesis using Fmoc-Lys(ε-biotinyl) at the C-terminal position, which can result in Lys(biotinyl) or biocytin after undergoing acid cleavage of the resin. For example, to create biocytin, certain exemplary embodiments can utilize one or more methods described in U.S. Pat. No. 2,720,527, which is incorporated by reference herein in its entirety And for its teachings of such methods.

Certain exemplary peptide-conjugated biotin molecules and the corresponding mitochondria-targeting peptide sequences are listed in TABLE 2.

TABLE 2

| | | | | | | |
|---|---|---|---|---|---|---|
| SS-31 | | D-Arg | L-2'6'dimethylTyr | L-Lys | L-Phe | $NH_2$ |
| SPN05 | biotin | D-Arg | L-2'6'dimethylTyr | L-Lys | L-Phe | $NH_2$ |
| SPN07 | | D-Trp | D-Arg | D-Trp | D-Lys | OH |
| SPN08 | biotin | D-Trp | D-Arg | D-Trp | D-Lys | OH |
| SPN09 | | D-Trp | D-Arg | D-Trp | D-Lys(bio) | OH |
| SPN10 | | L-Trp | L-Arg | L-Trp | L-Lys | $NH_2$ (SEQ ID NO: 1) |
| SPN11 | | L-Trp | L-Arg | L-Trp | L-Lys(bio) | $NH_2$ |
| SPN12 | biotin | L-Trp | L-Arg | L-Trp | L-Lys(bio) | $NH_2$ |
| SPN02 | | D-Arg | L-Tyr | D-Arg | L-Phe | L-Lys | $NH_2$ |
| SPN15 | | D-Arg | L-Tyr | D-Arg | L-Phe | L-Lys(bio) | $NH_2$ |
| SPN16 | biotin | D-Arg | L-Tyr | D-Arg | L-Phe | L-Lys(bio) | $NH_2$ |

Cellular uptake and localization of peptide-conjugated biotin molecules were determined in HK-2 human renal epithelial cells and ARPE-19 human retinal pigment epithelial cells (ATCC, Manassas, Va.). HK-2 cells were cultured in Dulbecco's Modified Eagle's Medium (DMEM) containing 1 g/L glucose and 10% fetal bovine serum (FBS), 100 units/ml penicillin and 100 ug/ml streptomycin. ARPE-19 cells were cultured in DMEM/F12 medium containing 1 g/L glucose and 10% fetal bovine serum (FBS), 100 units/ml penicillin and 100 ug/ml streptomycin. Cells were incubated in humidified incubator with 5% CO2 at 37° C. HK-2 cells and ARPE-19 cells were seeded in 35 mm dish at an initial density of $5\times10^4$ cells. FBS was removed from the culture medium for 3 days to deplete endogenous biotin in the cells. Cells were then incubated in serum-free media containing biotin or peptide-conjugated biotin molecules for 12-hours (HK-2 cells) or 1-hour (ARPE-19 cells). All compounds were used at 1 uM.

Biotin uptake was determined using Streptavidin binding. Streptavidin has high affinity for biotin. By using Alexa Fluor 594-conjugated streptavidin, it is possible to visualize biotin uptake using fluorescence microscopy. Cells were fixed with 4% PFA for 10 min at RT, permeabilized in 0.1% triton X-100/PBS for 10 min at RT and incubated with 3.2 ug/ml Streptavidin-Alexa Fluor 594 (Jackson ImmunoResearch, West Grove, Pa.) and 5 ug/ml Hoechst 33342 (Novus Biologicals, Centennial, Colo.) for 30 min at RT. Hoechst 33342 is a fluorescent stain for labeling DNA and it is used for nuclear staining. Live cell image buffer was added and Alexa-594 fluorescence (Ex/Em=591/614 nm) and Hoechst fluorescence (Ex/Em=490/461 nm) was observed using the Nikon Eclipse Ti2 fluorescence microscope (100× oil objective). Ten random fields from each sample were quantified by NIS-Elements Imaging Software (Nikon) for streptavidin fluorescence and normalized to Hoechst fluorescence to account for number of cells per field.

Figure 2:
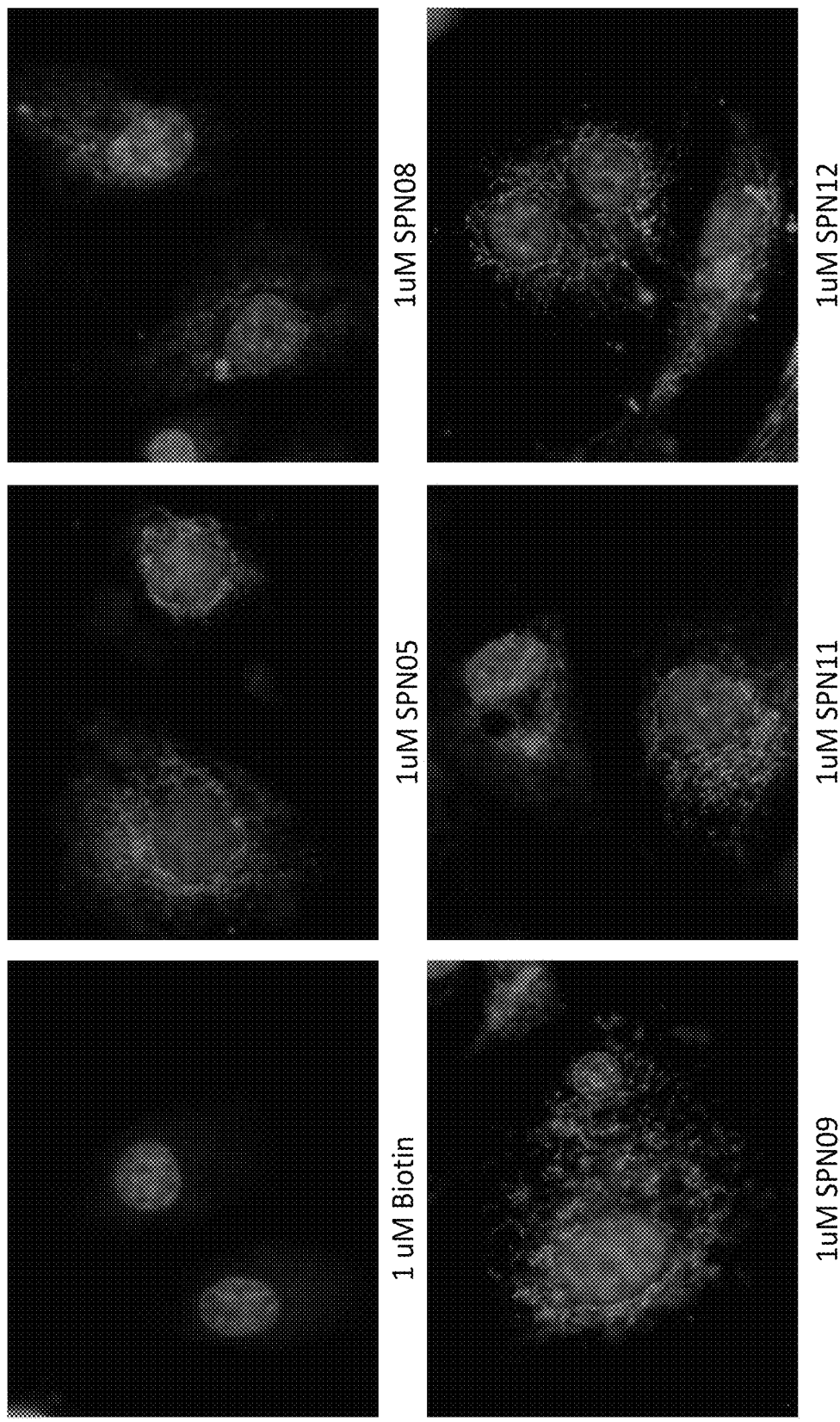
FIG. 2 are fluorescent microscopic images related to cellular uptake of certain exemplary compounds.

FIG. 2 shows representative microscopic images of HK-2 human renal epithelial cells after 12-hour incubation with 1 uM free biotin or selected peptide-conjugated biotin molecules from TABLE 2. Intracellular biotin is visualized with streptavidin-AlexaFluor594 (red fluorescence). Nuclei are visualized with Hoechst 33342 dye (blue fluorescence) (1000× magnification). Minimal intracellular streptavidin fluorescence was observed when HK-2 cells were incubated with 1 uM biotin alone. In contrast, all peptide-conjugated biotin compounds (SPN05, SPN08, SPN09, SPN11 and SPN12) showed intense red fluorescence indicating significant cellular uptake of biotin.

Figure 3:
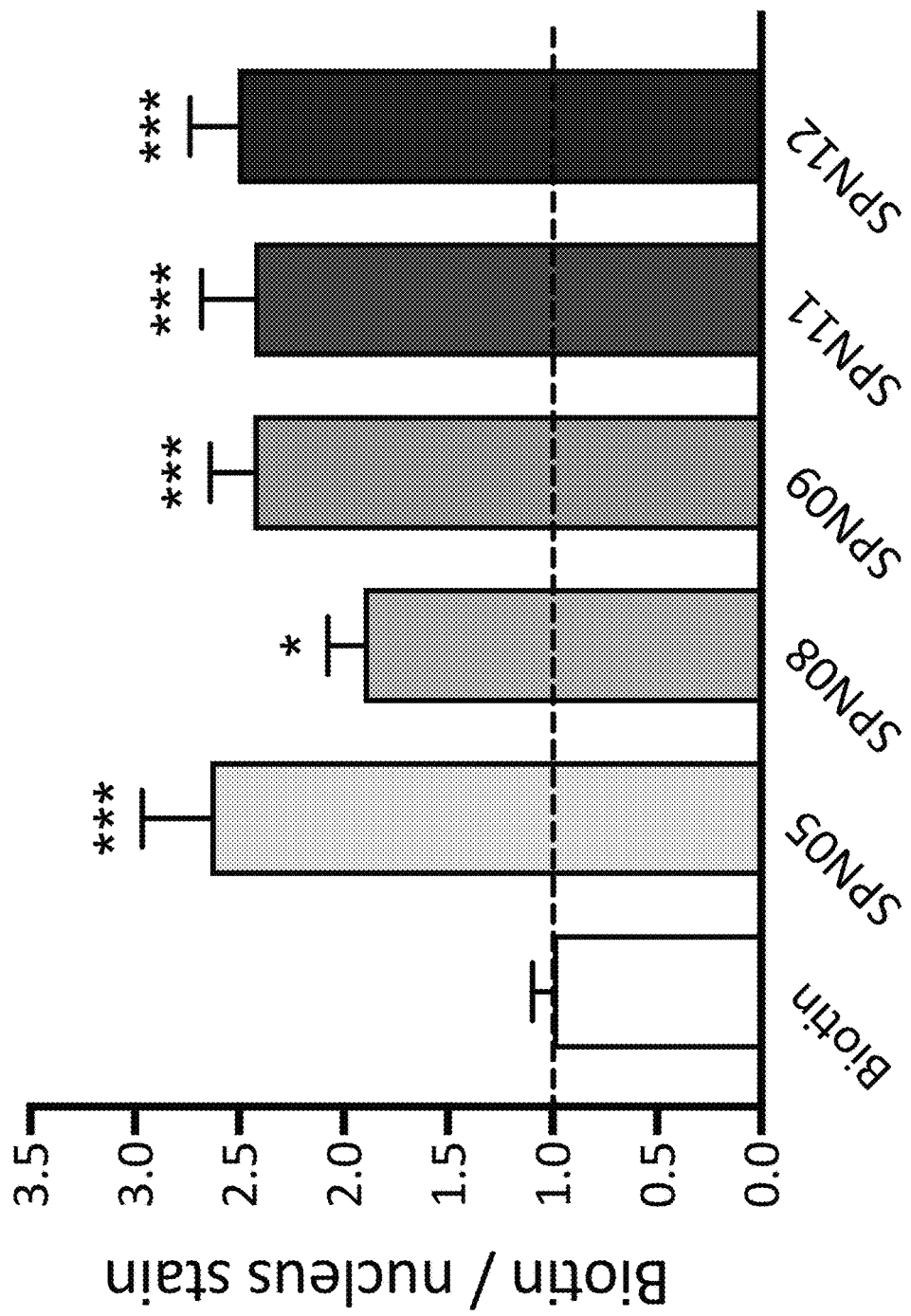
FIG. 3 is a graph showing exemplary cellular uptake.

FIG. 3 is a graph quantifying biotin uptake in HK-2 human renal epithelial cells after 12-hour incubation with 1 uM biotin or selected peptide-conjugated biotin molecules from TABLE 2. Peptide-conjugated biotin molecules delivered significantly higher intracellular biotin content compared to free biotin in HK-2 cells. Total streptavidin fluorescence normalized to cell number (Hoechst fluorescence) was calculated from 10 random fields and averaged for each treatment. All data were then normalized to treatment with free biotin, with free biotin arbitrarily set as 1.0. All peptide-conjugated biotin molecules resulted in significantly higher intracellular biotin (*$P<0.05$, ***$P<0.001$) compared to free biotin. The uptake of peptide-conjugated biotin molecules was 2 to 2.5 times higher than free biotin.

Figure 4:
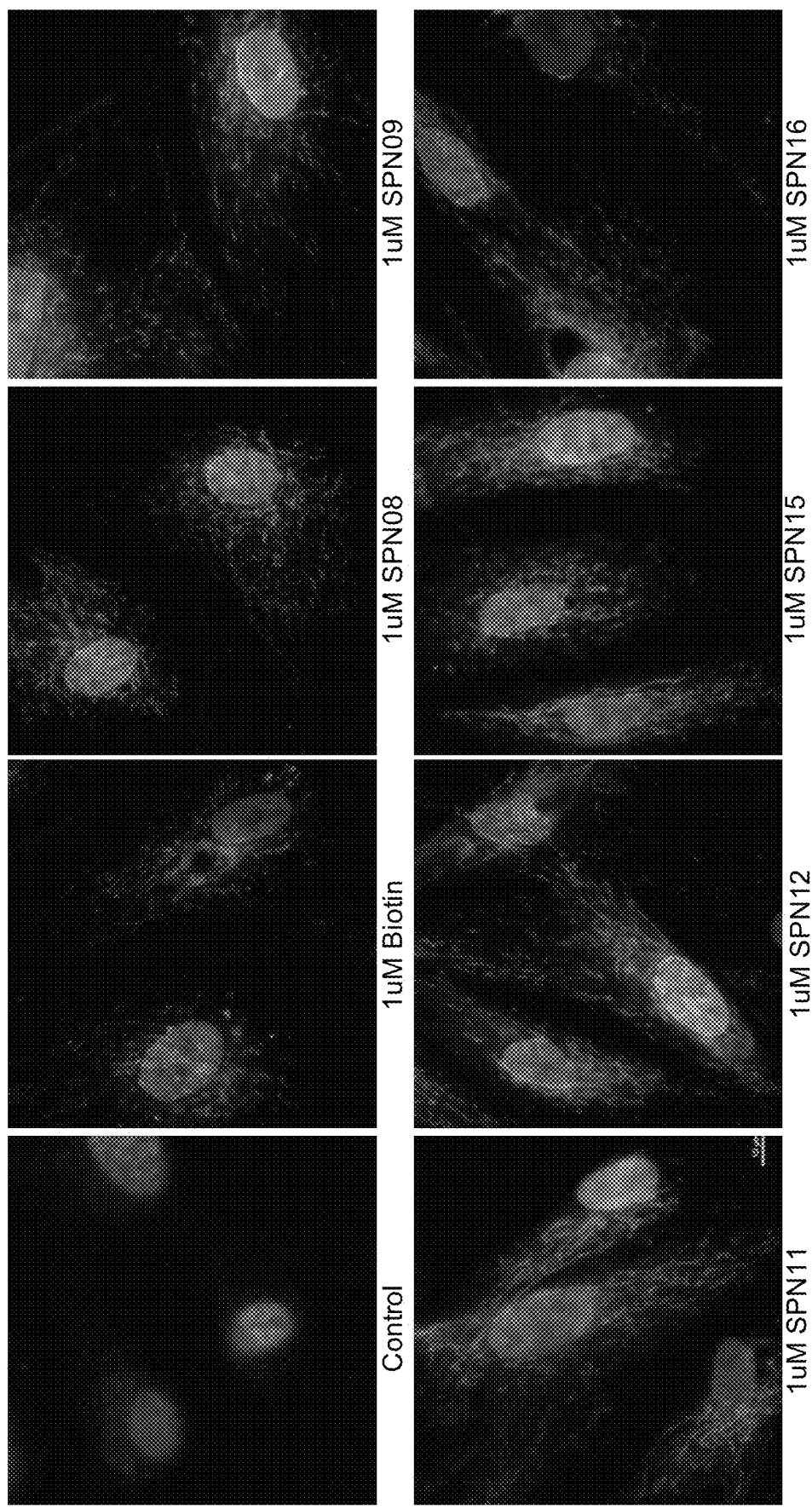
FIG. 4 are fluorescent microscopic images related to cellular uptake of certain exemplary compounds.

FIG. 4 shows representative microscopic images of ARPE-19 human retinal pigment epithelial cells after 1-hour incubation with 1 uM biotin or selected peptide-conjugated biotin molecules from TABLE 2. Intracellular biotin is visualized with streptavidin-AlexaFluor594 (red fluorescence). Nuclei are visualized with Hoechst 33342 dye (blue fluorescence) (1000× magnification). All peptide-conjugated biotin compounds (SPN08, SPN09, SPN11, SPN12, SPN15 and SPN16) showed intense red staining with a perinuclear distribution.

Figure 5:
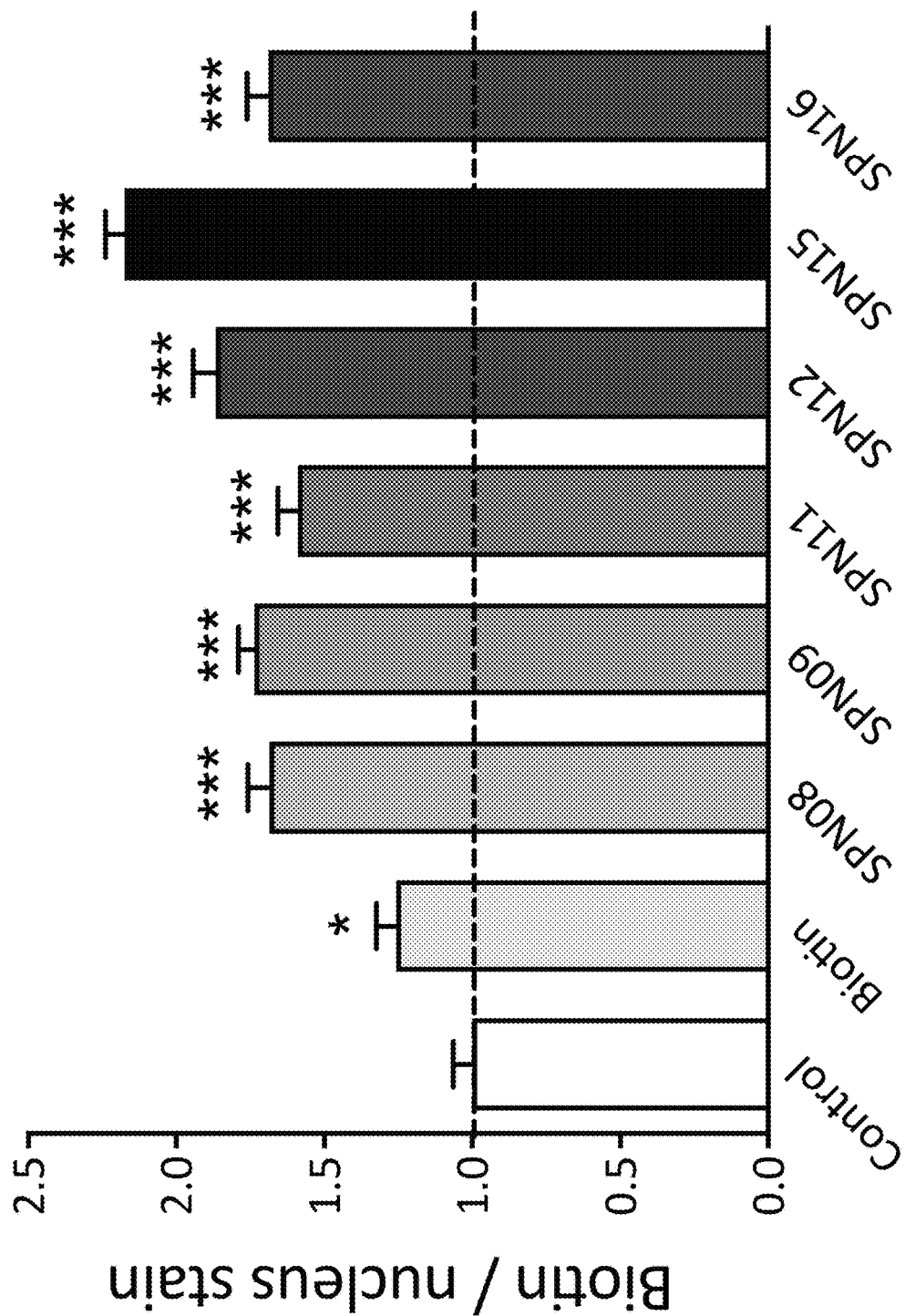
FIG. 5 is a graph showing exemplary cellular uptake.

FIG. 5 is a graph showing biotin uptake in ARPE-19 human retinal pigment epithelial cells after 1-hour incubation with 1 uM biotin or selected peptide-conjugated biotin molecules from TABLE 2. Peptide-conjugated biotin molecules delivered significantly higher intracellular biotin content compared to free biotin in ARPE-19 cells. The ratio of streptavidin fluorescence to Hoechst fluorescence was calculated from 10 random fields and averaged for each treatment. All data were then normalized to treatment with free biotin, with free biotin arbitrarily set as 1.0. All peptide-conjugated biotin molecules resulted in significantly higher intracellular biotin staining compared to free biotin (***P<0.001). The uptake of peptide-conjugated biotin molecules was 1.5 to 2 times higher than free biotin.

These peptides enter cells by simple diffusion, and once in the cell, they are seen only in the mitochondria. As confirmed by FIG. 2 and FIG. 4 for the identified SPN peptides. The distribution pattern shown for those peptides (filamentous network starting around the nucleus) is very distinct for mitochondria. Notice the nucleus is not stained, and the staining is not everywhere inside the cell. This greatly reduces the chance of side effects by the compound acting on other cellular organelles.

These results show that conjugation of biotin to the exemplary short, water-soluble, aromatic-cationic peptide sequences can significantly increase cell uptake of biotin. The microscopic images in FIG. 2 and FIG. 4 show that conjugation of biotin to SS-31, SPN02, SPN07 and SPN10 (SEQ ID NO:1) can greatly enhance biotin uptake into two different cell lines (kidney and retinal epithelial cells). These four short peptides all follow an alternating aromatic-cationic motif, with SS-31 and SPN02 having a "cationic-aromatic-cationic-aromatic" sequence order, while SPN07 and SPN10 (SEQ ID NO:1) having an "aromatic-cationic-aromatic cationic" sequence order. All exemplary peptides are water-soluble. SPN02 demonstrates that a pentapeptide can work as well as tetrapeptides and is water-soluble. SS-31 shows that non-naturally occurring amino acids (2'6'-dimethylTyr) can be substituted for natural-occurring amino acids. These peptides also support the use of Tyr, Phe or Trp as the aromatic amino acid, and the use of Arg or Lys as the cationic amino acid. The exemplary examples demonstrate that the amino acids can be in D- or L-configuration, and amidation of the C-terminus has no impact on mitochondria-delivery but can improve peptide stability against carboxypeptidase degradation in vivo.

A generic peptide of 4-6 amino acids with an alternating aromatic-cationic motif made of naturally-occurring or non-naturally occurring amino acids, in either D- or L-configuration, with or without C-terminus amidation, can serve as a water-soluble delivery vector to enhance cellular uptake of biotin in mammalian cells.

Example 2—Short Aromatic-Cationic Peptide Sequences Selectively Deliver Biotin to the Inner Mitochondrial Membrane Certain exemplary alternating aromatic-cationic peptide sequences listed in Table 1 can selectively target and localize to the inner mitochondrial membrane.

The perinuclear distribution pattern for all the peptide-conjugated biotin molecules (FIG. 2 and FIG. 4) suggests they are localized to the filamentous mitochondrial network.

To demonstrate mitochondrial localization of peptide-conjugated biotin molecules, ARPE-19 human retinal pigment epithelial cells were incubated with 1 uM SPN05, SPN12 or SPN15 for 2-hours in serum-free DMEM/F12 media. Cells were fixed with 4% PFA at RT for 10 min and then permeabilized with 0.1% Triton X-100 at RT for 10 min. Cells were blocked with 2% BSA (bovine serum albumin) at RT for 30 min, and then incubated with primary antibody for cytochrome c oxidase subunit 4 (COX4), a major protein complex expressed on the inner mitochondrial membrane. The rabbit polyclonal COX4 antibody (Invitrogen PAS-29992, Waltham, Mass.) was used at 1:500 dilution in 2% BSA at 4° C. overnight. Cells were then incubated with secondary antibody (goat anti-rabbit Alexa Fluor 488, 1:500 dilution, Invitrogen A-11008) and Streptavidin-Alexa Fluor 594 (Jackson ImmunoResearch, West Grove, Pa.) and 5 ug/ml Hoechst 33342 (Novus Biologicals, Centennial, Colo.) for 30 min at RT. Live cell image buffer was added and Alexa Fluor-594 fluorescence), Alexa Fluor-488 and Hoechst fluorescence were observed using the Nikon Eclipse Ti2 fluorescence microscope (100× oil objective).

Figure 6:
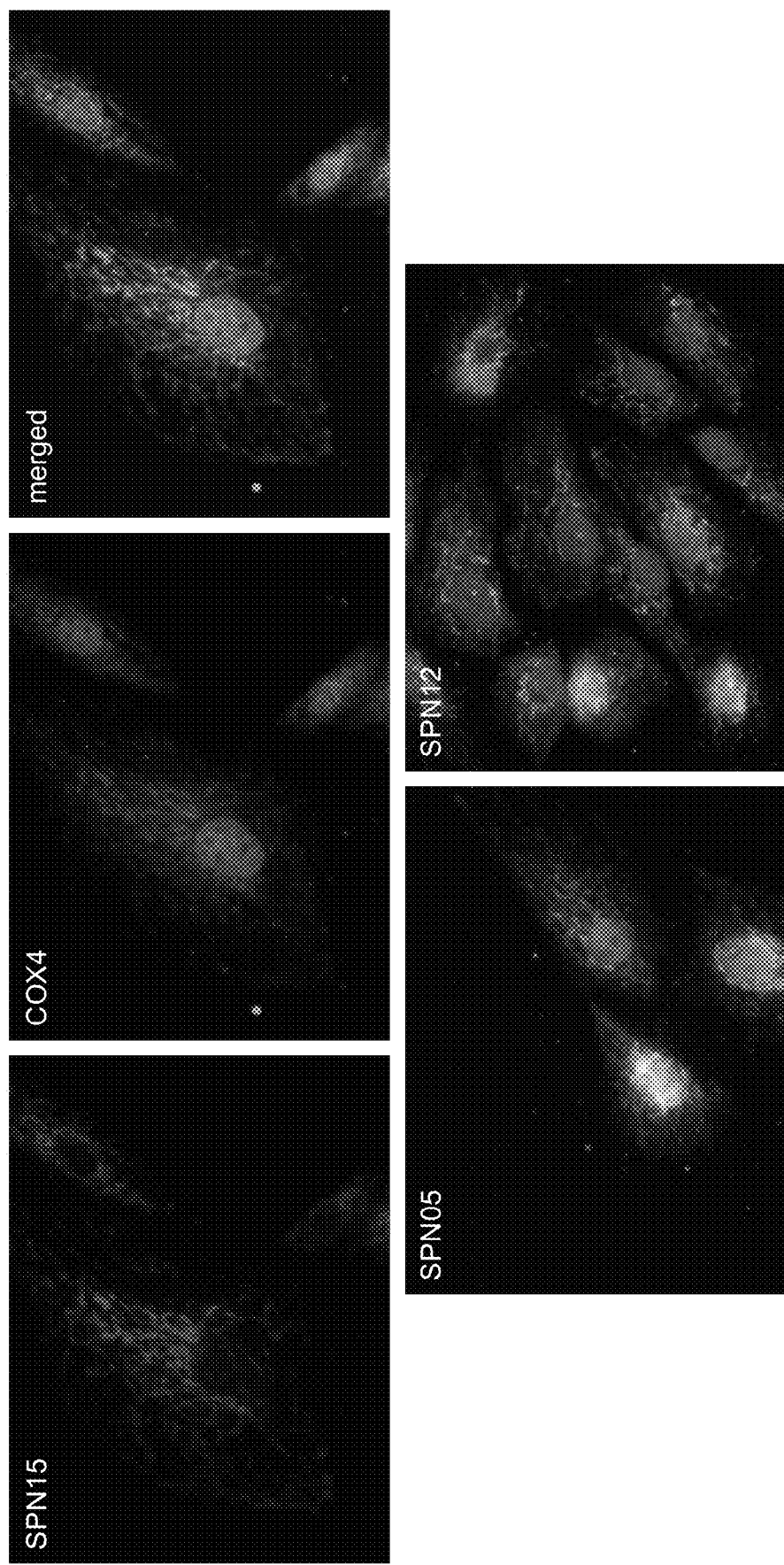
FIG. 6 are fluorescent microscopic images related to mitochondria-targeting of certain exemplary compounds.

FIG. 6 shows co-localization of peptide-conjugated biotin molecules with cytochrome c oxidase. Top panel are representative microscopic images of SPN15 (staining red), cytochrome c oxidase (COX) (staining green), and the merged image (yellow/orange). Bottom panel shows images of SPN05 and SPN12 merged with COX staining (yellow/orange). All images shown in 600× magnification.

These results demonstrate that short aromatic-cationic peptide sequences can serve as delivery vectors to target biotin to mitochondria. COX4 is a subunit of cytochrome c oxidase that is the terminal complex (complex IV) of the electron transport chain. The COX complex is a major regulation site for oxidative phosphorylation on the inner mitochondrial membrane. The co-localization of biotin staining from SPN05, SPN12 and SPN15 with COX4 staining demonstrate that these short aromatic-cationic peptide sequences can serve as mitochondria-targeting sequences to deliver biotin to the inner mitochondrial membrane.

Example 3—Peptide-Conjugated Biotin Molecules can Promote Cell Growth Under Prolonged Serum Starvation Serum removal can cause decrease in cellular ATP, cell cycle arrest, and/or apoptosis. Serum deprivation can inhibit the ability of cultured cells to proliferate. Incubation with certain exemplary peptide-conjugated biotin molecules can promote cell viability under serum-free conditions.

In the first model, HK-2 cells were cultured in 96-well plates in serum-free DMEM alone or in serum-free DMEM containing 10 nM of SPN11 or SPN12 for 11 days. Culture medium was replaced every 3 days.

Cell viability was measured using the Alamar Blue Cell Proliferation Assay (Bio-Rad), according to manufacturer's protocol. Alamar Blue uses resazurin to measure reducing power of living cells. The weakly fluorescent resazurin is reduced to the highly fluorescent resorufin when reduced by cellular metabolism. Briefly, alamar blue reagent (10 ul) was added to the culture medium and incubated for 1 h at 37° C. Fluorescence from resorufin (Ex/Em 530/590 nm) was detected using a microplate reader (SpectraMax iD3, Molecular Devices).

Figure 7:
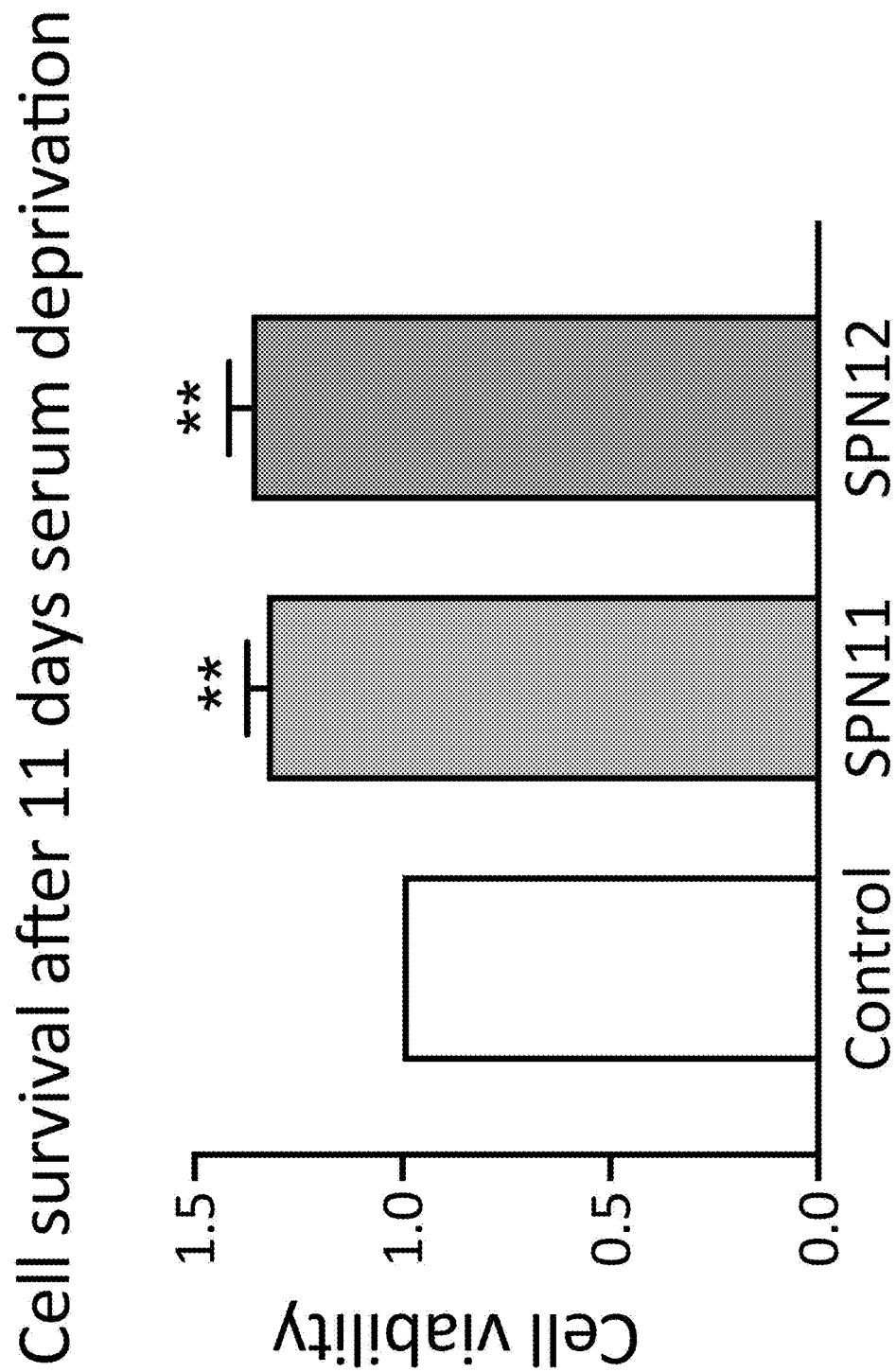
FIG. 7 is a graph showing exemplary cell viability.

FIG. 7 is a graph showing cell viability in HK-2 cells after 11 days of serum starvation. Treatment with just 10 nM of SPN11 or SPN12 significantly improved cell viability by 35% in the absence of serum (**P<0.005).

Figure 8:
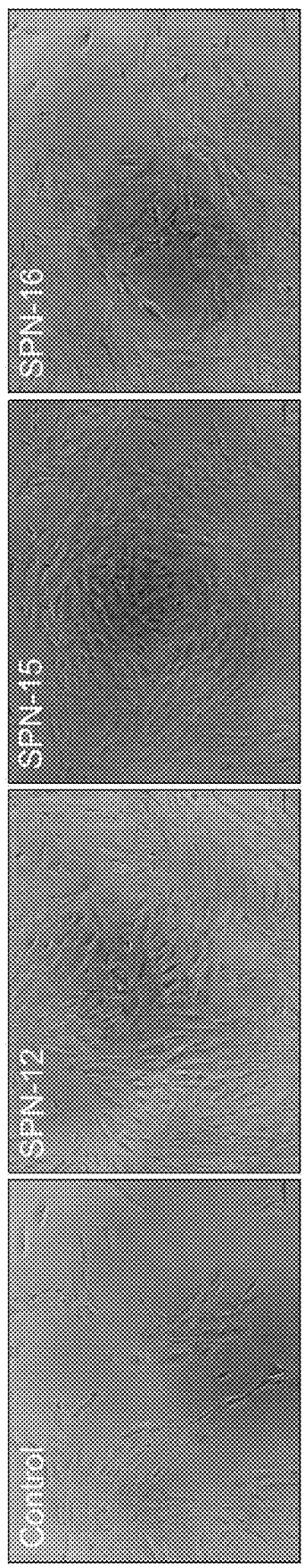
FIG. 8 are microscopic images showing exemplary cell number.

In the second model, ARPE-19 cells were grown in serum-free DMEM in the absence or presence of peptide-conjugated biotin molecules for 30 days. Serum-free media was supplemented with 10 nM of SPN12, SPN15 or SPN16 compounds (all at 10 nM) was replaced every 3 days. Culture medium was replaced every 3 days. FIG. 8 are representative microscopic images show that all three SPN compounds increased cell number after prolonged serum deprivation.

Figure 9:
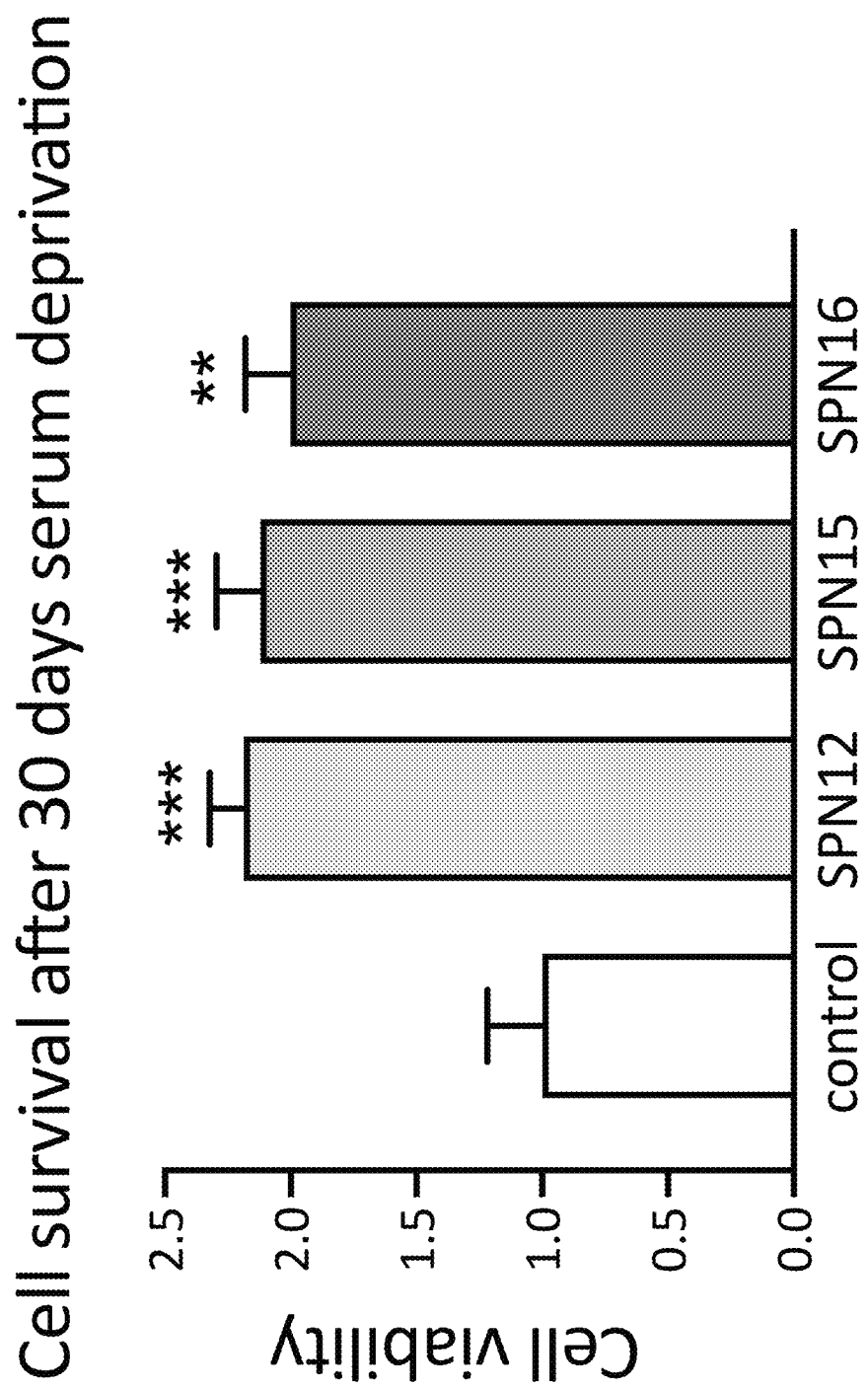
FIG. 9 is a graph showing exemplary cell viability.

FIG. 9 shows that treatment with SPN12, SPN15 and SPN16 significantly doubled cell viability after 30 days of serum deprivation compared to control. Data represent mean±SEM from 6 samples for each treatment (P<005; *P<0.001, compared to control).

These results show that addition of just 10 nM of peptide-conjugated biotin molecules can significantly double cell survival in serum-free conditions. These results demonstrate that exemplary mitochondria-targeted biotin molecules are biologically active (i.e., they alter cell biology) to protect cell survival in at least two different mammalian cell systems.

Example 4—Peptide-Conjugated Biotin Molecules Increased Cellular ATP Content in Serum-Free and Nutrient-Deprived Cultures Serum removal can cause decrease in cellular ATP. Certain exemplary peptide-conjugated biotin molecules can increase cellular ATP levels in serum-deprivation and/or nutrient-deprivation conditions.

Human renal epithelial cells (HK-2) were cultured in DMEM containing 1 g/L glucose and 10% fetal bovine serum (FBS), 100 units/ml penicillin, and 100 ug/ml streptomycin. Cells were incubated in humidified incubator with 5% CO2 at 37° C. HK-2 cells were seeded in 96-well culture plates at an initial density of $5 \times 10^3$ cells. FBS was removed from the culture medium and cells were incubated in serum-free DMEM alone (control group) or containing 10 nM of biotin or peptide-conjugated biotin molecules for 7 days. All treatments were carried out with N=6 in each experiment. The culture medium was changed every 3 days.

Human retinal pigment epithelial cells (ARPE-19) were cultured in DMEM/F12 media containing 1 g/L glucose and 10% fetal bovine serum (FBS), 100 units/ml penicillin, and 100 ug/ml streptomycin. Cells were incubated in humidified incubator with 5% CO2 at 37° C. ARPE-19 cells were seeded in 96-well culture plates at an initial density of $5 \times 10^3$ cells. FBS was removed from the culture medium and cells were incubated in serum-free DMEM/F12 alone (control group) or containing 10 nM biotin or different peptide-conjugated biotin molecules for 7 days. All treatments were carried out with N=5-6 in each experiment. The culture medium was changed every 3 days.

ATP was measured using the ApoSENSOR ATP Bioluminescence Assay Kit (BioVision) according to manufacturer's protocol. This kit utilizes luciferase to catalyze the formation of light from ATP and luciferin. Briefly, cells were treated with 100 ul of Nuclear Releasing Buffer for 5 min at RT with gentle shaking. 10 ul of ATP Monitoring Enzyme was added to cell lysate, and luminescence was measured using a microplate reader (SpectraMax iD3, Molecular Device). ATP levels were normalized to the serum-free DMEM control group (arbitrarily set to 1.0).

Figure 10:
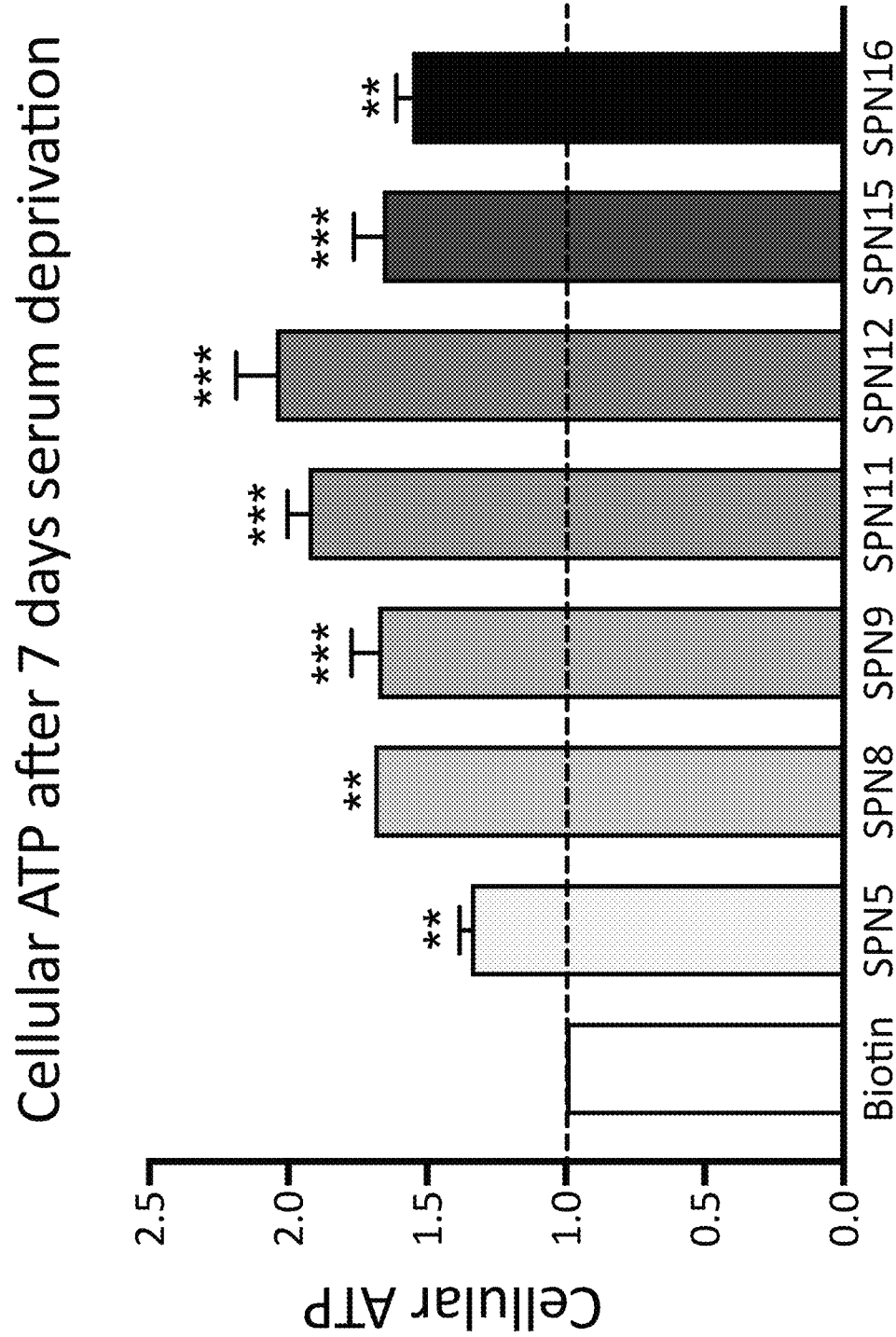
FIG. 10 is a graph showing exemplary cellular ATP levels.

All peptide-conjugated biotin molecules resulted in higher ATP concentrations compared to free biotin in HK-2 cells after 7 days in serum-free conditions (FIG. 10). Data shown are mean±SEM from 6 samples per treatment. SPN08, SPN09, SPN11, SPN12, SPN15, and SPN16 elevated ATP levels in serum-free conditions by 35%-100%, compared to free biotin (P<0.005; *P<0.001).

Figure 11:
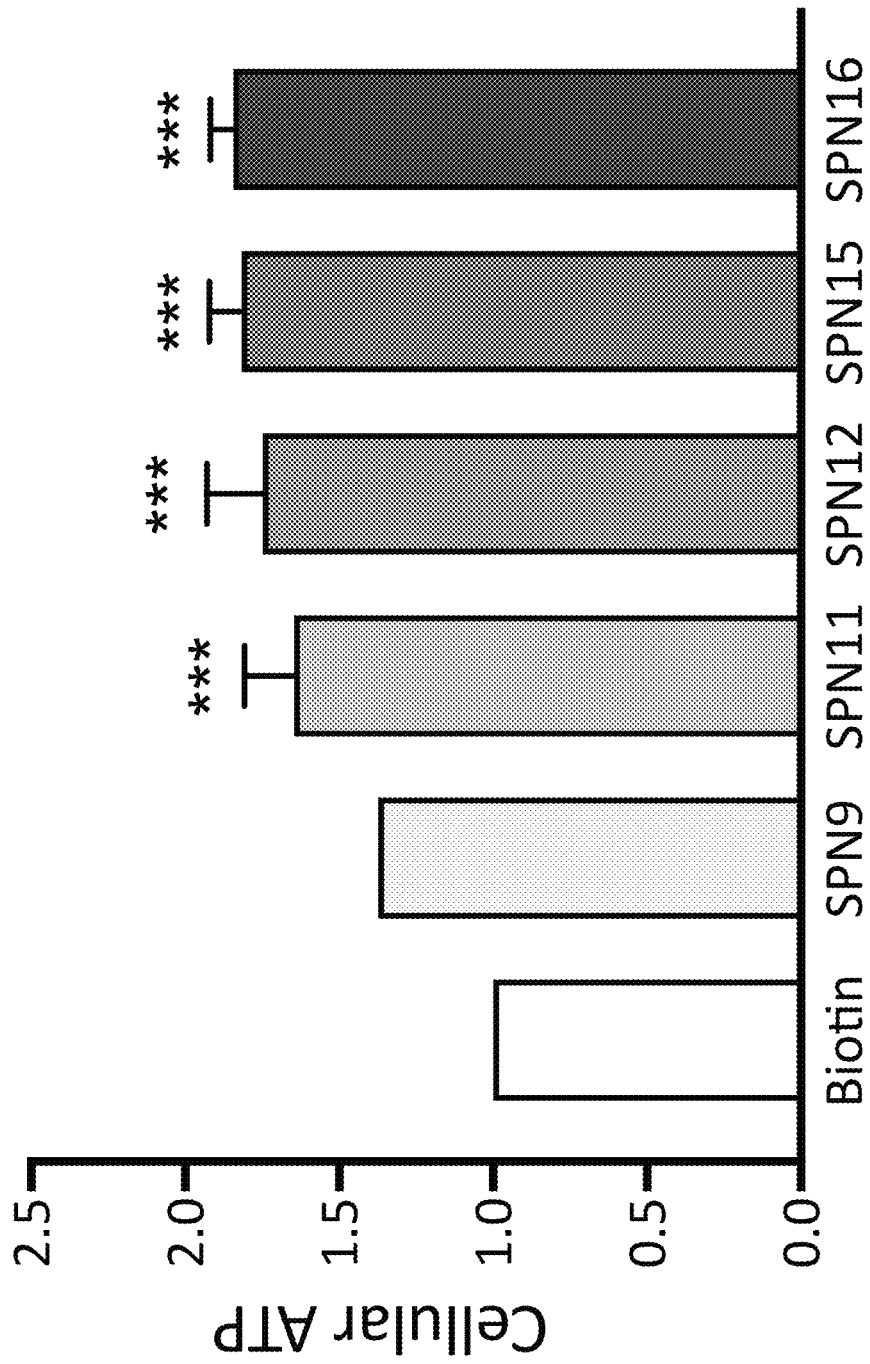
FIG. 11 is a graph showing exemplary cellular ATP levels.

The peptide-conjugated biotin molecules also significantly increased ATP concentration in ARPE-19 cells after 7 days of serum starvation. Data shown are mean±SEM from 6 samples per treatment. The peptide-conjugated biotin molecules elevated ATP levels by 60-75%, compared to free biotin (***P<0.001) (FIG. 11).

The second model uses an extreme starvation model whereby HK-2 cells were cultured in 96-well plates in serum-free 5% DMEM in PBS (phosphate-buffered saline) for 3 days. Cells were treated with 10 nM free biotin or peptide-conjugated biotin molecules. All treatments were carried out with N=6 in each experiment.

Figure 12:
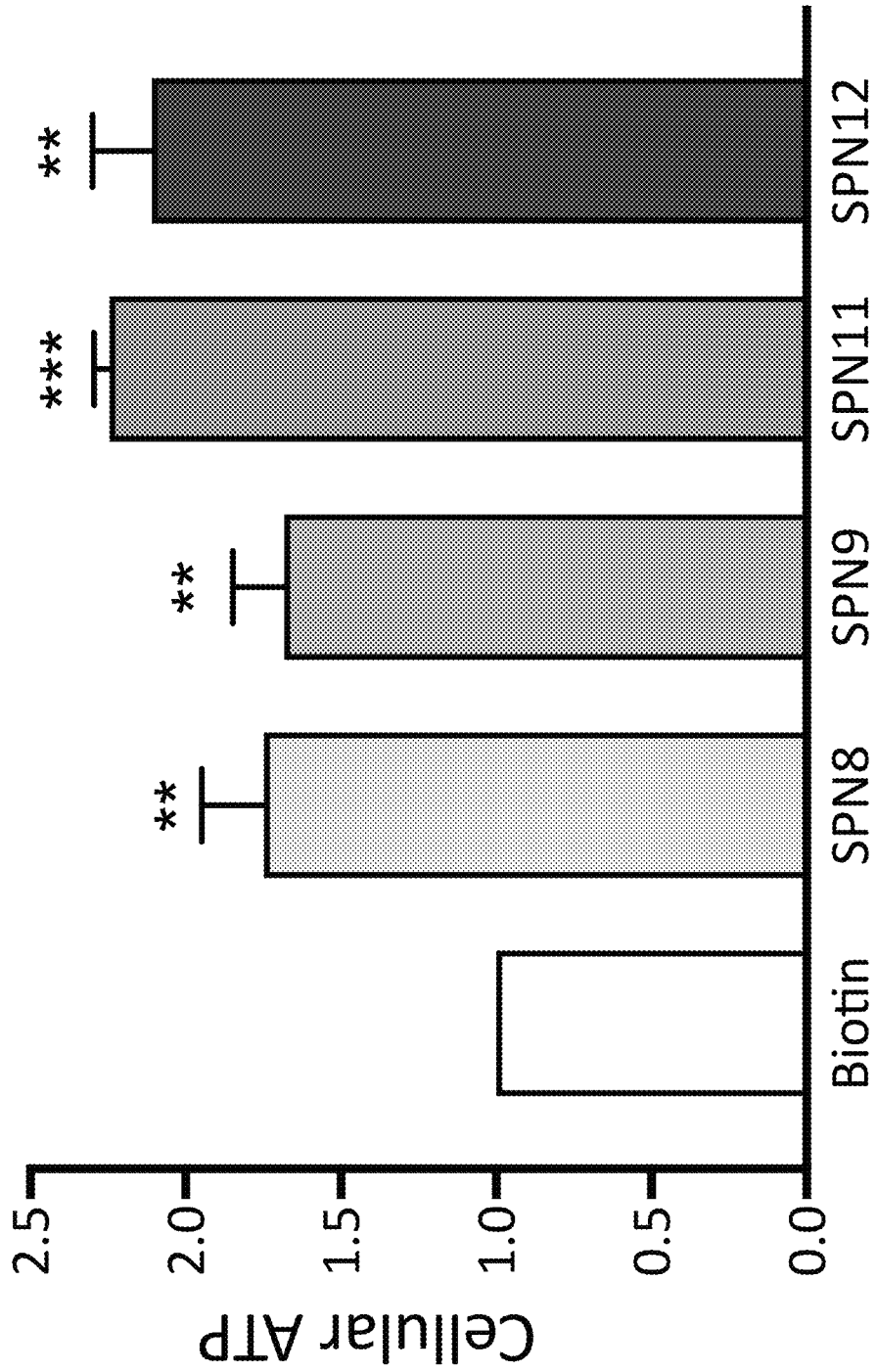
FIG. 12 is a graph showing exemplary cellular ATP levels.

All peptide-conjugated biotin molecules resulted in significantly higher ATP concentrations compared to free biotin under extreme starvation. Data shown are mean±SEM from 6 samples per treatment. (*P<0.05; P<0.01; *P<0.001), with SPN11, and SPN12 doubling ATP content (FIG. 12).

These results demonstrate that exemplary mitochondria-targeted biotin molecules are biologically active promoting mitochondrial ATP synthesis under serum- and nutrient-deprived conditions in at least two different mammalian cell systems.

Example 5—Peptide-Conjugated Biotin Molecules can Restore Mitochondrial Potential and Prevent Mitochondrial Fragmentation Caused by Serum Starvation Serum deprivation can induce mitochondrial depolarization which precedes the reduction in ATP synthesis. Certain exemplary peptide-conjugated biotin molecules can restore mitochondrial potential in cells cultured in serum-free medium.

Electron transfer along the electron transport chain on the inner mitochondrial membrane results in the pumping of protons from the mitochondrial matrix to the inter-membrane space. This generates an electrical potential across the inner mitochondrial membrane, and the proton gradient serves to drive the ATP synthase (complex V) to produce ATP from ADP. Withdrawal of serum or nutrients leads to decline in mitochondrial potential and reduced ATP production.

Human retinal pigment epithelial cells (ARPE-19) were cultured in DMEM/F12 media containing 1 g/L glucose and 10% FBS, 100 units/ml penicillin, and 100 ug/ml streptomycin. Cells were incubated in humidified incubator with 5% CO2 at 37° C. ARPE-19 cells were seeded in 35 mm glass plates at an initial density of $5 \times 10^4$ cells. FBS was removed from the culture medium for 3 days to deplete endogenous biotin. Cells were then incubated in serum-free DMEM/F12 alone (control group) or DMEM/F12 containing 1 uM of SPN12 or SPN15 for 2 hours.

To determine mitochondrial potential, live cells were incubated with 5 nM tetramethylrhodamine methyl ester (TMRM, #70017, Biotium, Fremont, Calif.) in DMEM without phenol red. TMRM is a potential-dependent fluorescent dye (Ex/Em=548/573). TMRM accumulates in negatively charged polarized mitochondria and can be detected as red fluorescence. Total mitochondria were imaged with a mitochondrial potential-independent fluorescent dye (100 nM MitoView Green; Ex/Em=490/523; #70054, Biotium, Fremont Calif.). Hoechst 33342 (10 ug/ml, Novus Biologicals, Centennial, Colo.) was added to stain nuclei. Live cells were covered with phosphate buffer and imaged using the Nikon Eclipse Ti fluorescent microscopy using the 60× water objective.

Figure 13:
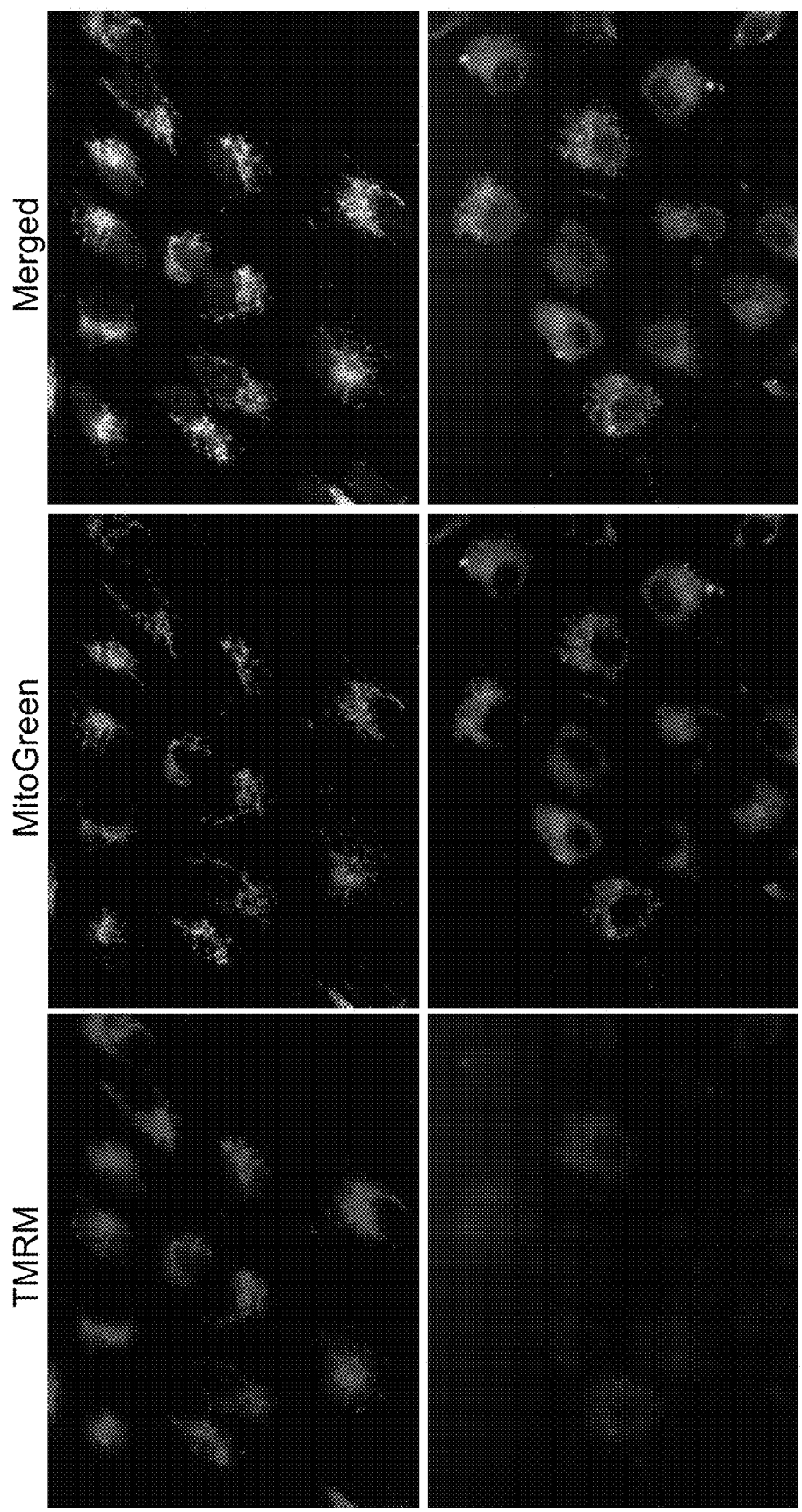
FIG. 13 are fluorescent microscopic images showing mitochondrial potential.

FIG. 13 (top panel) are representative fluorescent microscopic images of ARPE-19 cells cultured for 3 days in DMEM/F12 with 10% FBS. FIG. 13 (bottom panel) are representative images of ARPE-19 cells cultured for 3 days in serum-free DMEM/F12. TMRM (red) shows dramatic loss of mitochondrial potential in serum-free condition when compared to serum control. The mitogreen (green) stain also shows that serum-free condition caused mitochondria to fragment and aggregate in a perinuclear pattern with no clear filamentous network. When the images are merged, mitochondrial depolarization can be seen all cells without serum.

Figure 14:
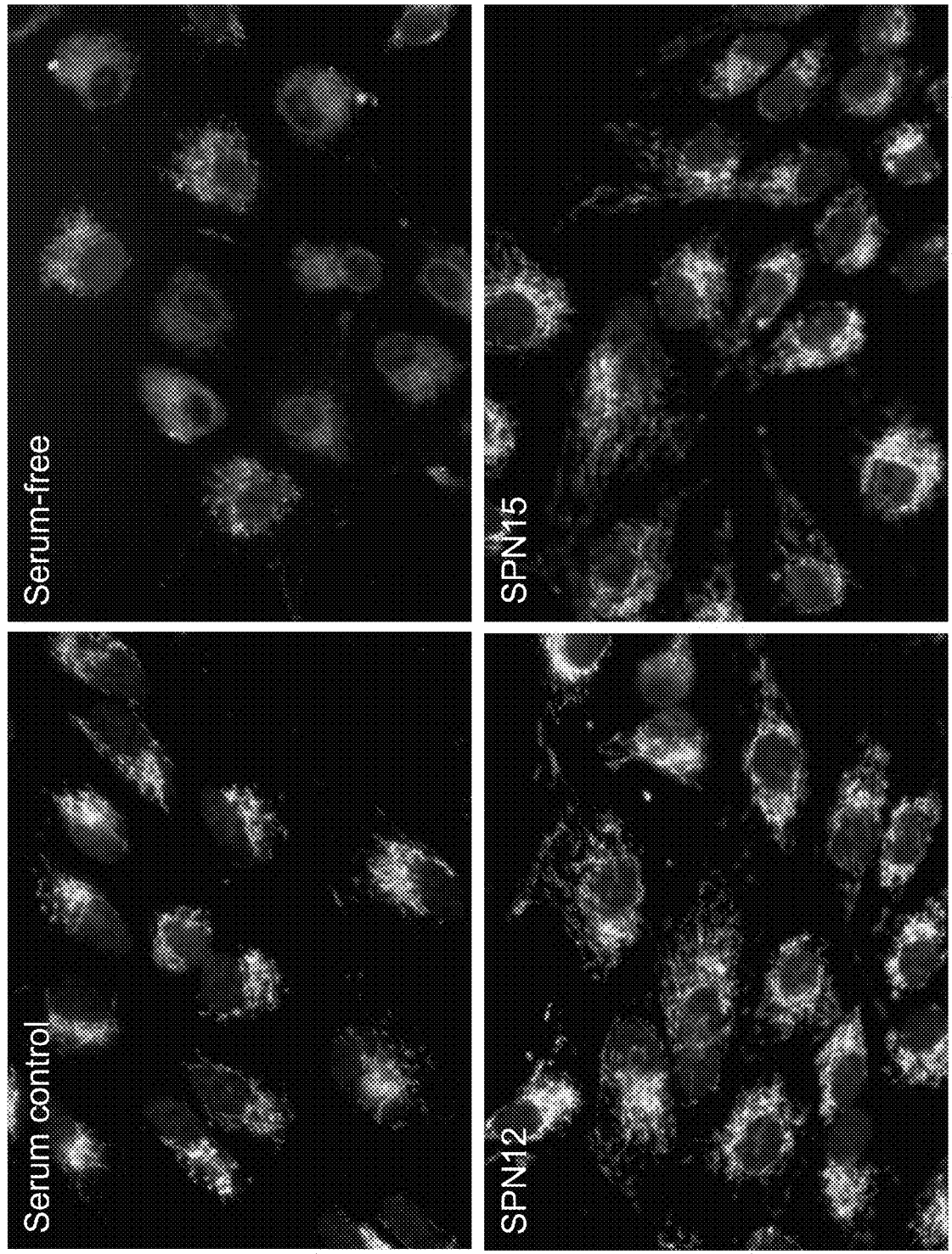
FIG. 14 are fluorescent microscopic images showing exemplary mitochondrial potential.

FIG. 14 are representative fluorescent microscopic images of ARPE-19 cells cultured for 3 days in 10% FBS (serum control) or in serum-free medium (serum-free) alone or after 2 hours incubation with 1 uM of SPN12 or SPN15. The images shown are merged images of TMRM (red) and MitoGreen (green). Two-hour incubation with SPN compounds was sufficient to restore mitochondrial potential in all cells and recover the filamentous mitochondrial network in ARPE-19 cells after 3 days of serum starvation.

These results show that mitochondria are completely depolarized after 3 days of serum starvation and the mitochondria network in the cells are fragmented. The peptide-conjugated biotin molecules (SPN12 and SPN15) can rescue mitochondrial potential in a matter of 2 hours in serum starvation. These results confirm that biotin conjugated to the aromatic-cationic peptide sequences is targeted to the inner mitochondrial membrane and are biologically active in protecting the electrical potential across the inner mitochondrial membrane.

Example 6—Peptide-Conjugated Biotin Molecules are More Effective than Free Biotin in Wound Repair Certain exemplary peptide-conjugated biotin molecules can accelerate wound healing in cell cultures. The in vitro scratch assay is an easy and well-developed method to measure cell proliferation and migration over a "wound area" in vitro. This assay involves creating a "scratch" in a cell monolayer with a pipette tip and then examining the rate at which cells proliferate and migrate to close the scratch.

HK-2 cells were cultured in DMEM (1 g/L glucose) with 10% FBS, 100 units/ml penicillin, and 100 ug/ml streptomycin. $3 \times 10^5$ cells were plated per well in 6-well plates in DMEM at 37° C. in a humidified incubator with 5% CO2 for one day prior to the experiment. To mimic the microenvironment of wounds in vitro, serum-free medium was used in the scratch assay. On the day of the scratch assay, the medium was replaced with serum-free DMEM, and a line scraped across the cell monolayer using a p1000 pipette tip. Cells were washed to remove cell debris and replaced with DMEM alone (control), or DMEM containing 10 nM biotin or peptide-conjugated biotin molecules.

The scratch area was examined immediately (day 0) using a Nikon Eclipse Ti2 fluorescence microscope. Six different field were captured for each sample using 4× objective. The scratch area (cell-free zone) was calculated using ImageJ software, an open-source Java image processing program inspired by NIH Image (National Institute of Health). The scratch area was re-examined after 24 hours (day 1), and the area was normalized to the area determined on day 0 for the same sample. All results were calculated as change from no-treatment control and averaged for the six fields.

Figure 15:
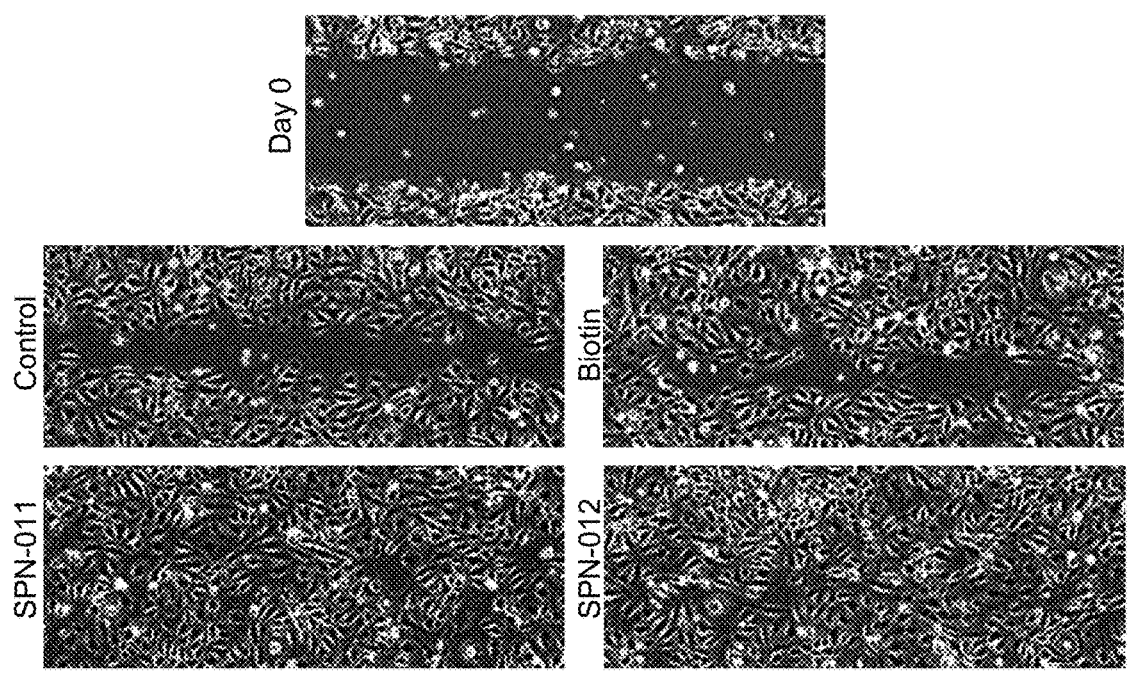
FIG. 15 are microscopic images of scratch area related to certain exemplary compounds.

FIG. 15 are representative microscopic images showing treatment with 10 nM SPN11, or SPN12 greatly accelerated the closure of the scratch in HK-2 cells 24 hours after mechanical scratch. The scratch areas determined after 24 hours are normalized to the area determined immediately after application of the scratch (Day 0) for each treatment group. Biotin had a small effect on reducing scratch area whereas the scratch area was almost completely closed by SPN11 and SPN12 in 24 hours.

Figure 16:
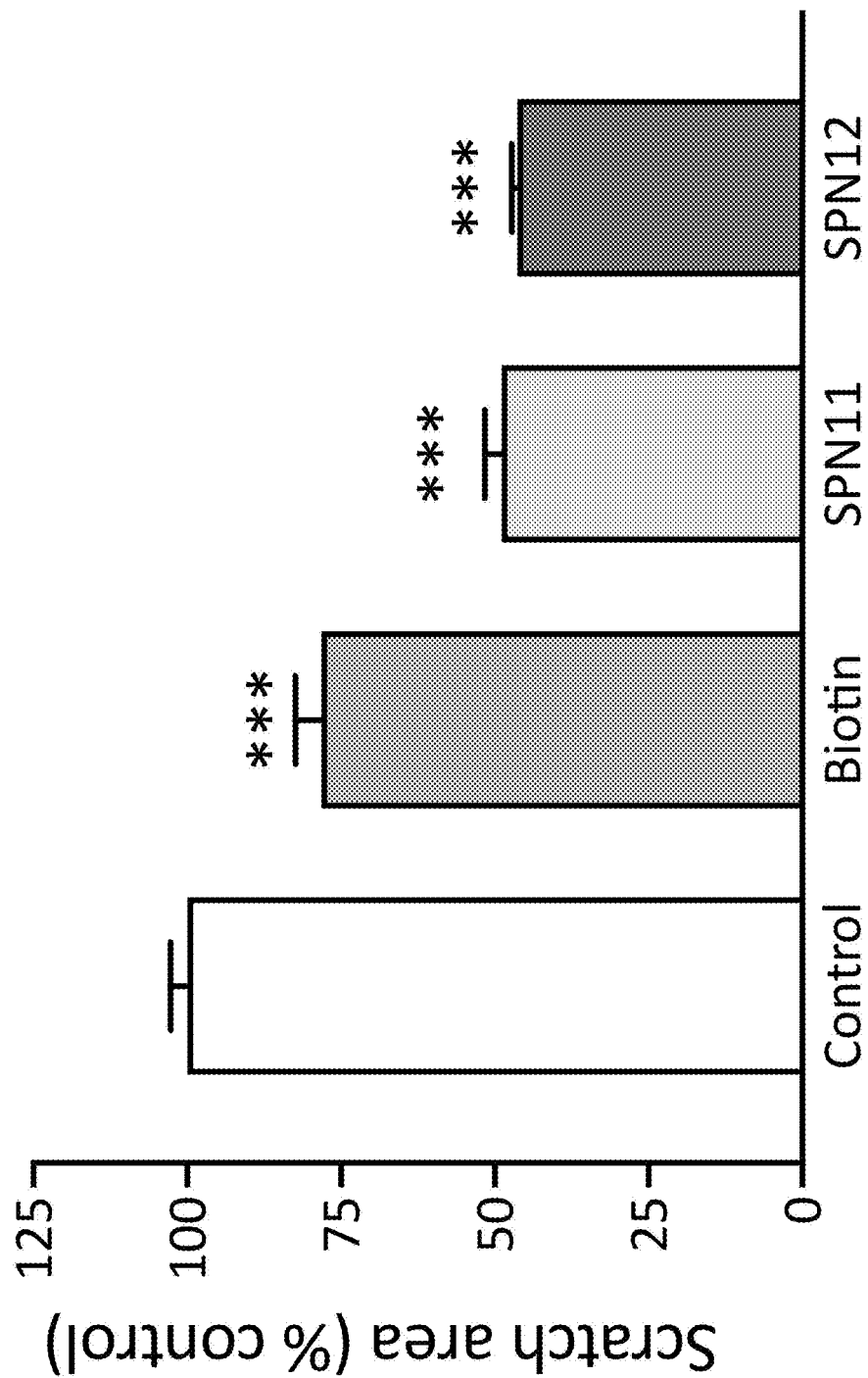
FIG. 16 is a graph showing exemplary scratch area.

FIG. 16 summarizes the effect of biotin, SPN11 and SPN12 on reducing scratch area 24 hours after application of mechanical scratch in HK-2 cells. All treatments significantly accelerated the closure of the scratch area (***$P<0.001$, compared to control). The biotin-conjugated peptides (SPN11 and SPN12) are twice as effective compared to biotin in reducing scratch area ($P<0.001$).

Figure 17:
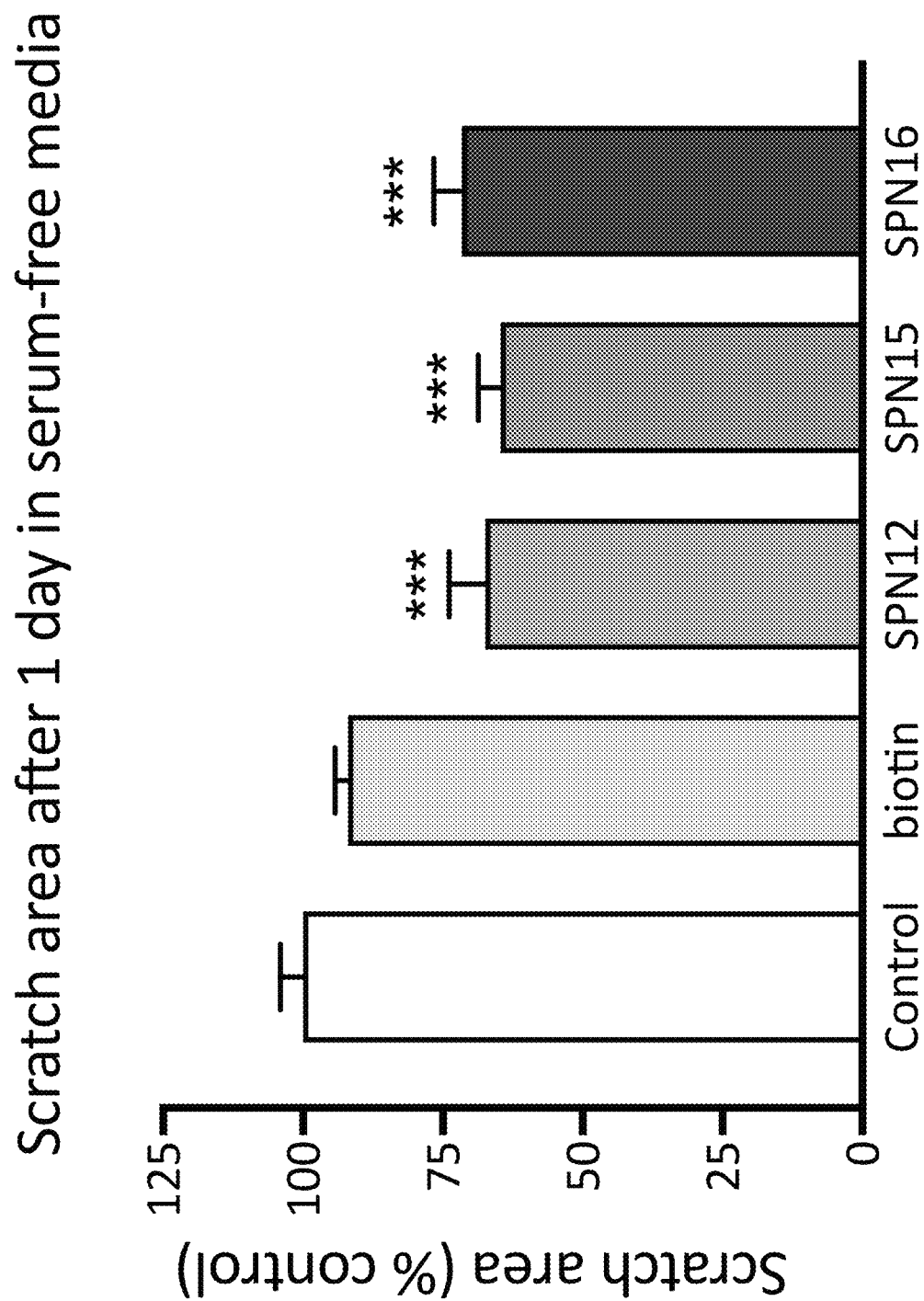
FIG. 17 is a graph showing exemplary scratch area.

FIG. 17 shows that the other peptide-conjugated biotin molecules, SPN15 and SPN16 also significantly accelerated the closure of the scratch area after 24 hours in another experiment in HK-2 cells (***$P<0.001$) and are three times more effective compared to free biotin ($P<0.001$).

Figure 18:
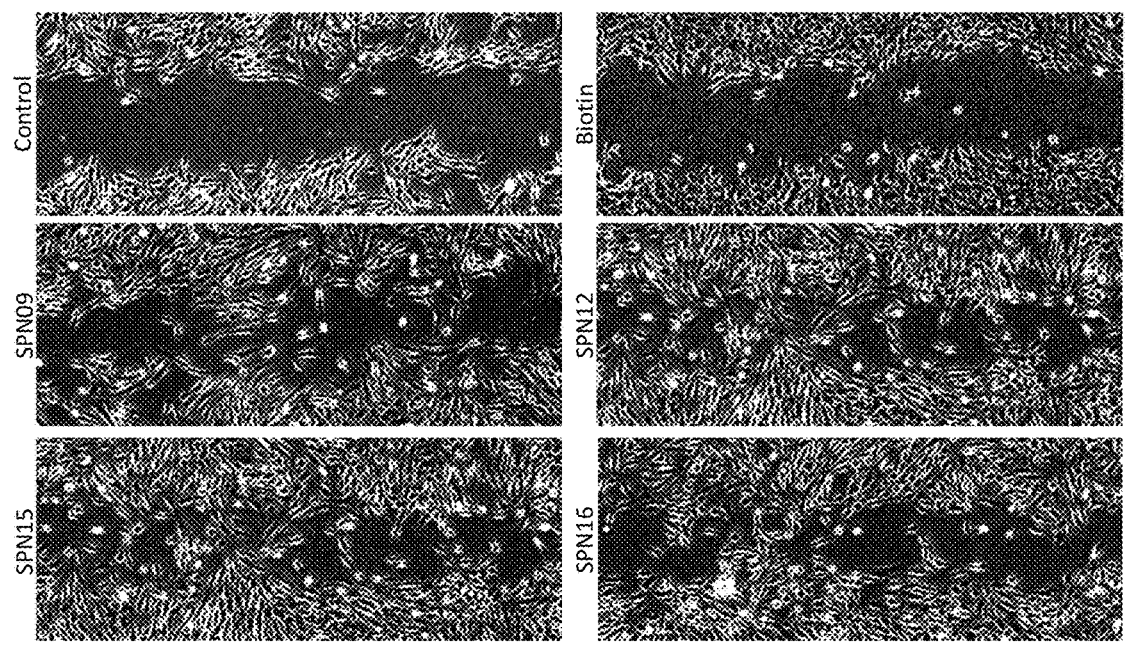
FIG. 18 are microscopic images of scratch area related to certain exemplary compounds.
Figure 19:
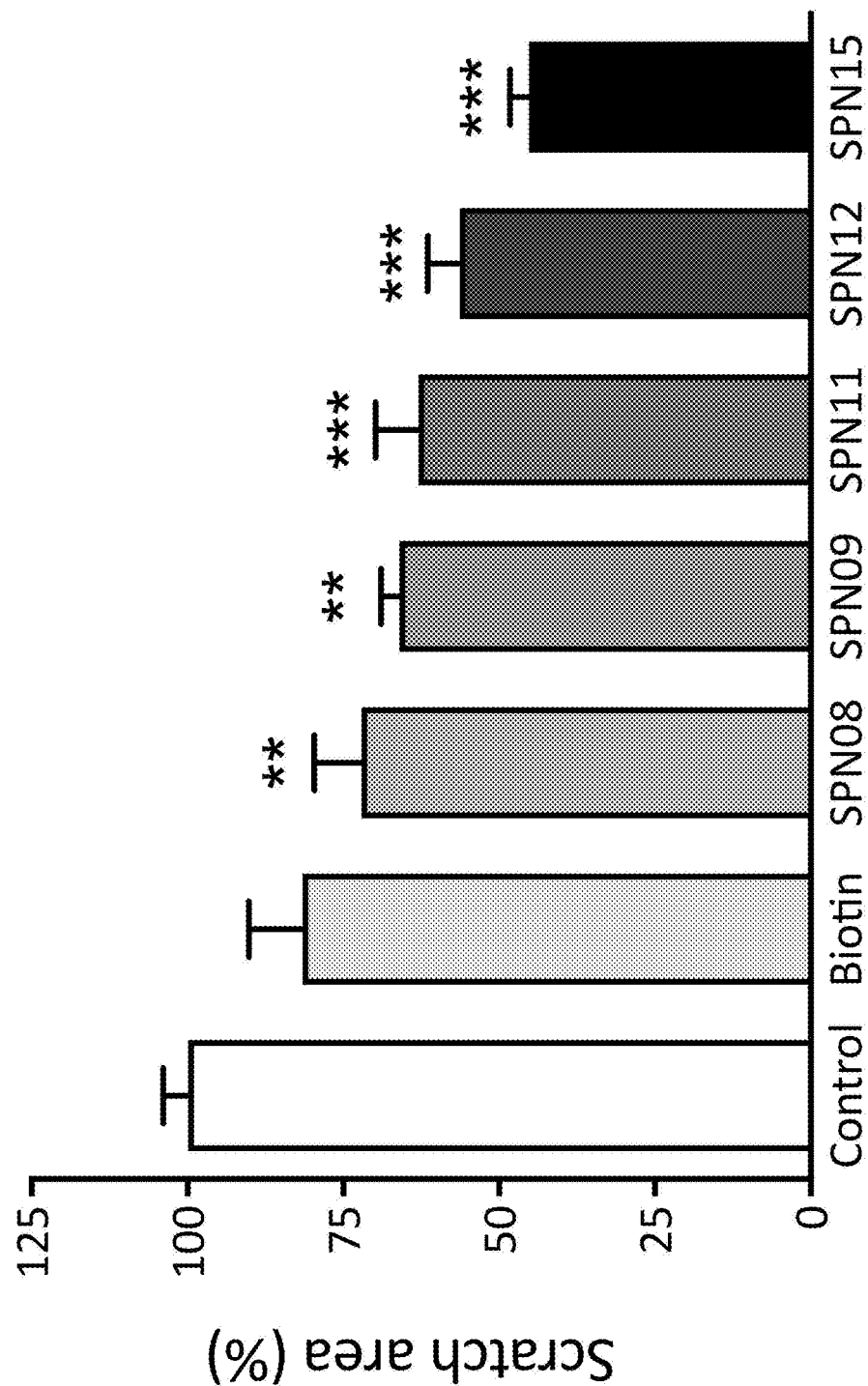
FIG. 19 is a graph showing exemplary scratch area.

The peptide-conjugated biotin molecules (SPN12, SPN15 and SPN16) also accelerated wound healing in ARPE-19 cells (FIG. 18). FIG. 19 is a graph summarizing the effects of the peptide-conjugated biotin molecules on scratch area ($P<0.01$; *$P<0.001$). The peptide-conjugated biotin molecules were significantly more effective (1.5 to 2-fold) compared to free biotin ($P<0.001$).

These results demonstrate that not only are the peptide-conjugated biotin molecules biologically-active, they are superior to free biotin in promoting wound healing in vitro.

Example 7—Peptide-Conjugated Biotin Molecules can Promote Cell Proliferation in Wound Area Re-epithelialization of a wound area require proliferation of cells at the wound edge, which can be impaired in most wounds due to lack of blood flow to deliver nutrients and/or growth factor(s) that can be necessary for cell proliferation. Cell proliferation in the wound edge can be monitored by proliferating cell nuclear antigen (PCNA) staining. To mimic the microenvironment of wounds in vitro, serum-free medium was used for the scratch assay in cell cultures.

Proliferating cells were identified by immunostaining with antibody to proliferating cell nuclear antigen (PCNA) according to standard procedures as presented in IHC World. PCNA staining was performed using the same plate of cells after determination of scratch area. HK-2 cells were fixed with ethanol:methanol (1:1) for 30 min at −20° C., permeabilized with 0.1% Triton X-100/PBS for 10 min at RT, blocked with 2% goat serum for 30 min at RT, and incubated with primary mouse anti-PCNA antibody (Dako Agilent, Santa Clara, Calif.) and secondary goat anti-mouse IgG-BI for 30 min at RT. Cells were then incubated with Streptavidin-Alexa Fluor 594 (Jackson ImmunoResearch, West Grove, Pa.) and Hoechst (Novus Biologicals, Centennial, Colo.) and imaged with a Nikon Eclipse Ti2 Fluorescent microscope (20× objective). All cell nuclei stain blue with Hoechst, but nuclei of proliferating cells stain red. The number of proliferating cells per field was quantified by the intensity of red nuclear stain and normalized to intensity of blue nuclear stain (determined by Nikon NIS-Elements Imaging Software).

Figure 20:
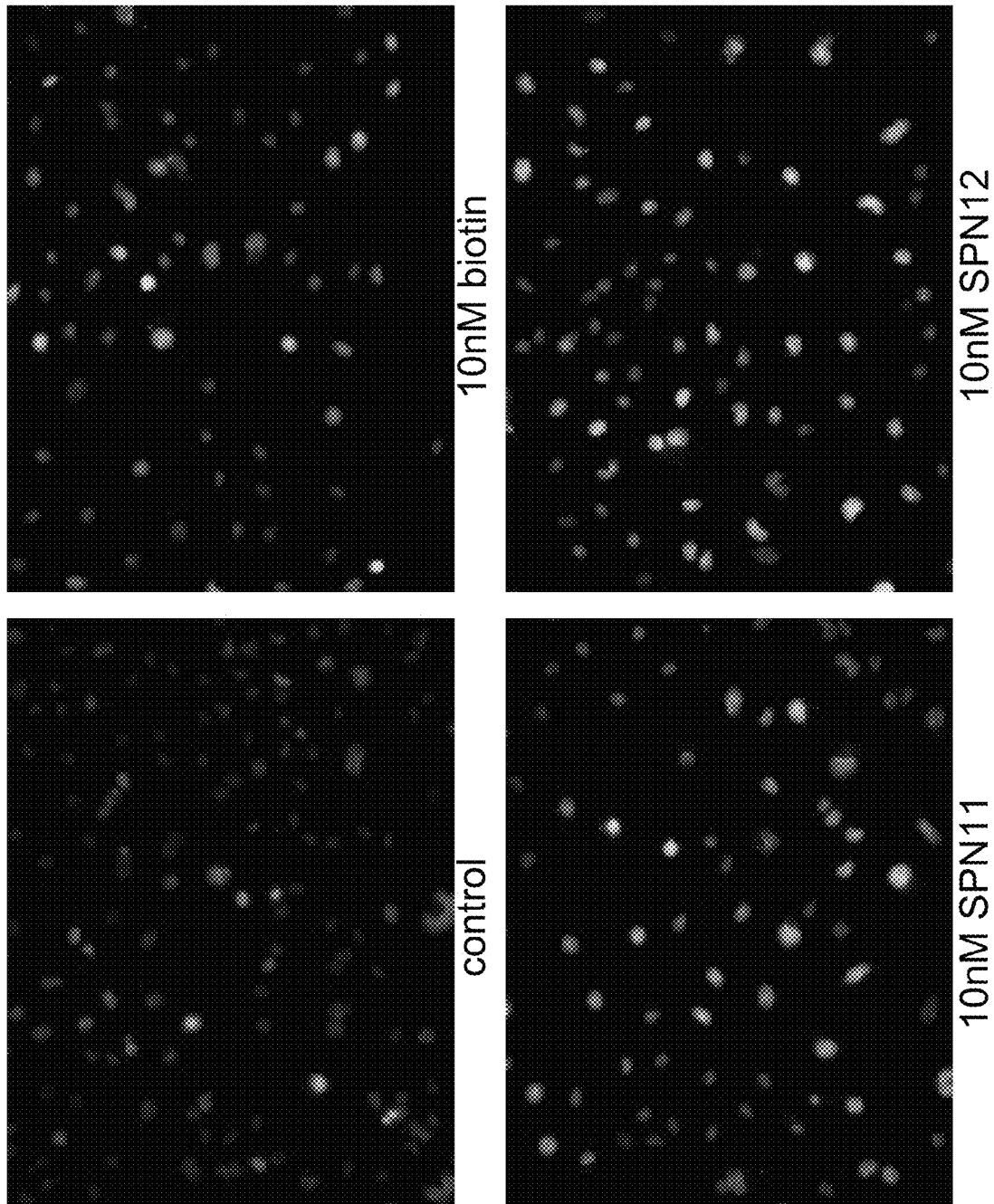
FIG. 20 are microscopic images related to cell proliferation of certain exemplary compounds.

FIG. 20 shows representative microscopic images (×40 magnification) of HK-2 human renal epithelial cell monolayers 24 hours after mechanical scratch in serum-free medium only (control), or in serum-free medium containing exemplary SPN compounds (10 nM). Cells positive for proliferating cell nuclear antigen are shown in red. All other nuclei are shown in blue. Compared to free biotin, SPN11 and SPN12 increased the number of proliferating cells at the edge of the scratch.

Figure 21:
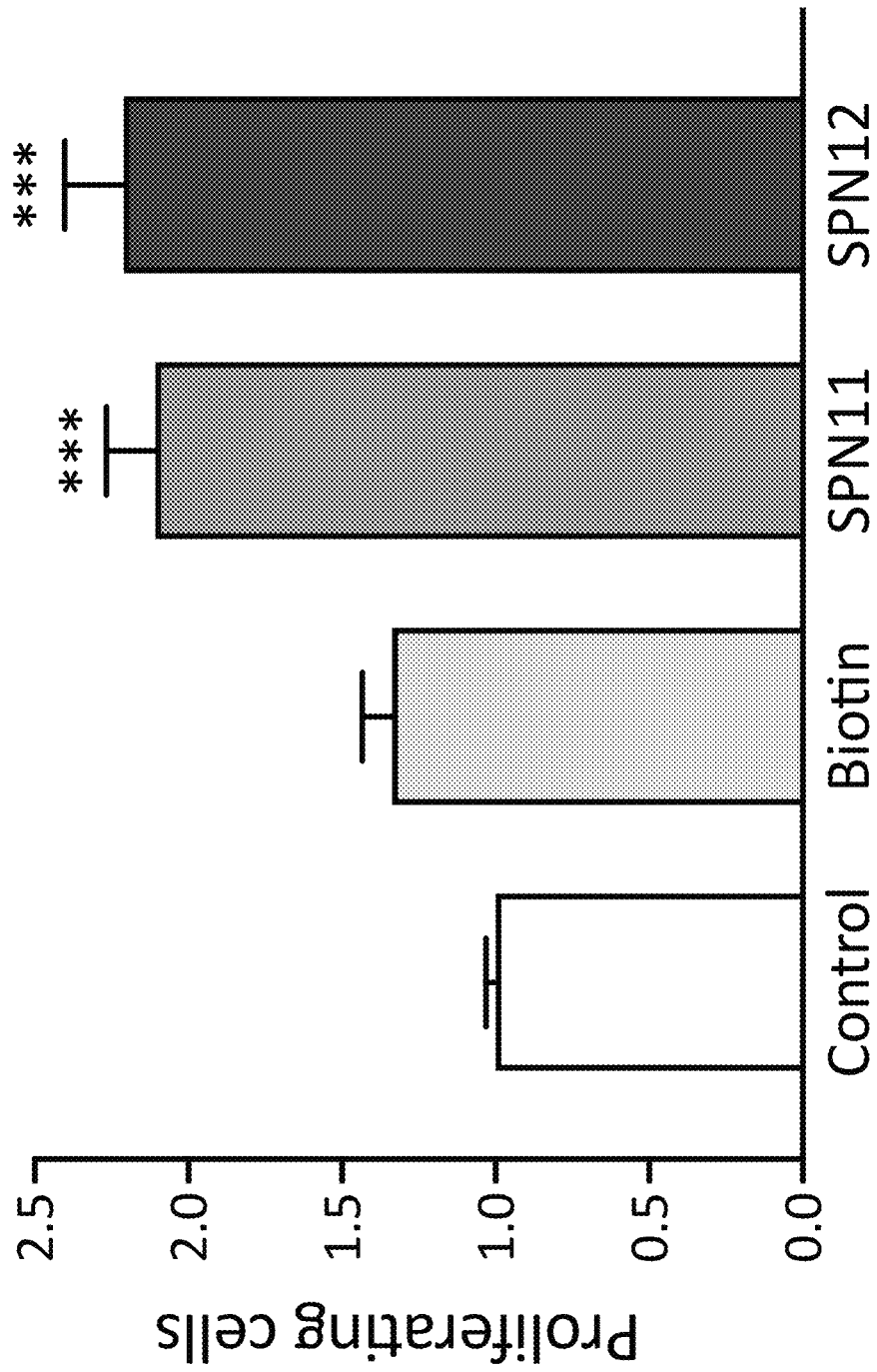
FIG. 21 is a graph showing exemplary cell proliferation.

FIG. 21 is a graph summarizing the number of proliferating cells in HK-2 human renal epithelial cell monolayers 24 hours after mechanical scratch in serum-free medium only (control), or in serum-free medium supplemented with 10 nM biotin or peptide-conjugated biotin molecules. The number of proliferating cells were normalized to all nuclei. The effect of biotin was small and did not reach statistical significance. Incubation with SPN11, and SPN12 doubled the number of proliferating cells at the edge of the scratch compared to control or biotin (***P<0.001).

Figure 22:
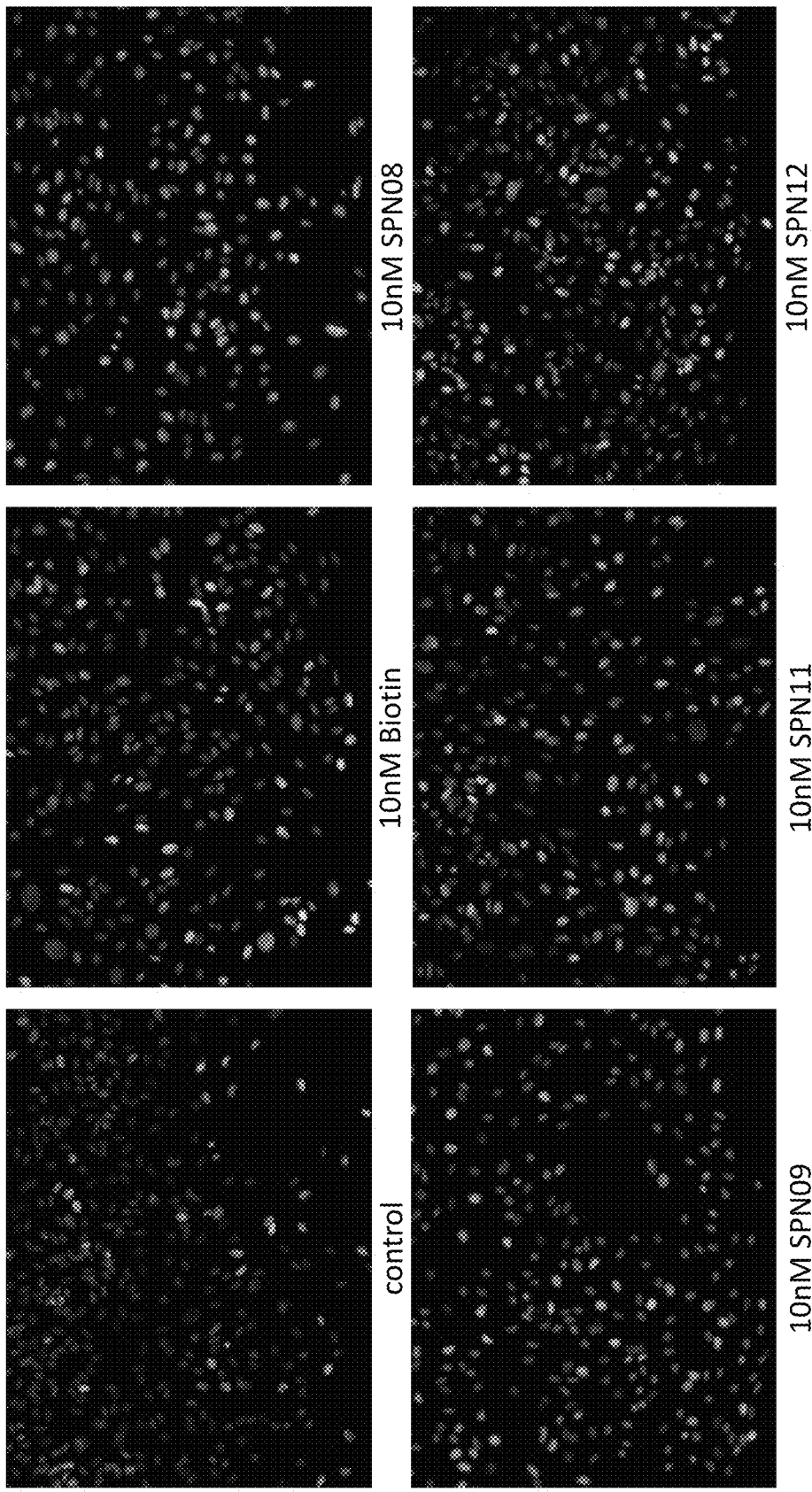
FIG. 22 are microscopic images related to cell proliferation of certain exemplary compounds.

FIG. 22 shows representative microscopic images (40× magnification) of ARPE-19 human retinal pigment epithelial cell monolayers 24 hours after mechanical scratch in serum-free medium only (control), or in serum-free medium supplemented with 10 nM free biotin or peptide-conjugated biotin molecules. Cells positive for proliferating cell nuclear antigen are shown in red. All other nuclei are shown in blue. Incubation with the SPN08, SPN09, SPN11, or SPN12 increased the number of proliferating cells at the edge of the scratch, while 10 nM biotin had no effect on cell proliferation.

Figure 23:
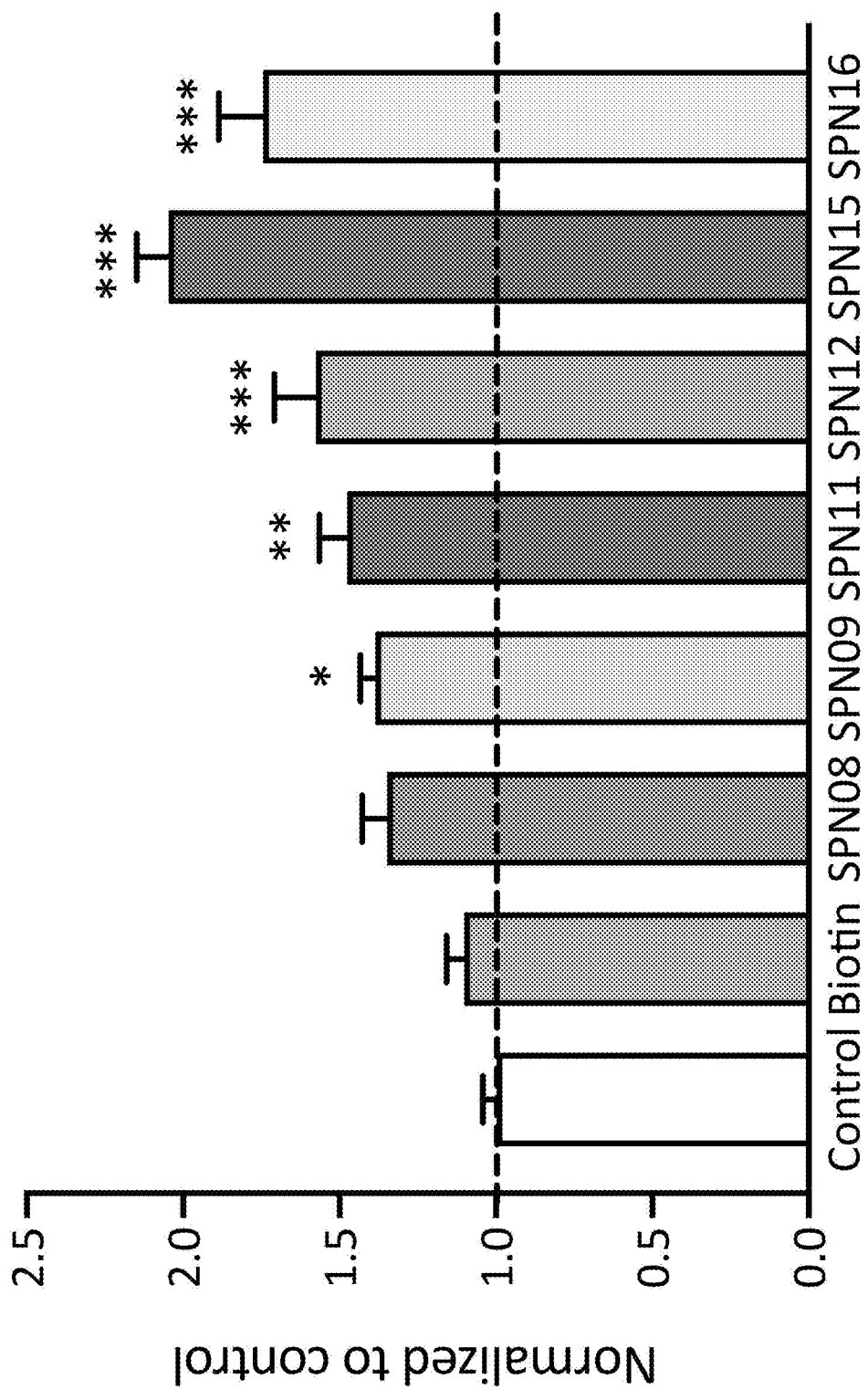
FIG. 23 is a graph showing exemplary cell proliferation.

FIG. 23 is a graph summarizing the number of proliferating cells in ARPE-19 human retinal pigment epithelial cell monolayers 24 hours after mechanical scratch in serum-free medium only (control), or in serum-free medium containing 10 nM biotin or peptide-conjugated biotin molecules. The number of proliferating cells were normalized to all nuclei. Incubation with each of SPN09, SPN11, SPN12, SPN15, and SPN16 significantly increased the percent of proliferating cells at the edge of the scratch by 35-100%, but biotin itself was without effect (*P<0.05; P<0.01; *P<0.001, compared to control).

These results show that the peptide-conjugated biotin molecules are more effective than biotin alone in promoting cell proliferation in a wound setting, and this is likely due to increased delivery of biotin to mitochondria.

Example 8—Peptide-Conjugated Biotin Molecules Protect Mitochondrial Potential of Cells at the Wound Edge Rapidly dividing cells can need ATP to support the synthesis of important building blocks. Tissue injury can cause rapid mitochondrial depolarization that compromises ATP production and/or results in cell death. The loss of ATP can further impair cell proliferation and/or tissue repair. Mitochondrial potential can be monitored in the cells at the edge of the scratch area using the cell-permeable potential-dependent dye TMRM (tetramethylrhodamine methyl ester). TMRM can accumulate in negatively charged polarized mitochondria and can be detected as red fluorescence.

To mimic the microenvironment of wounds in vitro, serum-free medium was used in the scratch assay. On the day of the scratch assay, the medium was replaced with serum-free DMEM, and a line scraped across the HK-2 cell monolayer using a p1000 pipette tip. Cells were washed to remove debris and replaced with DMEM alone (control), or DMEM supplemented with 10 nM free biotin or peptide-conjugated biotin molecules for 24 hours. HK-2 cells were then incubated with 5 nM TMRM in DMEM without phenol red and incubated for 30 min. Cells were then covered with live cell image buffer and imaged using Nikon Eclipse Ti2 fluorescent microscope (20× objective).

Figure 24:
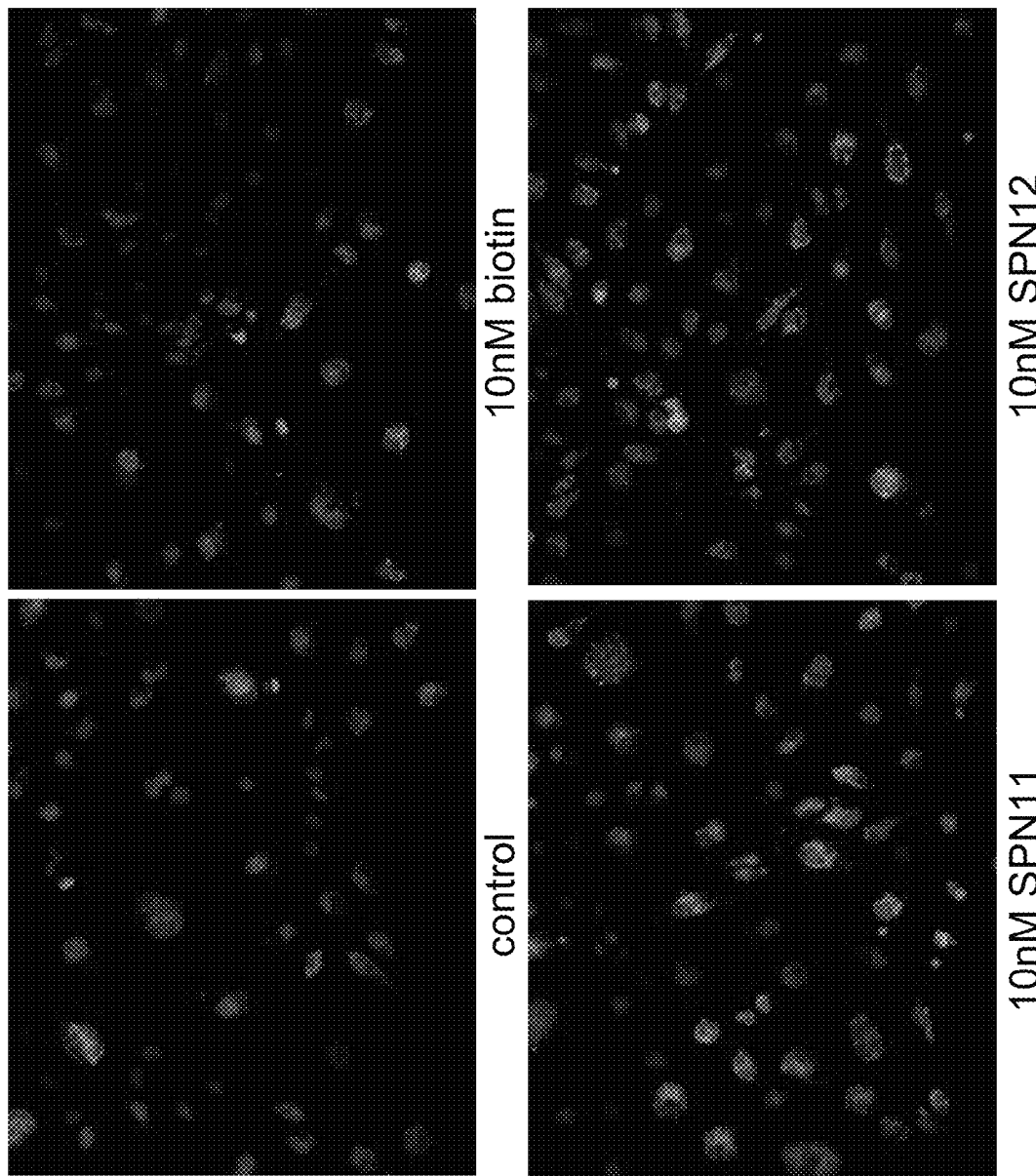
FIG. 24 are microscopic images related to mitochondrial potential of certain exemplary compounds.

FIG. 24 shows representative microscopic images (200× magnification) of mitochondrial potential in HK-2 cells 24 hours after mechanical scratch in serum-free medium only (control), or in serum-free medium containing 10 nM biotin, SPN11, or SPN12. Mitochondrial potential is detected with TMRM, which stains red, while nuclei stain blue with Hoechst. Under control conditions, few cells at the edge of the scratch showed TMRM staining, indicating that many cells underwent mitochondrial depolarization Addition of 10 nM SPN11, or SPN12 increased the number of cells with good mitochondrial potential, whereas biotin had no effect.

Figure 25:
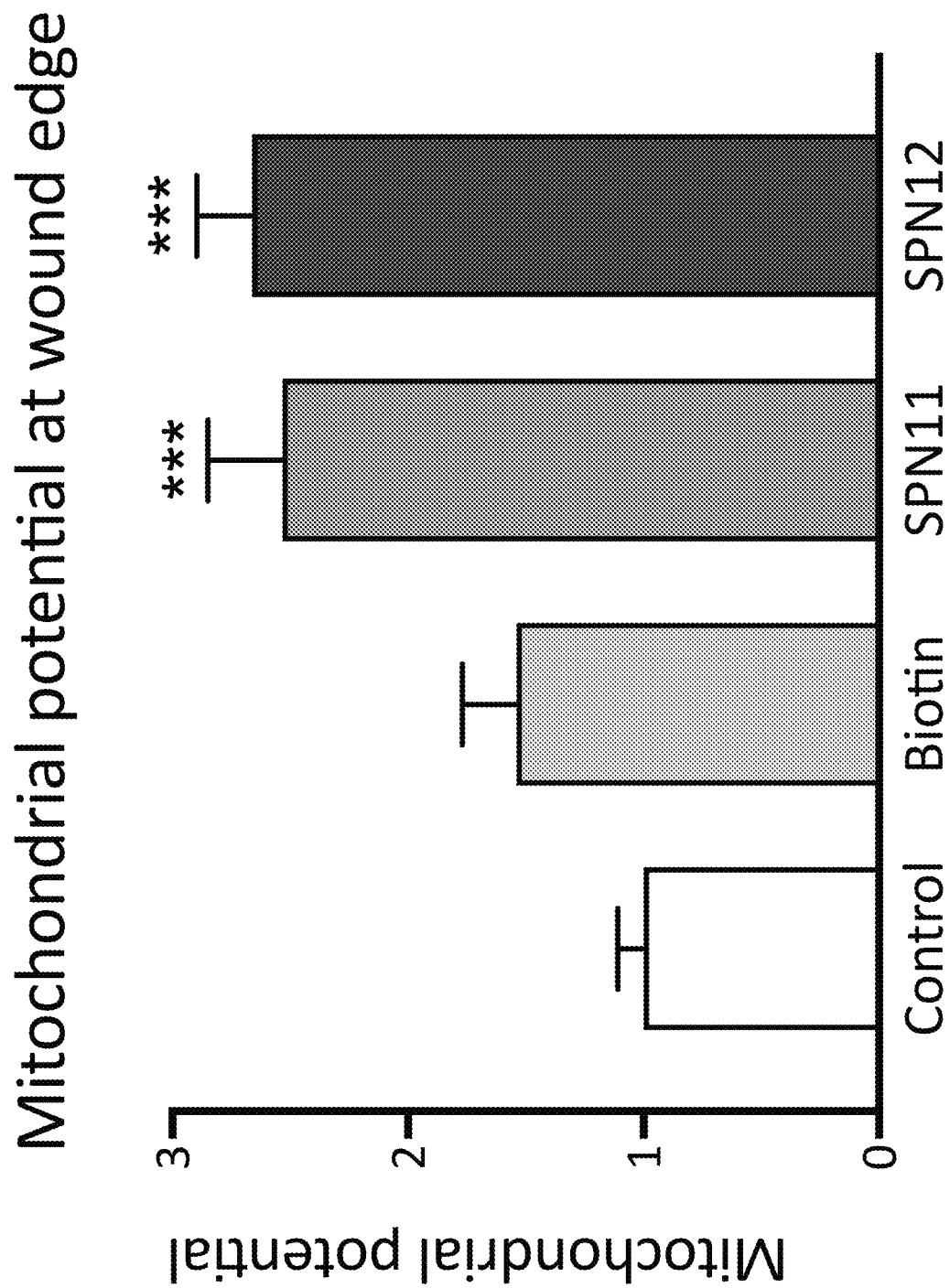
FIG. 25 is a graph showing exemplary mitochondrial potential.

FIG. 25 is a graph summarizing the ratio of mitochondrial potential (red fluorescence) normalized to nuclear number (blue fluorescence) in HK-2 cells 24 hours after mechanical scratch in serum-free medium only (control), or in serum-free medium containing 10 nM biotin or peptide-conjugated biotin molecules. Incubation with SPN11, or SPN12 significantly increased mitochondrial potential in cells at the edge of the scratch (***P<0.001, compared to control). The effect of free biotin did not reach statistical significance.

These results demonstrate that the biotin-conjugated peptides (SPN11 and SPN12) are superior to free biotin in preserving mitochondrial potential in a wound setting because of their targeted delivery to the inner mitochondrial membrane. This can translate to better increase in ATP production and cell proliferation.

Example 9—Uptake and Distribution of SPN15 to Mouse Retina after Intraperitoneal Administration To demonstrate that the peptide-conjugated biotin molecules can be administered in vivo, we have determined the uptake and distribution of SPN15 in a mouse following intraperitoneal (ip) administration.

SPN15 (30 mg/kg) was administered ip to a 13-month-old male mouse (C57BL/6J strain). At 2-hours after administration, the mouse was anesthetized with an overdose of ketamine/xylazine, and the eyes enucleated. After the cornea and lens were removed, the eyecup was fixed for 1.25 hours in 4% paraformaldehyde in 0.1M Tris buffer. The eyecup was then rinsed 3 times for 10 minutes each in Tris buffer and then cryoprotected in 10%, 20%, and 30% sucrose before sectioning at 30 um with a Leica 3050 cryostat. Sections were stored at −20° C. until used.

To label biotin on SPN15, sections were incubated with Streptavidin conjugated AlexaFluor 594 (1:500) from Jackson ImmunoResearch, West Grove, Pa.). ToPro 3 (nuclear stain, 1:1000, Molecular Probes) was used to stain cell nuclei. Mitochondria localization was determined using an antibody to Cox IV (cytochrome c oxidase subunit 4; PA529992, 1:300, Invitrogen) and Mitotracker Red (1:1500 in Tris, Invitrogen). All incubations were carried out in microwave (150 W) except for Cox IV and Mitotracker labeling, which was done with primary antibody overnight at 4° C. followed by secondary antibody (AF488 conjugated donkey anti-rabbit, Jackson Immunoresearch). Sections were imaged using the Olympus Fluoview 300 with helium, argon and neon lasers using 40× oil immersion lens at a resolution of 1024×1024.

Figure 26:
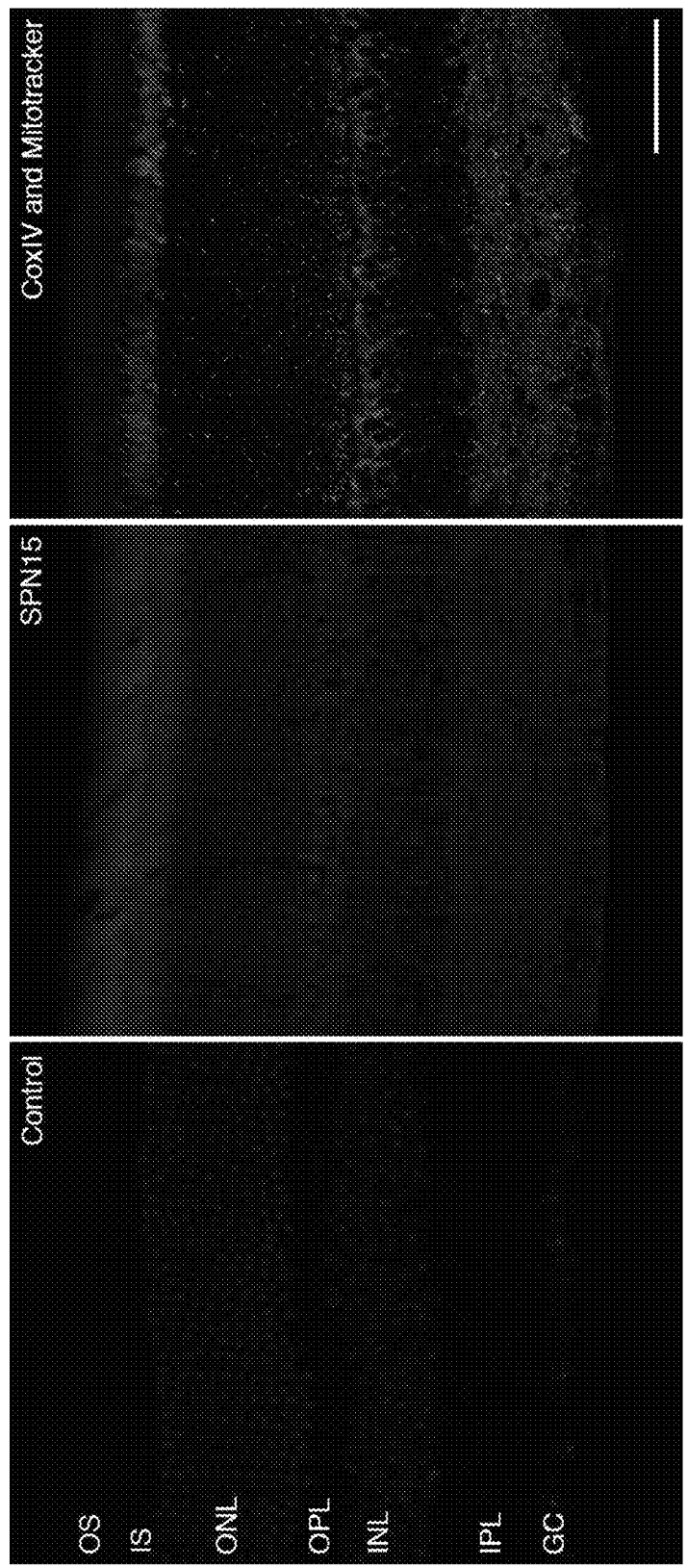
FIG. 26 are fluorescent microscopic images related to retina uptake of certain exemplary compound.

FIG. 26 (left panel) is a cryostat section from a control mouse without peptide administration showing nuclei labeled with TOPRO (blue) in the different layers of the retina, where OS=outer segment; IS=inner segment; ONL=outer nuclear layer; OPL=outer plexiform layer; INL=inner nuclear layer; IPL=inner plexiform layer; RGC=retinal ganglion cell.

FIG. 26 (right panel) is a cryostat section from a control mouse stained for COX4, which is a protein expressed on the inner mitochondrial membrane (green), Mitotracker Red, which is a fluorescent that labels mitochondria (red), and TOPRO, which labels nuclei (blue). COX4 staining for mitochondria is clearly seen in the photoreceptor 1S with their abundant mitochondria, and the INL, IPL and the RGC.

The staining of Mitotracker Red in the photoreceptor OS is surprising because there are no mitochondria in the OS.

FIG. 26 (middle panel) is a cryostat section from a mouse 2 hours after SPN15 administration. SPN15 is clearly taken up in the different layers of the retina as visualized by Streptavidin Alexa Fluor 594 (red) staining. The SPN15 staining is concentrated in the inner and outer plexiform layers (IPL and OPL), where synapses between ganglion, bipolar and amacrine cells in the inner nuclear layer (INL) and photoreceptors. Streptavidin staining co-localizes with COX4 staining in the RGC, IPL, INL, and the photoreceptor IS. An exception is the intense streptavidin staining in the photoreceptor OS where there is absence of COX4 staining. It is unclear why SPN15 is so heavily distributed to the OS which contains densely-packed disks responsible for light transduction.

Figure 27:
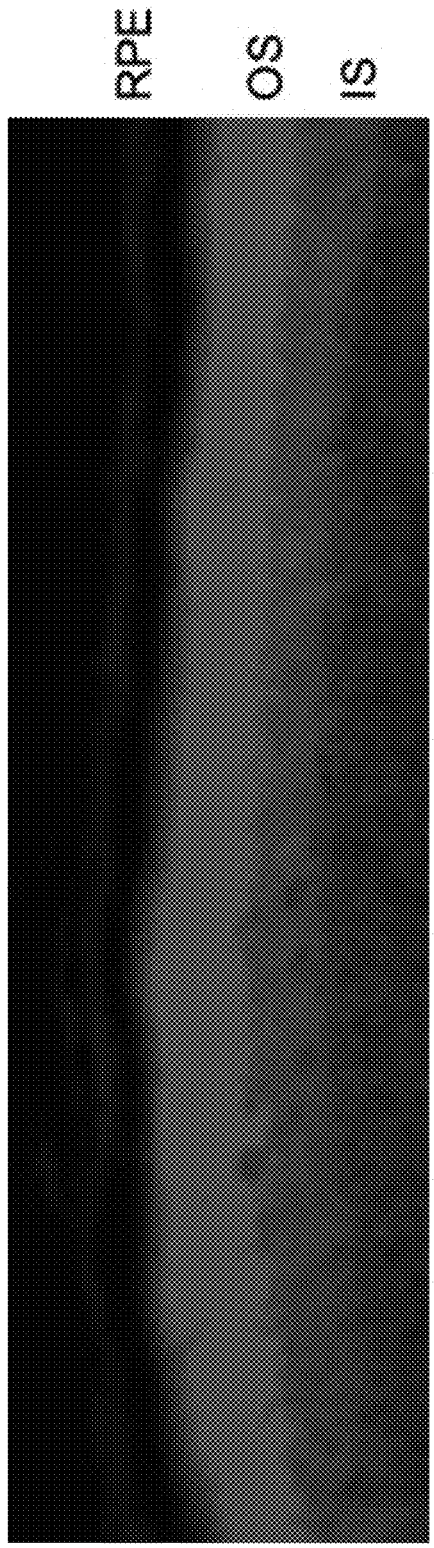
FIG. 27 is a fluorescent microscopic image related to retina uptake of certain exemplary compound.

FIG. 27 is an enlargement of the photoreceptor IS and OS. The retinal pigment epithelium (RPE) is a single layer of cells above the OS. SPN15 staining can clearly be seen in the RPE cells.

These results show that SPN15 is rapidly absorbed after ip administration in a living mouse and is widely distributed throughout the retina. There are two sources of blood supply to the mammalian retina: the central retinal artery and the choroidal blood vessels. The central retinal artery starts at the optic nerve to supply the inner retinal layers. The choroid blood flow is vital for the maintenance of the outer retina (photoreceptors and retinal pigment epithelium (RPE). The streptavidin staining indicates that SPN15 is distributed through both vascular systems.

SPN15 staining is concentrated in the inner and outer plexiform layers (IPL and OPL). The outer nuclear layer (ONL) contains cell bodies of the rods and cones, and the inner nuclear layer (INL) contains cell bodies of ganglion cells, horizontal cells and amacrine cells. The OPL is where synapses between rods and cones, and vertically running bipolar cells and horizontally oriented cells occur. The IPL functions as a relay station for the bipolar cells to the ganglion cells, and this is where the message concerning the visual image is transmitted to the brain along the optic nerve.

SPN15 is also concentrated in the inner segment (IS) that contains aggregates of very long thin mitochondria to support metabolism of both rod and cone photoreceptors. The high concentration of SPN15 in the IS is expected due to the density of mitochondria. These mitochondria play a role in the biosynthesis of the numerous lipid disks in the outer segment (OS) that contains the visual pigment molecules (rhodopsin) for visual transduction. The very high concentration of SPN15 in the OS is unexpected as there is a complete absence of mitochondria. This is confirmed by the lack of staining for COX4 in the OS. The staining of OS by Mitotracker has been reported but the reason is unclear and would require further investigation. The concentration of SPN15 in the OS can be important for maintenance of disk stability.

The OS disks suffer light-induced oxidative damage and are normally phagocytized by the retinal pigment epithelium (RPE) and degraded by lysosomal degradation, allowing rhodopsin to be recycled, and the generation of ketone bodies which can be used as metabolic fuel by photoreceptors. The RPE is a single layer of cell between the OS and the choroid that also forms the blood-retinal barrier. The distribution of SPN15 in the RPE layer is highlighted in FIG. 27.

These findings confirm that SPN15 can be distributed to areas of high mitochondrial density in the retina after systemic administration. They suggest that SPN15 and other peptide-conjugated biotin molecules can be beneficial for numerous ophthalmic diseases. The targeting of RPE suggests SPN15 can improve mitochondrial bioenergetics in aging and combat age-related macular degeneration and diabetic retinopathy. This is supported by the results that SPN compounds preserve mitochondrial potential, increase ATP synthesis, improve cell viability, and increase cell proliferation in ARPE-19 cells, a human retinal pigment epithelial cell line. SPN15 also can increase viability of retinal ganglion cells under increased pressure from glaucoma and result in optic nerve damage.

Definitions

When the following phrases are used substantively herein, the accompanying definitions apply. These phrases and definitions are presented without prejudice, and, consistent with the application, the right to redefine these phrases via amendment during the prosecution of this application or any application claiming priority hereto is reserved. For the purpose of interpreting a claim of any patent that claims priority hereto, each definition in that patent functions as a clear and unambiguous disavowal of the subject matter outside of that definition.

a—at least one.

activity—an action, act, step, and/or process or portion thereof.

adapt—to design, make, set up, arrange, shape, configure, and/or make suitable and/or fit for a specific purpose, function, use, and/or situation.

add—to join and/or unite (something) to something else in order to increase the size, quantity, effect, and/or scope.

administer—to give and/or apply.

alcohol—any of a class of chemical compounds having the general formula ROH, where R represents an alkyl group and —OH a hydroxyl group, as in methyl alcohol, CH3OH, or ethyl alcohol, C2H5OH.

alternating—designating or relating to every other one of a series.

amine—any of a group of organic compounds of nitrogen, such as ethylamine, C2H5NH2, that may be considered ammonia derivatives in which one or more hydrogen atoms have been replaced by a hydrocarbon group.

amino acid—a compound in which at least one amino group and at least one carboxyl group are bound to the same carbon skeleton and the nitrogen atom of the amino group may form part of a ring, such compounds including the L- and D-isomers of the natural amino acids.

and—in conjunction with.

and/or—either in conjunction with or in alternative to.

antibiotics—a substance, such as penicillin or erythromycin, produced by and/or derived from certain microorganisms, including fungi and bacteria, that can destroy or inhibit the growth of other microorganisms, especially bacteria. Antibiotics are widely used in the prevention and treatment of infectious diseases.

anticonvulsant—any of a class of drugs used to prevent or abolish convulsions.

antioxidant—substances that reduce the production of reactive oxygen species, inhibit the oxidation of other substances, substances that retard the deterioration of other substances by oxidation, and/or scavengers of free radical species, reactive oxygen species, hydroxyl radical species, oxidized lipids, and/or lipid peroxidation products.

any—one, some, every, and/or all without specification.

apparatus—an appliance or device for a particular purpose.

approximately—about and/or nearly the same as, including for each value in a series of two or more numerical values; within an acceptable error for a particular value as determined by a person having ordinary skill in the art, which depends in part on how the value is measured or determined; within one standard deviation; when no particular margin of error (e.g., a standard deviation to a mean value given in a chart or table of data) is recited, the range that encompasses the recited value and would be included by rounding up or down to the recited value as well, taking into account significant figures; and/or within ±20%, 15%, 10%, or 5% of the specified value.

aromatic—an organic compound having an unsaturated ring containing alternating double and single bonds, including those compounds having a benzene ring.

arrange—to dispose in a particular order.

associate—to join, connect together, and/or relate.

at—in, on, and/or near.

at least—not less than, and possibly more than, which applies to each value in any series of values that the phrase "at least" precedes.

be—to exist in actuality.

biologically-active—configured to alter cell biology.

biotin—a crystalline, water-soluble vitamin, $C_{10}H_{16}O_3N_2S$, of the vitamin B complex, sometimes referred to as vitamin B7 and/or vitamin H.

biotinidase—an enzyme, which in humans is encoded by the BTD gene, that readily cleaves and/or breaks down biotin amides, releasing free biotin and the amine, and which the main substrate of which is biocytin, or biotin linked to lysine; biotinidase is also capable of breaking apart biotin esters.

biotinylated—a polypeptide having a biotin molecule located at one or more of its terminals.

C-terminus—(also known as the carboxyl-terminus, carboxy-terminus, C-terminal tail, C-terminal end, or COOH-terminus) the end of an amino acid chain (protein or polypeptide), terminated by a free carboxyl group (—COOH).

can—is capable of, in at least some embodiments.

carrier—a substance to which an active ingredient and/or agent is added as a way of applying and/or transferring that active ingredient and/or agent.

cationic—an ion or group of ions having a positive charge and characteristically moving toward the negative electrode in electrolysis.

cause—to bring about, provoke, precipitate, produce, elicit, be the reason for, result in, and/or effect.

caused by—resulting from.

cell—the smallest structural unit of an organism that is capable of independent functioning, consisting of cytoplasm, usually one nucleus, and various other organelles, all surrounded by a semipermeable cell membrane.

cell-permeable—capable of freely moving passively into and out of cells.

cellular—of, relating to, or consisting of cells.

chemically-defined medium—those mediums in which all components in the medium are identified with exact concentrations and the medium contains no added animal or human serum, growth factors, hormones, etc.

composition of matter—a combination, reaction product, compound, mixture, formulation, material, and/or composite formed by a human and/or automation from two or more substances and/or elements.

compound—a pure, macroscopically homogeneous substance consisting of atoms or ions of two or more different elements in definite proportions that cannot be separated by physical means. A compound usually has properties unlike those of its constituent elements.

comprising—including but not limited to.

conceive—to imagine, conceptualize, form, and/or develop in the mind.

configure—to design, arrange, set up, shape, and/or make suitable and/or fit for a specific purpose, function, use, and/or situation.

conjugate—to link two chemical compounds together via a covalent bond.

conservative substitution—the substitution of an amino acid in a polypeptide with a functionally, structurally, and/or chemically similar natural or unnatural amino acid, such as the following groups each contain natural amino acids that are conservative substitutions for one another:
  1) Glycine (Gly/G), Alanine (Ala/A);
  2) Isoleucine (Ile/I), Leucine (Leu/L), Methionine (Met/M), Valine (Val/V);
  3) Phenylalanine (Phe/F), Tyrosine (Tyr/Y), Tryptophan (Trp/W);
  4) Serine (Ser/S), Threonine (Thr/T), Cysteine (Cys/C);
  5) Asparagine (Asn/N), Glutamine (Gln/Q);
  6) Aspartic acid (Asp/D), Glutamic acid (Glu/E); and/or
  7) Arginine (Arg/R), Lysine (Lys/K), Histidine (His/H).

and/or the following groups, which each contain natural amino acids that are conservative substitutions for one another:
  1) non-polar: Ala, Val, Leu, Ile, Met, Pro (proline/P), Phe, Trp;
  2) hydrophobic: Val, Leu, Ile, Phe, Trp;
  3) aliphatic: Ala, Val, Leu, Ile;
  4) aromatic: Phe, Tyr, Trp, His;
  5) uncharged polar or hydrophilic: Gly, Ala, Ser, Thr, Cys, Asn, Gln, Tyr;
  6) aliphatic hydroxyl- or sulfhydryl-containing: Ser, Thr, Cys;
  7) amide-containing: Asn, Gln;
  8) acidic: Asp, Glu;
  9) basic: Lys, Arg, His; and/or
  10) small: Gly, Ala, Ser, Cys.

and/or the following groupings:
  1) hydrophobic: Val, Leu, Ile, Met, Phe, Trp;
  2) aromatic: Phe, Tyr, Trp, His;
  3) neutral hydrophilic: Gly, Ala, Ser, Thr, Cys, Asn, Gln;
  4) acidic: Asp, Glu;
  5) basic: Lys, Arg, His; and/or
  6) residues that influence backbone orientation: Pro, Gly.

consisting—relating to a closed group (and its legal equivalents) that otherwise excludes anything not listed.

consume—to eat and/or drink; to take into the body by the mouth for digestion and/or absorption.

containing—including but not limited to.

convert—to transform, adapt, and/or change.

corresponding—related, associated, accompanying, similar in purpose and/or position, conforming in every respect, and/or equivalent and/or agreeing in amount, quantity, magnitude, quality, and/or degree.

create—to bring into being.

culture media—a nutritive substance, such as an agar gel or liquid medium, in which cultures of bacteria, fungi, animal cells, or plant cells are grown and/or cultivated for scientific purposes.

deficiency—a state and/or condition that deviates from a desired state and/or condition.

define—to establish the meaning, relationship, outline, form, and/or structure of;

and/or to precisely and/or distinctly describe and/or specify.

delivery—an act of conveying and/or transferring.

derive—to receive, obtain, and/or produce from a source and/or origin.

determine—to find out, obtain, calculate, decide, deduce, ascertain, and/or come to a decision, typically by investigation, reasoning, and/or calculation.

device—a machine, manufacture, and/or collection thereof.

each—every one of a group considered individually.

effective—sufficient to bring about, provoke, elicit, and/or cause.

embodiment—an implementation, manifestation, and/or concrete representation.

estimate— (n) a calculated value approximating an actual value; (v) to calculate and/or determine approximately and/or tentatively.

excessive—exceeding a normal, usual, reasonable, and/or proper limit.

exemplary—serving as an example, instance, and/or illustration, but not necessarily preferred or advantageous over other embodiments or features.

first—an initial cited element of a set.

formulation—a medicinal preparation administered in a specific form, such as a tablet, linctus, ointment, or injection.

from—used to indicate a source, origin, and/or location thereof.

general alternating—having the identified sequence or its inverse, e.g., aromatic-cationic or cationic-aromatic, such as a peptide sequence with A-C-A-C-A-C or C-A-C-A-C-A residues (where A stands for aromatic and C for cationic).

generate—to create, produce, give rise to, and/or bring into existence.

greater than—at least.

group—(n.) a number of individuals and/or things considered together because of one or more similarities; (v.) to associate a number of individuals or things such that they are considered together and/or caused to have similar properties.

having—including but not limited to.

health—the overall condition of an organism at a given time; soundness, especially of body and/or mind; freedom from disease, injury, disorder, and/or abnormality.

improve—to change to a better state and/or condition.

inadequate—insufficient.

including—having, but not limited to, what follows.

initialize—to prepare something for use and/or some future event.

injury—damage and/or harm done to and/or suffered by a person and/or thing.

install—to connect or set in position and prepare for use.

intake—the act and/or instance of taking in, ingesting, and/or receiving.

intestinal malabsorption—defective and/or inadequate absorption of nutrients from the intestinal tract.

intramuscular—within a muscle.

intranasal—within the nose.

intravenous—within a vein.

is—to exist in actuality.

lysine—a crystalline, basic, essential amino acid, H2N(CH2)4CH(NH2)COOH, produced chiefly from many proteins by hydrolysis.

maintenance—an activity relating to restoring and/or preserving performance of an item and/or system.

mammal—any of various warm-blooded vertebrate animals of the class Mammalia, including humans, characterized by a covering of hair on the skin and, in the female, milk-producing mammary glands for nourishing the young.

mammalian—of and/or relating to a mammal.

maximum—having a greatest value.

may—is allowed and/or permitted to, in at least some embodiments.

medical condition—diseases, injuries, disorders, and/or abnormalities of the body and/or mind.

medication—a substance adapted to relieve at least one symptom of and/or cure a medical condition.

metabolic—of and/or relating to metabolism.

metabolic supplement—naturally occurring compounds that enhance energy production.

metabolism—the chemical processes occurring within a living cell or organism that are necessary for the maintenance of life. In metabolism some substances are broken down to yield energy for vital processes while other substances, necessary for life, are synthesized.

method—one or more acts that are performed upon subject matter to be transformed to a different state or thing and/or are tied to a particular apparatus, said one or more acts not a fundamental principal and not pre-empting all uses of a fundamental principal.

minimum—having a lowest value.

mitigate—to make less severe, serious, or painful.

mitochondria—a spherical or elongated organelle in the cytoplasm of nearly all eukaryotic cells, containing genetic material and many enzymes important for cell metabolism, including those responsible for the conversion of food to usable energy.

mitochondria-targeted—indicates that an indicated substance (e.g., biotin) is transported to mitochondria such that, once inside the cell, the substance will be preferentially localized to mitochondria, and not substantially distributed to other cellular organelles or membranes.

more—a quantifier meaning greater in size, amount, extent, and/or degree.

motif—a recurrent pattern either of molecular sequence, usually of nucleotides or amino acids in proteins, or of molecular structure that usually corresponds to specific biological activity.

N-terminus— (also known as the amino-terminus, NH2-terminus, N-terminal end or amine-terminus) is the start of a protein or polypeptide referring to the free amine group (—NH2) located at the end of a polypeptide. Within a peptide, the amine group is bonded to another carboxylic group in a protein to make it a chain, but since the end amino acid of a protein is only connected at the carboxy-end, the remaining free amine group is called the N-terminus.

no—an absence of and/or lacking any.

one—being and/or amounting to a single unit, individual, and/or entire thing, item, and/or object.

operable—practicable and/or fit, ready, and/or adapted to be put into its intended use and/or service.

or—a conjunction used to indicate alternatives, typically appearing only before the last item in a group of alternative items.

oral—of and/or relating to the mouth.

organ—a differentiated part of an organism, such as an eye, wing, or leaf, that performs a specific function.

patient—a mammalian subject, such as a human subject.

peptide—any of various natural or synthetic compounds (including amino acid salts such as pharmaceutically acceptable salts) containing two or more amino acids covalently joined by at least one peptide and/or amide bond that links the carboxyl group of one amino acid to the amino group of another.

per—for each and/or by means of.

pharmaceutically acceptable—a substance (e.g., an active ingredient or an excipient) that is suitable for use in contact with the tissues and organs of a subject without excessive irritation, allergic response, immunogenicity, and/or toxicity, is commensurate with a reasonable benefit/risk ratio, is effective for its intended use, and/or is compatible with the other ingredients of any composition that comprises the substance; that which is useful in preparing a pharmaceutical composition and is generally safe, non-toxic, and neither biologically nor otherwise undesirable and includes that which is acceptable for veterinary use as well as human pharmaceutical use; and/or that which is approved and/or approvable by a regulatory agency of the Federal and/or a state government and/or the corresponding agency in countries other than the United States, and/or that is listed in the U.S. Pharmacopoeia and/or other generally recognized pharmacopoeia for use in animals, and more particularly, in humans.

plurality—the state of being plural and/or more than one.

polypeptide—a chain of amino acids linked together by peptide bonds and having a molecular weight of up to about 10,000.

polypeptides—generally peptides and proteins, for which herein the left-hand end of the polypeptide sequence is referred to as the "amino (N)-terminus", and the right-hand end of the sequence is referred to as the "carboxyl I-terminus".

portion—a part, component, section, percentage, ratio, and/or quantity that is less than a larger whole.

pre-—a prefix that precedes an activity that has occurred beforehand and/or in advance.

predetermine—to determine, decide, and/or establish in advance.

preserve—to store safely for later use.

prevent—to impede, avert, resist, hinder, stop, and/or keep from happening.

probability—a quantitative representation of a likelihood of an occurrence.

product—something produced by human and/or mechanical effort.

project—to calculate, estimate, or predict.

promote—to contribute to the progress and/or growth of; to further, advance, promote, and/or market.

protein—a linked sequence of amino acid residues containing 50 or more amino acid residues.

provide—to furnish, supply, give, and/or make available.

range—a measure of an extent of a set of values and/or an amount and/or extent of variation.

ratio—a relationship between two quantities expressed as a quotient of one divided by the other.

receive—to get as a signal, take, acquire, and/or obtain.

recommend—to suggest, praise, commend, and/or endorse.

reduce—to make and/or become lesser and/or smaller.

regeneration—regrowth of lost and/or destroyed parts and/or organs.

remove—to eliminate, remove, and/or delete, and/or to move from a place or position occupied.

repair—to restore to a desired condition.

repeat—to do again and/or perform again.

repeatedly—again and again; repetitively.

request—to express a desire for and/or ask for.

result—(n.) an outcome and/or consequence of a particular action, operation, and/or course; (v.) to cause an outcome and/or consequence of a particular action, operation, and/or course.

said—when used in a system or device claim, an article indicating a subsequent claim term that has been previously introduced.

second—a cited element of a set that follows an initial element.

select—to make a choice or selection from alternatives.

selected—chosen from a plurality of alternatives.

sequence—an ordered set.

serum-free—lacking the clear yellowish fluid obtained upon separating whole blood into its solid and liquid components after it has been allowed to clot.

set—a related plurality.

solution—a homogeneous mixture of two or more substances, which may be solids, liquids, gases, or a combination of these.

species—a class of individuals and/or objects grouped by virtue of their common attributes and assigned a common name; a division subordinate to a genus.

storage—the act of storing or the state of being stored store—to set aside, reserve, deposit, secure, and/or put away for future use.

subcutaneous—slightly below the skin.

subject—an animal, including but not limited to a mammal, such as a primate (e.g., a human, a chimpanzee, or a monkey), a rodent (e.g., a rat, a mouse, a guinea pig, a gerbil, or a hamster), a lagomorph (e.g., a rabbit), a bovine (e.g., a cattle), a suid (e.g., a pig), a caprine (e.g., a sheep), an equine (e.g., a horse), a canine (e.g., a dog), and/or a feline (e.g., a cat).

sublingual—situated beneath and/or on the underside of the tongue.

substantially—to a great extent and/or degree.

suffer—to feel pain or distress; to sustain injury and/or harm; to endure, be afflicted with, and/or be ill with; to be accurately diagnosed with.

supplement—(n.) a product containing one or more vitamins, herbs, enzymes, amino acids, and/or other ingredients, that is taken to supplement one's diet, as by providing a missing nutrient.

system—a collection of mechanisms, devices, machines, articles of manufacture, processes, compositions of matter, data, and/or instructions, the collection designed to perform one or more specific functions.

target—to interact with.

therapeutically—of or relating to the medical treatment of a disease, injury, disorder, and/or abnormality.

therapeutically effective amount—an amount of a substance that, when administered to a subject, is sufficient to prevent, reduce the risk of developing, delay the onset of, slow the progression of, and/or cause regression of the medical condition being treated, and/or to alleviate to some extent the medical condition and/or one or more symptoms and/or complications of that condition, at least in some fraction of the subjects taking that substance, and/or to elicit the biological and/or medical response of a cell, tissue, organ, system, animal, and/or human that is sought by a researcher, veterinarian, medical doctor, and/or clinician.

tissue—an aggregation of morphologically similar cells and associated intercellular matter acting together to perform one or more specific functions in the body.

tissue regeneration—re-growth of tissue through cell proliferation that completely restores portion of damaged tissue to their normal state.

tissue repair—the restoration of tissue architecture and function after an injury, said restoration encompassing tissue regeneration and tissue replacement.

tissue replacement—those types of healing where the damaged tissues are repaired by laying down connective tissue or scar tissue.

topical—a localized area of the body, and typically the skin.

transdermal—through or by way of the skin.

transform—to change in measurable: form, appearance, nature, and/or character.

transmit—to send as a signal, provide, furnish, and/or supply.

transport—to convey and/or move from one place to another.

treat—to alleviate, ameliorate, inhibit the progress of, reverse, prevent, and/or abrogate a medical condition and/or one or more causes, symptoms, and/or complications associated with the condition; to handle and/or deal with someone and/or something.

uptake—to intake, consume, and/or use.

use—to put into service.

used—employed in accomplishing something.

via—by way of and/or utilizing.

vitamin—any of various fat-soluble or water-soluble organic substances that are essential in minute amounts for normal growth and activity of living organisms, such substances synthesized by bacteria and/or plants and/or obtained by animals chiefly in their diet; and/or an organic substance, other than a protein, carbohydrate, or fat, that is an essential constituent of the food of an animal to which the vitamin is administered, e.g., B group vitamins including B1 (thiamine), B2 (riboflavin), B3 (niacin, niacinaide), B5 (pantothenic acid), B6 (pyridoxine), B7 (biotin), B9 (folate), and B12 (cyanocobalamine), Vitamin C (ascorbic acid), vitamin D and vitamin K.

water-soluble—capable of being dissolved in water.

weight—a force with which a body is attracted to Earth or another celestial body, equal to the product of the object's mass and the acceleration of gravity; and/or a factor and/or value assigned to a number in a computation, such as in determining an average, to make the number's effect on the computation reflect its importance, significance, preference, impact, etc.

wherein—in regard to which; and; and/or in addition to.

with—accompanied by.

zone—a region and/or volume having at least one predetermined boundary.

Note

Various substantially and specifically practical and useful exemplary embodiments of the claimed subject matter are described herein, textually and/or graphically, including the best mode, if any, known to the inventor(s), for implementing the claimed subject matter by persons having ordinary skill in the art. References herein to "in one embodiment", "in an embodiment", or the like do not necessarily refer to the same embodiment.

Any of numerous possible variations (e.g., modifications, augmentations, embellishments, refinements, and/or enhancements, etc.), details (e.g., species, aspects, nuances, and/or elaborations, etc.), and/or equivalents (e.g., substitutions, replacements, combinations, and/or alternatives, etc.) of one or more embodiments described herein might become apparent upon reading this document to a person having ordinary skill in the art, relying upon his/her expertise and/or knowledge of the entirety of the art and without exercising undue experimentation. The inventor(s) expects any person having ordinary skill in the art, after obtaining authorization from the inventor(s), to implement such variations, details, and/or equivalents as appropriate, and the inventor(s) therefore intends for the claimed subject matter to be practiced other than as specifically described herein. Accordingly, as permitted by law, the claimed subject matter includes and covers all variations, details, and equivalents of that claimed subject matter. Moreover, as permitted by law, every combination of the herein described characteristics, functions, activities, substances, and/or structural elements, and all possible variations, details, and equivalents thereof, is encompassed by the claimed subject matter unless otherwise clearly indicated herein, clearly and specifically disclaimed, or otherwise clearly unsuitable, inoperable, or contradicted by context.

The use of any and all examples, or exemplary language (e.g., "such as") provided herein, is intended merely to better illuminate one or more embodiments and does not pose a limitation on the scope of any claimed subject matter unless otherwise stated. No language herein should be construed as indicating any non-claimed subject matter as essential to the practice of the claimed subject matter.

Thus, regardless of the content of any portion (e.g., title, field, background, summary, description, abstract, drawing figure, etc.) of this document, unless clearly specified to the contrary, such as via explicit definition, assertion, or argument, or clearly contradicted by context, with respect to any claim, whether of this document and/or any claim of any document claiming priority hereto, and whether originally presented or otherwise:

there is no requirement for the inclusion of any particular described characteristic, function, activity, substance, or structural element, for any particular sequence of activities, for any particular combination of substances, or for any particular interrelationship of elements;

no described characteristic, function, activity, substance, or structural element is "essential"; and within, among, and between any described embodiments:

any two or more described substances can be mixed, combined, reacted, separated, and/or segregated;

any described characteristic, function, activity, substance, component, and/or structural element, or any combination thereof, can be specifically included, duplicated, excluded, combined, reordered, reconfigured, integrated, and/or segregated;

any described interrelationship, sequence, and/or dependence between any described characteristics, functions, activities, substances, components, and/or structural elements can be omitted, changed, varied, and/or reordered;

any described activity can be performed manually, semi-automatically, and/or automatically;

any described activity can be repeated, performed by multiple entities, and/or performed in multiple jurisdictions.

The use of the terms "a", "an", "said", "the", and/or similar referents in the context of describing various embodiments (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted.

When any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate sub-range defined by such separate values is incorporated into the specification as if it were individually recited herein. For example, if a range of 1 to 10 is described, that range includes all values therebetween, such as for example, 1.1, 2.5, 3.335, 5, 6.179, 8.9999, etc., and includes all sub-ranges therebetween, such as for example, 1 to 3.65, 2.8 to 8.14, 1.93 to 9, etc., even if those specific values or specific sub-ranges are not explicitly stated.

When any phrase (i.e., one or more words) appearing in a claim is followed by a drawing element number, that drawing element number is exemplary and non-limiting on claim scope.

No claim or claim element of this document is intended to invoke 35 USC 112(f) unless the precise phrase "means for" is followed by a gerund.

Any information in any material (e.g., a United States patent, United States patent application, book, article, web page, etc.) that has been incorporated by reference herein, is incorporated by reference herein in its entirety to its fullest enabling extent permitted by law yet only to the extent that no conflict exists between such information and the other definitions, statements, and/or drawings set forth herein. In the event of such conflict, including a conflict that would render invalid any claim herein or seeking priority hereto, then any such conflicting information in such material is specifically not incorporated by reference herein. Any specific information in any portion of any material that has been incorporated by reference herein that identifies, criticizes, or compares to any prior art is not incorporated by reference herein.

Applicant intends that each claim presented herein and at any point during the prosecution of this application, and in any application that claims priority hereto, defines a distinct patentable invention and that the scope of that invention must change commensurately if and as the scope of that claim changes during its prosecution. Thus, within this document, and during prosecution of any patent application related hereto, any reference to any claimed subject matter is intended to reference the precise language of the then-pending claimed subject matter at that particular point in time only.

Accordingly, every portion (e.g., title, field, background, summary, description, abstract, drawing figure, etc.) of this document, other than the claims themselves and any provided definitions of the phrases used therein, is to be regarded as illustrative in nature, and not as restrictive. The scope of subject matter protected by any claim of any patent that issues based on this document is defined and limited only by the precise language of that claim (and all legal equivalents thereof) and any provided definition of any phrase used in that claim, as informed by the context of this document when reasonably interpreted by a person having ordinary skill in the relevant art.

SEQUENCE LISTING

```
Sequence total quantity: 2
SEQ ID NO: 1            moltype = AA  length = 4
FEATURE                 Location/Qualifiers
source                  1..4
                        mol_type = protein
                        note = Cell-penetrating peptide sequence
                        organism = unidentified
SITE                    4
                        note = C-term NH2 modified Lysine
SEQUENCE: 1
WRWK                                                                    4

SEQ ID NO: 2            moltype = AA  length = 4
FEATURE                 Location/Qualifiers
source                  1..4
                        mol_type = protein
                        note = Cell-penetrating peptide sequence
                        organism = unidentified
SITE                    4
                        note = C-term OH modified Lysine
SEQUENCE: 2
WRWK                                                                    4
```

What is claimed is:

1. A method for producing mammalian cells, the method comprising:
    proliferating the mammalian cells in a culture medium, wherein:
        the culture medium comprises an effective amount of:
            one or more biologically active, water-soluble, cell-permeable, mitochondria-targeted compounds selected from a biotinylated polypeptide group, each biologically active, water-soluble, cell-permeable, mitochondria-targeted compound in the biotinylated polypeptide group defined by:
                a plurality of amino acids arranged with a general alternating aromatic-cationic motif;
                a minimum of four amino acids and a maximum of six amino acids; and
                a first D-biotin conjugated to a lysine located at the C-terminus or the N-terminus of that biotinylated polypeptide, wherein the biotinylated polypeptide is optionally amidated at the C-terminus.

2. The method according to claim 1, wherein the culture medium comprises:
    an effective amount of one or more vitamins selected from a vitamin group consisting of:
        vitamin B1 (thiamine);
        vitamin B2 (riboflavin);
        vitamin B3;
        vitamin B5 (pantothenic acid);
        vitamin B6; and
        vitamin B7 (biotin).

3. The method according to claim 1, wherein the culture medium comprises:
an effective amount of one or more amino acids selected from an amino acid group consisting of:
L-Leucine;
L-Isoleucine;
L-Valine;
L-Glutamine;
L-Serine;
L-Arginine;
L-Methionine;
L-Tryptophan; and
Glycine.

4. The method according to claim 1, wherein the culture medium comprises:
an effective amount of one or more metabolic supplements selected from a metabolic supplement group consisting of:
pyruvate;
carnitine;
acetylcarnitine;
creatine;
α-ketoglutarate;
α-lipoic acid;
nicotinamide riboside; and
nicotinamide mononucleotide.

5. The method according to claim 1, wherein the biotinylated polypeptide group consists of:
D-Trp-D-Arg-D-Trp-D-Lys(biotinyl)-OH (SPN09);
L-Trp-L-Arg-L-Trp-L-Lys(biotinyl)-NH$_2$ (SPN11);
D-Arg-L-Tyr-D-Arg-L-Phe-L-Lys(biotinyl)-NH$_2$ (SPN15);
D-Biotin-L-Trp-L-Arg-L-Trp-L-Lys(biotinyl)-NH$_2$ (SPN12); and
D-Biotin-D-Arg-L-Tyr-D-Arg-L-Phe-L-Lys(biotinyl)-NH$_2$ (SPN16).

6. The method according to claim 1, wherein:
the culture medium is free of animal serum.

7. The method according to claim 1, wherein:
the culture medium is free of growth factors.

8. The method according to claim 1, further comprising:
increasing intracellular biotin in the mammalian cells by 50 percent via exposure of the mammalian cells to the one or more biologically active, water-soluble, cell-permeable, mitochondria-targeted compounds in the culture medium versus exposure of the mammalian cells to free biotin in a reference culture medium.

9. The method according to claim 1, further comprising:
increasing intracellular biotin in the mammalian cells by 50 percent via exposure of the mammalian cells to one or more biologically active, water-soluble, cell-permeable, mitochondria-targeted compounds in the culture medium versus exposure of the mammalian cells to free biotin in a reference culture medium, the one or more biologically active, water-soluble, cell-permeable, mitochondria-targeted compounds in the mammalian cells selectively localized in the mitochondria of the mammalian cells.

10. The method according to claim 1, further comprising:
adding the one or more biologically active, water-soluble, cell-permeable, mitochondria-targeted compounds to the culture medium during ex vivo expansion of mammalian cells.

11. The method according to claim 1, further comprising:
increasing viability of the mammalian cells by 35% (compared to a serum-free control culture medium lacking the one or more biologically active, water-soluble, cell-permeable, mitochondria-targeted compounds) when the culture medium is serum-free for 11 days.

12. The method according to claim 1, further comprising:
increasing viability of the mammalian cells by 100% (compared to a serum-free control culture medium lacking the one or more biologically active, water-soluble, cell-permeable, mitochondria-targeted compounds) when the culture medium is serum-free for 30 days.

13. The method according to claim 1, further comprising:
increasing ATP concentration in the mammalian cells by 30% (compared to a serum-free control culture medium lacking the one or more biologically active, water-soluble, cell-permeable, mitochondria-targeted compounds but containing approximately 10 nM free biotin) when the culture medium is serum-free for 7 days.

14. The method according to claim 1, further comprising:
increasing proliferation and migration of mammalian cells to reduce a cell-free area in a serum-free cell culture by 25% within 24 hours when compared to control culture medium that is serum-free but does not comprise the one or more biologically active, water-soluble, cell-permeable, mitochondria-targeted compounds selected from the biotinylated polypeptide group.

15. The method according to claim 1, further comprising:
increasing proliferation and migration of mammalian cells to reduce a cell-free area in a serum-free cell culture by 25% within 24 hours when compared to a control culture medium that is serum-free containing free biotin but does not comprise the one or more biologically active, water-soluble, cell-permeable, mitochondria-targeted compounds selected from the biotinylated polypeptide group.

16. The method according to claim 1, further comprising:
promoting proliferation of the mammalian cells adjacent to a cell-free area by 35% within 24 hours when compared to a control culture medium that is serum-free but does not comprise the one or more biologically active, water-soluble, cell-permeable, mitochondria-targeted compounds selected from the biotinylated polypeptide group.

17. The method according to claim 1, further comprising:
increasing average mitochondrial potential of the mammalian cells adjacent to a cell-free area by 150% within 24 hours when compared to a control culture medium that is serum-free and does not comprise the one or more biologically active, water-soluble, cell-permeable, mitochondria-targeted compounds selected from the biotinylated polypeptide group.

18. A method for improving proliferation of mammalian cells ex vivo, the method comprising:
expanding the mammalian cells in a culture medium comprising one or more compounds selected from a biotinylated polypeptide group consisting of:
D-Trp-D-Arg-D-Trp-D-Lys(biotinyl)-OH (SPN09);
L-Trp-L-Arg-L-Trp-L-Lys(biotinyl)-NH$_2$ (SPN11);
D-Arg-L-Tyr-D-Arg-L-Phe-L-Lys(biotinyl)-NH$_2$ (SPN15);
D-Biotin-L-Trp-L-Arg-L-Trp-L-Lys(biotinyl)-NH$_2$ (SPN12); and
D-Biotin-D-Arg-L-Tyr-D-Arg-L-Phe-L-Lys(biotinyl)-NH$_2$ (SPN16).

19. The method according to claim 18, wherein the mammalian cells comprise stem cells.

20. The method according to claim 18, wherein the mammalian cells comprise primary cells.

21. The method according to claim 18, wherein the mammalian cells comprise myoblasts.

22. The method according to claim 18, wherein the mammalian cells comprise mesenchymal stem cells.

23. The method according to claim 18, wherein the mammalian cells comprise progenitors cells.

24. The method according to claim 18, wherein the culture medium is free of animal serum.

25. The method according to claim 18, wherein the culture medium is free of growth factors.

26. The method according to claim 18, wherein the culture medium comprises an effective amount of one or more vitamins selected from a group of vitamins consisting of:
   vitamin B1 (thiamine);
   vitamin B2 (riboflavin);
   vitamin B3;
   vitamin B5 (pantothenic acid);
   vitamin B6;
   vitamin B7 (biotin);
   vitamin B9 (folate); and
   vitamin B12 (cyanocobalamine).

27. The method according to claim 18, wherein the culture medium comprises an effective amount of one or more amino acids selected from the amino acid group consisting of:
   L-Leucine;
   L-Isoleucine;
   L-Valine;
   L-Glutamine;
   L-Serine;
   L-Arginine;
   L-Methionine;
   L-Tryptophan; and
   Glycine.

28. The method according to claim 18, wherein the culture medium comprises an effective amount of one or more metabolic supplements selected from the metabolic supplement group consisting of:
   pyruvate;
   carnitine;
   acetylcarnitine;
   creatine;
   α-ketoglutarate;
   α-lipoic acid;
   nicotinamide riboside; and
   nicotinamide mononucleotide.

29. The method according to claim 18, wherein the mammalian cells comprise hematopoietic cells.

30. The method according to claim 18, wherein the mammalian cells comprise stem cells derived from bone marrow, placenta, and/or umbilical cord blood.

31. The method according to claim 18, wherein the mammalian cells comprise pancreatic islet cells.

\* \* \* \* \*